United States Patent
Lin et al.

(10) Patent No.: US 11,202,817 B2
(45) Date of Patent: Dec. 21, 2021

(54) DIPEPTIDOMIMETICS AS INHIBITORS OF HUMAN IMMUNOPROTEASOMES

(71) Applicant: CORNELL UNIVERSITY, Ithaca, NY (US)

(72) Inventors: Gang Lin, Forest Hills, NY (US); Carl Nathan, Larchmont, NY (US); Pradeep K. Singh, New York, NY (US)

(73) Assignee: Cornell University, Ithaca, NY (US)

(*) Notice: Subject to any disclaimer, the term of this patent is extended or adjusted under 35 U.S.C. 154(b) by 14 days.

(21) Appl. No.: 15/504,951

(22) PCT Filed: Aug. 12, 2015

(86) PCT No.: PCT/US2015/044876
§ 371 (c)(1),
(2) Date: Feb. 17, 2017

(87) PCT Pub. No.: WO2016/028571
PCT Pub. Date: Feb. 25, 2016

(65) Prior Publication Data
US 2018/0221431 A1    Aug. 9, 2018

Related U.S. Application Data

(63) Continuation of application No. PCT/US2015/044876, filed on Aug. 12, 2015.
(Continued)

(51) Int. Cl.
*A61K 38/05* (2006.01)
*C07C 271/22* (2006.01)
(Continued)

(52) U.S. Cl.
CPC ............ *A61K 38/05* (2013.01); *A61K 31/165* (2013.01); *A61K 31/42* (2013.01); *A61K 38/02* (2013.01); *C07C 237/06* (2013.01); *C07C 237/12* (2013.01); *C07C 237/22* (2013.01); *C07C 271/22* (2013.01); *C07C 311/14* (2013.01);
(Continued)

(58) Field of Classification Search
None
See application file for complete search history.

(56) References Cited

U.S. PATENT DOCUMENTS 5,763,604 A    6/1998    Ackermann et al.
8,048,911 B2   11/2011   Ogata
(Continued)

FOREIGN PATENT DOCUMENTS

CN    1984880 A      6/2007
CN    101506224 A    8/2009
(Continued)

OTHER PUBLICATIONS

PubChem CID 132071324 (Year: 2012).*
Lin et al. "N,C-capped dipeptides with selectivity for mycobacterial proteasome over human proteasomes: Role of S3 and S1 bindign pockets" J. Am. Chem. Soc. 135:9968-9971. (Year: 2013).*
(Continued)

*Primary Examiner* — Sudhakar Katakam
*Assistant Examiner* — Zachary J Miknis
(74) *Attorney, Agent, or Firm* — Troutman Pepper Hamiiton Sanders LLP (Rochester)

(57) ABSTRACT

The compounds of the present invention are represented by the following compounds having Formula I:

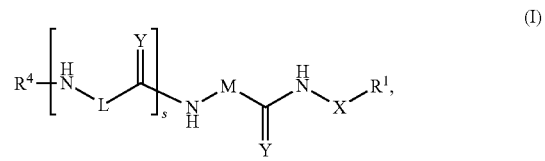

where the substituents $R^1$, $R^4$, L, M, X, Y, and s are as defined herein. The compounds of the present invention are also represented by the following compounds having Formula (Ia), Formula (Ib), or Formula (Ic):

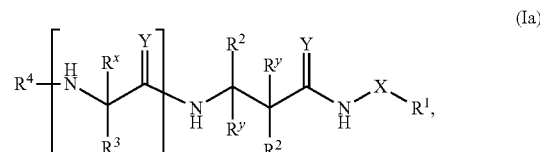

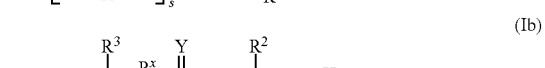

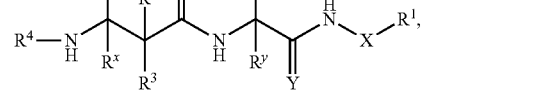

where the substituents $R^1$-$R^4$, $R^x$, $R^y$, X, Y, and s are as defined herein.

These compounds are used in the treatment of cancer, immunologic disorders, autoimmune disorders, neurodegenerative disorders, or inflammatory disorders or for providing immunosuppression for transplanted organs or tissues.

10 Claims, 1 Drawing Sheet

Related U.S. Application Data

(60) Provisional application No. 62/038,636, filed on Aug. 18, 2014.

(51) Int. Cl.

| | | |
|---|---|---|
| *C07C 311/19* | (2006.01) | |
| *C07C 237/06* | (2006.01) | |
| *C07D 261/18* | (2006.01) | |
| *C07C 237/12* | (2006.01) | |
| *C07C 237/22* | (2006.01) | |
| *C07D 209/18* | (2006.01) | |
| *C07C 311/14* | (2006.01) | |
| *A61K 31/165* | (2006.01) | |
| *A61K 31/42* | (2006.01) | |
| *A61K 38/02* | (2006.01) | |
| *C07K 5/06* | (2006.01) | |

(52) U.S. Cl.
CPC .......... *C07C 311/19* (2013.01); *C07D 209/18* (2013.01); *C07D 261/18* (2013.01); *C07K 5/06* (2013.01); *C07C 2601/02* (2017.05)

(56) References Cited

U.S. PATENT DOCUMENTS

| | | |
|---|---|---|
| 8,367,668 B2 | 2/2013 | Stieber et al. |
| 9,988,421 B2 | 6/2018 | Lin et al. |
| 2005/0171146 A1 | 8/2005 | Weber et al. |
| 2006/0241056 A1 | 10/2006 | Orlowski et al. |
| 2007/0010515 A1 | 1/2007 | Masuda et al. |
| 2007/0244153 A1 | 10/2007 | Kakimoto et al. |
| 2009/0227601 A1 | 9/2009 | Zhu et al. |
| 2010/0249197 A1 | 9/2010 | Watkins et al. |
| 2010/0249400 A1 | 9/2010 | Shiina |
| 2013/0053303 A1 | 2/2013 | Shenk et al. |
| 2013/0072422 A1 | 3/2013 | Shenk et al. |
| 2014/0315786 A1 | 10/2014 | Jirousek et al. |
| 2018/0282317 A1 | 10/2018 | Lin et al. |
| 2020/0317729 A1 | 10/2020 | Lin et al. |

FOREIGN PATENT DOCUMENTS

| | | |
|---|---|---|
| CN | 102807601 A | 12/2012 |
| JP | 2006-298785 A | 11/2006 |
| JP | 2008-512476 A | 4/2008 |
| JP | 2014-91731 A | 5/2014 |
| JP | 2014-167005 A | 9/2014 |
| WO | 98/29387 A1 | 7/1998 |
| WO | 2006/009134 A1 | 1/2006 |
| WO | 2006/029210 A2 | 3/2006 |
| WO | 2006/065826 A2 | 6/2006 |
| WO | 2006/099261 A2 | 9/2006 |
| WO | 2007/083394 A1 | 7/2007 |
| WO | 2007/149512 A2 | 12/2007 |
| WO | 2009/051581 A1 | 4/2009 |
| WO | 2010/036357 A1 | 4/2010 |
| WO | 2010/038200 A1 | 4/2010 |
| WO | 2011/123502 A1 | 10/2011 |
| WO | 2012/065891 A1 | 5/2012 |
| WO | 2012/116440 A1 | 9/2012 |
| WO | 2013/005045 A1 | 1/2013 |
| WO | 2013/092979 A1 | 6/2013 |
| WO | 2014/095773 A1 | 6/2014 |
| WO | 2015/076359 A1 | 5/2015 |
| WO | 2015/106200 A2 | 7/2015 |
| WO | 2017/066763 A1 | 4/2017 |
| WO | 2019/075252 A1 | 4/2019 |

OTHER PUBLICATIONS

Hook et al. "The Proteolytic Stability of 'Designed' B-Peptides Containing a-Peptide-Bond Mimics and of Mixed a,b-Peptides: Application to Construction of MHC-Binding Peptides" Chemistry & Biodiversity 2:591-632 (Year: 2005).*
Vippagunta et al. "Crystalline Solids" Advanced Drug Delivery Reviews 48:3-26. (Year: 2001).*
Beaumont et al. "Design of Ester Prodrugs to Enhance Oral Absorption of Poorly Permeable Compounds: Challenges to the Discovery Scientist" Curr. Drug Metab. 4:461-485. (Year: 2003).*
Ettmayer et al. "Lessons Learned from Marketed and Investigational Prodrugs" J. Med. Chem. 47:2393-2404. (Year: 2004).*
Han H "Targeted Prodrug Design to Optimize Drug Delivery" AAPS Pharmsci 2:1-11 (Year: 2000).*
Muller C "Prodrug Approaches for Enhancing the Bioavailability of Drugs with Low Solubility" Chemistry & Biodiversity 6:2071-2083. (Year: 2009).*
Singh et al. "Recent Trends in Targeted Anticancer Prodrug and Conjugate Design" Curr. Med. Chem. 15:1802-1826. (Year: 2008).*
Testa B "Prodrug research: futile or failure?" Biochemical Pharmacology 68:2097-2106. (Year: 2004).*
Allen et al., "Analysis of the Cytosolic Proteome in a Cell Culture Model of Familial Amyotrophic Lateral Sclerosis Reveals Alterations to the Proteasome, Antioxidant Defenses, and Nitric Oxide Synthetic Pathways," J. Biol. Chem. 278:6371-6383 (2003).
Basler et al., "Inhibition of the Immunoproteasome Ameliorates Experimental Autoimmune Encephalomyelitis," EMBO Mol. Med. 6:226-238 (2014).
Baumeister et al., "The Proteasome: Paradigm of a Self-Compartmentalizing Protease," Cell 92:367-380 (1998).
Bedford et al., "Ubiquitin-Like Protein Conjugation and the Ubiquitin-Proteasome System as Drug Targets," Nat. Rev. Drug Discov. 10:29-46 (2011).
Bontscho et al., "Myeloperoxidase-Specific Plasma Cell Depletion by Bortezomib Protects From Anti-Neutrophil Cytoplasmic Autoantibodies-Induced Glomerulonephritis," J. Am. Soc. Nephrol. 22:336-348 (2011).
Brun, "Proteasome Inhibition as a Novel Therapy in Treating Rheumatoid Arthritis," Med. Hypotheses 71:65-72 (2008).
Egerer et al., "Tissue-Specific Up-Regulation of the Proteasome Subunit beta5i (LMP7) in Sjogren's Syndrome," Arthritis Rheum. 54:1501-1508 (2006).
El-Hashim et al., "Effect of Inhibition of the Ubiquitin-Proteasome-System and IkappaB Kinase on Airway Inflammation and Hyper-responsiveness in a Murine Model of Asthma," Int. J. Immunopathol. Pharmacol. 24:33-42 (2011).
Elliott et al., "Proteasome Inhibition: A Novel Mechanism to Combat Asthma," J. Allergy Clin. Immunol. 104:294-300 (1999).
Goldberg, "Functions of the Proteasome: From Protein Degradation and Immune Surveillance to Cancer Therapy," Biochem. Soc. Trans. 35:12-17 (2007).
Guillaume et al., "Two Abundant Proteasome Subtypes That Uniquely Process Some Antigens Presented by HLA Class I Molecules," Proc. Natl. Acad. Sci. U.S.A. 107:18599-18604 (2010).
Henry et al., "Proteolytic Activity and Expression of the 20S Proteasome are Increased in Psoriasis Lesional Skin," Br. J. Dermatol. 165:311-320 (2011).
Hirai, et al., "Bortezomib Suppresses Function and Survival of Plasmacytoid Dendritic Cells by Targeting Intracellular Trafficking of Toll-Like Receptorsand Endoplasmic Reticulum Homeostasis," Blood 117:500-509 (2011).
Huber et al., "Immuno and Constitutive Proteasome Crystal Structures Reveal Differences in Substrate and Inhibitor Specificity," Cell 148:727-738 (2012).
Huber et al., "Inhibitors for the Immuno and Constitutive Proteasome: Current and Future Trends in Drug Development," Angew Chem. Int. Ed Engl. 51:8708-8720 (2012).
Ichikawa et al., "Novel Proteasome Inhibitors Have a Beneficial Effect of Novel Proteasome Inhibitors in Murine Lupus via Dual Inhibition of Type I Interferon and Autoantibody-Secreting Cells," Arthritis Rheum. 64:493-503 (2012).
Inoue et al., "The Effect of Proteasome Inhibitor MG132 on Experimental Inflammatory Bowel Disease," Clin. Exp. Immunol. 156:172-82 (2009).

(56) References Cited

OTHER PUBLICATIONS

Kincaid et al., "Mice Completely Lacking Immunoproteasomes Show Major Changes in Antigen Presentation," Nat. Immunol. 13:129-135 (2012).
Lang et al., "The Early Marginal Zone B Cell-Initiated T-Independent Type 2 Response Resists the Proteasome Inhibitor Bortezomib," J. Immunol. 185:5637-5647 (2010).
Liang et al., "Proteasome Inhibition in Transplantation-Focusing on the Experience with Bortezomib," Curr. Pharm. Design 19:3299-3304 (2013).
Meng et al., "Epoxomicin, a Potent and Selective Proteasome Inhibitor, Exhibits in Vivo Antiinflammatory Activity," P. Natl. Acad. Sci U.S.A. 96:10403-10408 (1999).
Minagar et al., "Plasma Ubiquitin-Proteasome System Profile in Patients With Multiple Sclerosis: Correlation With Clinical Features, Neuroimaging, and Treatment With Interferon-Beta-1 b," Neurol. Res. 34:611-618 (2012).
Muchamuel et al., "A Selective Inhibitor of the Immunoproteasome Subunit LMP7 Blocks Cytokine Production and Attenuates Progression of Experimental Arthritis," Nat. Med. 15:781-787 (2009).
Neubert et al., "The Proteasome Inhibitor Bortezomib Depletes Plasma Cells and Protects Mice With Lupus-Like Disease From Nephritis," Nat. Med. 14:748-755 (2008).
Niewerth et al., "Anti-Leukemic Activity and Mechanisms Underlying Resistance to the Novel Immunoproteasome Inhibitor PR-924," Biochem. Pharmacol. 89:43-51 (2014).
Padrissa-Altes et al., "The use of a Reversible Proteasome Inhibitor in a Model of Reduced-Size Orthotopic Liver Transplantation in Rats," Exp Mol. Pathol. 93:99-110 (2012).
Perkins, "Integrating Cell-Signalling Pathways With NF-[kappa]B and IKK Function," Nat. Rev. Mol. Cell. Biol. 8:49-62 (2007).
Roccaro et al., "Selective Inhibition of Chymotrypsin-Like Activity of the Immunoproteasome and Constitutive Proteasome in Waldenstrom Macroglobulinemia," Blood 115:4051-4060 (2010).
Rock et al., "Proteases in MHC Class I Presentation and Cross-Presentation," J. Immunol. 184:9-15 (2010).
Rock et al., "Inhibitors of the Proteasome Block the Degradation of Most Cell Proteins and the Generation of Peptides Presented on MHC Class I Molecules," Cell 78:761-771 (1994).
Rock et al., "Protein Degradation and the Generation of MHC Class I-Presented Peptides," Adv. Immunol 80:1-70 (2002).
Schmidt et al., "Targeting the Proteasome: Partial Inhibition of the Proteasome by Bortezomib or Deletion of the Immunosubunit LMP7 Attenuates Experimental Colitis," Gut 59:896-906 (2010).
Singh et al., "PR-924, a Selective Inhibitor of the Immunoproteasome Subunit LMP-7, Blocks Multiple Myeloma Cell Growth Both in Vitro and in Vivo," Br. J. Haematol. 152:155-163 (2011).
Sureshkumar et al., "Proteasome Inhibition With Bortezomib: an Effective Therapy for Severe Antibody Mediated Rejection After Renal Transplantation," Clin. Nephrol. 77:246-253 (2012).
Van der Heijden et al., "The Proteasome Inhibitor Bortezomib Inhibits the Release of NFkappaB-Inducible Cytokines and Induces Apoptosis of Activated T Cells From Rheumatoid Arthritis Patients," Clin. Exp. Rheumatol. 27:92-98 (2009).
Verbrugge et al., "Inactivating PSMB5 Mutations and P-glycoprotein (Multidrug Resistance-Associated Protein/ATP-Binding Cassette B1) Mediate Resistance to Proteasome Inhibitors: ex Vivo Efficacy of (Immuno)Proteasome Inhibitors in Mononuclear Blood Cells From Patients With Rheumatoid Arthritis," J. Pharmacol. Exp. Ther. 341:174-182 (2012).
Zhang et al., "In Vitro and in Vivo Therapeutic Efficacy of Carfilzomib in Mantle Cell Lymphoma: Targeting the Immunoproteasome," Mol. Cancer Ther. 12:2494-2504 (2013).
Zollner et al., "Proteasome Inhibition Reduces Superantigen-Mediated T Cell Activation and the Severity of Psoriasis in a SCID-hu Model," J. Clin. Invest. 109:671-679(2002).
DFHBI Datasheet (Lucerna).
International Preliminary Report on Patentability for Application No. PCT/US2015/044876 (dated Feb. 21, 2017).
International Search Report and Written Opinion for corresponding Application No. PCT/US2015/044876 (dated Nov. 13, 2015).
Pubchem. SID 132358420.Jan. 24, 2012, pp. 1-6 [online], [retrieved on Oct. 1, 2015] Retrieved from the Internet <URL: http://pubchem.ncbl.nlm.nih.gov/substance/132358420>; p. 3, formula.
Pubchem. SID 132071324.Jan. 24, 2012, pp. 1-6 [online], [retrieved on Oct. 1, 2015], Retrieved from the Internet <URL: http://pubchem.ncbl.nlm.nih.gov/substance/132071324>; p. 3, formula.
Pubchem. SID 146191084. Oct. 10, 2012, pp. 1-6 [online]. [retrieved on Oct. 1, 2015]. Retrieved from the Internet <URL: http://pubchem.ncbl.nlm.nih.gov/substance/146191084>; p. 3, formula.
Pubchem. SID 144773390. Oct. 18, 2012, pp. 1-6 [online], [retrieved on Oct. 1, 2015]. Retrieved from the Internet <URL: http://pubchem.ncbl.nlm.nih.gov/substance/144773390>; p. 3, formula.
Supplementary European Search Report dated Mar. 27, 2018 for EP Application Serial No. 15834073.7.
Fuchise et al., "Atlantic Cod Trypsin-Catalyzed Peptide Synthesis with Inverse Substrates as Acyl Donor Components," Chem. Pharm. Bull. 58(4):484-487 (2010).
Translation of Notice of Reasons for Rejection for Japanese Patent Application No. 2017-509632 (Jun. 5, 2019).
Coumar et al., "3-[2-((2S)-2-Cyano-pyrrolidin-1-yl)-2-oxo-ethylamino]-3-methyl-butyramide Analogues as Selective DPP-IV Inhibitors for the Treatment of Type-ll Diabetes," Bioorg. Med. Chem. Lett. 17(5):1274-1279 (2007).
Drey et al., "Synthesis of β-Amino-Acid Peptides by Aminolysis of Substituted Di-hydro-1,3-oxazinones and Amino-Protected β-Lactams," J. Chem. Soc. Perkin 1 17:2001-2006 (1973).
Liotta et al., "Antibody-Catalyzed Rearrangement of a Peptide Bond: Mechanistic and Kinetic Investigations," J. Am. Chem. Soc. 117(17):4729-4741 (1995).
Examination Report for Indian Patent Application No. 201747005687 (dated Aug. 29, 2019).
Singh et al., "Immunoproteasome β5i-Selective Dipeptidomimetic Inhibitors," ChemPubSoc 11:1-6 (2016).
Lin et al., "N,C-Capped Dipeptides with Selectivity for Mycobacterial Proteasome Over Human Proteasomes: Role of S3 and S1 Binding Pockets," J. Am. Chem. Soc. 135(27):9968-9971 (2013).
El-Naggar et al., "Synthesis and Biological Activity of Some New 4-(Aminoacyl)Aminopyridines and 2-(Aminoacyl) Aminopyrimidine Derivatives," Polish Journal of Chemistry, 56:1279-1285 (1982).
Yamazaki et al., "Two New Tryptamine Derivatives, Leptoclinidamide and (-)-Leptoclinidamine B, from an Indonesian Ascidian Leptoclinides dubius," Marine Drugs, 10(12):349-357 (2012).
Examination report for Europe Patent Application No. 15834073.7 (dated Mar. 25, 2020).
Database Registry Database accession No. 1299989-71-1.
Database Registry Database accession No. 1276335-00-2.
Database Registry Database accession No. 1060993-03-4.
El-Naggar et al., "Database CA [Online]: 'Synthesis and Biological Activity of Some New 4-(Aminoacyl) Aminopyridines and 2-(Aminoacyl)Aminopyrimidine Derivatives,'" Polish Journal of Chemistry, 56:1279-1285 (1982).
Solomon et al., "Synthesis and Antimalarial Activity of Novel Side Chain Modified Antimalarial Agents Derived From 4-Aminoquinoline," Medicinal Chemistry, 4:446-456 (2008).
Office Action in Chinese Patent Application No. 201680065296.2 (dated Dec. 4, 2019).
Pubchem CID 91250924, https://pubchem.ncbi.nlm.nih.gov/compound/91250924, Retrieved Nov. 24, 2019.
International Search Report and Written Opinion for corresponding Application No. PCT/US2018/055482 (dated Feb. 8, 2019).
Pubchem CID 64894495, Oct. 23, 2012 (Accession date Nov. 29, 2018).
Pubchem CID 129847054, Sep. 13, 2017 (Accession date Jan. 18, 2019).
Office Action for U.S. Appl. No. 15/768,628 (dated May 1, 2020).
Office Action for U.S. Appl. No. 15/768,628 (dated Oct. 11, 2019).
Restriction Requirement for U.S. Appl. No. 15/110,000 (dated Mar. 6, 2017).
Office Action for U.S. Appl. No. 15/110,000 (dated Jun. 5, 2017).
U.S. Reissue U.S. Appl. No. 16/893,086, first named inventor Gang LIN, filed Jun. 4, 2020.

(56) References Cited

OTHER PUBLICATIONS

Office Action in Chinese Patent Application No. 201680065296.2 (dated Sep. 28, 2020).
Office Action in European Application No. 16856412.8 (dated Sep. 16, 2020).
Notice of Reasons for Rejection for Japanese Patent Application No. 2018-519271 (dated Oct. 22, 2020).
Korshin et al., "Aminoamidines. 7.* 2-(Arylaminomethyl)imidazolines and Their Acylated Derivatives," Izvestiya Akademii Nauk, Seriya Khimicheskaya 3:472-479 (1994) with English translation as Korshin et al., "Aminoamidines. 7.* 2-(Arylaminomethyl)imidazolines and Their Acylated Derivatives," Russ. Chem. Bull. 43(3):431-438 (1994).
Grudzinski et al., "Studia nad Procesami Uwodornienia Aminonitryli. IX. Otrzymywanie N,N'-Dwuacylo-Trojmetylenodwuamin o Niejednakowych Resztach Kwasowych w Czateczce [Studies on the Hydrogenation of Aminonitriles. IX. Synthesis of N,N'-Diacyl-trimethylenediamines Containing Different Acyl Residues]," Acta Poloniae Pharmaceutica 22(6):485-490 (1965) (Article in Polish, English Title and Summary at pp. 489-490).
Extended European Search Report and Opinion for European Application No. 16856412.8 dated Mar. 22, 2019.
CAS Registry No. 3641-55-2, Entered STN: Nov. 16, 1984.
CAS Registry No. 294889-15-9, Entered STN: Oct. 12, 2000.
CAS Registry No. 51219-75-1, Entered STN: Nov. 16, 1984.
CAS Registry No. 51219-69-3, Entered STN: Nov. 16, 1984.
CAS Registry No. 59973-55-6, Entered STN: Nov. 16, 1984.
Duke et al., "Synthesis and Biological Evaluation of Sparsomycin Analogues," J. Med. Chem. 26:1556-1561 (1983).
Baud et al., "Defining the Mechanism of Action and Enzymatic Selectivity of Psammaplin A against Its Epigenetic Targets," J. Med. Chem. 55:1731-1750 (2012).
CAS Registry No. 839730-13-1, Entered STN: Mar. 1, 2005.
CAS Registry No. 839730-22-2, Entered STN: Mar. 1, 2005.
CAS Registry No. 839730-21-1, Entered STN: Mar. 1, 2005.
CAS Registry No. 866779-17-1, Entered STN: Nov. 4, 2005.
CAS Registry No. 1461869-28-2, Entered STN: Oct. 21, 2013.
CAS Registry No. 50633-04-0, Entered STN: Nov. 16, 1984.
CAS Registry No. 87639-77-8, Entered STN: Nov. 16, 1984.
CAS Registry No. 120655-16-5, Entered STN: May 12, 1989.
Supplementary European Search Report for European Patent Application No. 15735399.6 (dated Jun. 29, 2017).
Lei et al., "Structural Features and Binding Free Energies for Non-Covalent Inhibitors Interacting with Immunoproteasome by Molecular Modeling and Dynamics Simulations," Theor. Chem. Acc. 131:1-11 (2012).
Blackbum et al., "Characterization of a new Series of Non-Covalent Proteasome Inhibitors with Exquisite Potency and Selectivity for the 20S Beta5-Subunit," Biochem. J. 430:461-476 (2010).
Siebler et al., "Molecular Mutil-Wavelength Optical Anion Sensors," Eur. J. Inorg. Chem. 523-527 (2010).
Ahlford et al., "Fine-Tuning Catalytic Activity and Selectivity-[Rh(Amino Acid Thioamide)] Complexes for Efficient Ketone Reduction," Tetrahedron Lett. 50:6321-6324 (2009).
Blackbum et al. "Optimization of a Series of Dipeptides with a P3 Beta-Neopentyl Asparagine Residue as Non-Covalent Inhibitors of the Chymotrypsin-Like Activity of the Human 20S Proteasome," Med. Chem. Commun. 3:710-719 (2012).
International Preliminary Report on Patentability and Written Opinion for PCT/US2015/011022 (dated Jul. 21, 2016).
International Search Report and Written Opinion for corresponding Application No. PCT/US2015/011022 (dated Jun. 24, 2015).

PUBCHEM: Compound Summary for CID 269632 (Mar. 26, 2005).
Office Action for European Patent Application No. 15735399.6 (dated Jun. 11, 2018).
Pubchem. CID 17857389.Dec. 4, 2007, pp. 1-13[online], [retrieved on Feb. 27, 2017] Retrieved from the Internet <URL: https://pubchem.ncbi.nlm.nih.gov/compound/17857389; p. 4, formula.
PCT International Search Report and Written Opinion corresponding to PCT/US2016/057346, dated Mar. 23, 2017.
International Preliminary Report on Patentability for Application No. PCT/US2016/057346 (dated Apr. 17, 2018).
Translation of the Office Action for Chinese Patent Application No. 201580056519.4 (dated Jun. 29, 2020).
Restriction Requirement for U.S. Appl. No. 16/755,427 (dated Dec. 21, 2020).
Muchamuel et al., "A Selective Inhibitor of the Immunoproteasome Subunit LMP7 Blocks Cytokine Production and Attenuates Progression of Experimental Arthritis," Nature Medicine 15(7):781-787 (2009).
Basler et al., "Prevention of Experimental Colitis by a Selective Inhibitor of the Immunoproteasome," J. Immunol. 185:634-641 (2010).
Ichikawa et al., "Beneficial Effect of Novel Proteasome Inhibitors in Murine Lupus via Dual Inhibition of Type I Interferon and Autoantibody-Secreting Cells," Arthritis & Rheumatism 64(2):493-503 (2012).
Mutlu et al., "Proteasomal Inhibition After Injury Prevents Fibrosis by Modulating TGF-b1 Signalling," Thorax 67:139-146 (2012).
Mitsiades et al., "Proteasome Inhibition as a New Therapeutic Principle in Hematological Malignancies," Current Drug Targets 7:1341-1347 (2006).
Orlowski "The Ubiquitin Proteasome Pathway from Bench to Bedside," Hematology 220-225 (2005).
Fisher et al., "Multicenter Phase II Study of Bortezomib in Patients With Relapsed or Refractory Mantle Cell Lymphoma," J. Clin. Oncol. 24(30)4867-4874 (2006).
Walsh et al., "Proteasome Inhibitor-Based Primary Therapy for Antibody-Mediated Renal Allograft Rejection," Transplantation 89(3):277-284 (2010).
Mateos-Mazon et al., "Use of Bortezomib in the Management of Chronic Graft-Versus-Host Disease Among Multiple Myeloma Patients Relapsing After Allogeneic Transplantation," Haematologica 92(9):1295-1296 (2007).
Kloda, "Systemic Sclerosis—Bortezomib—is it Wonder Drug?," MEDtube.net (2011) https://medtube.net/tribune/systemic-sclerosis-bortezomib-is-it-wonder-drug/.
International Preliminary Report on Patentability for corresponding Application No. PCT/US2018/055482 (dated Apr. 14, 2020).
Office Action in Chinese Patent Application No. 201680065296.2 (dated Apr. 30, 2021).
Office Action for Chinese Patent Application No. 201580056519.4 (dated May 7, 2021).
Examination Report for Indian Patent Application No. 202048025018 (dated Jun. 3, 2021).
Partial Supplementary European Search Report for EP Application Serial No. 18867283.6 (dated Jun. 23, 2021).
O'Mahony et al., "A Practical Synthesis of 2'-Aminoacylamino-2'-Deoxyadenosines," Tetrahedron 63(29):6901-6908 (2007).
Kataoka et al., "Formation of Heterocyclic Amine-Amino Acid Adducts by Heating in a Model System," Food Chemistry 130(3):725-729 (2012).
Extended European Search Report for EP Application Serial No. 18867283.6 (dated Sep. 27, 2021).

* cited by examiner

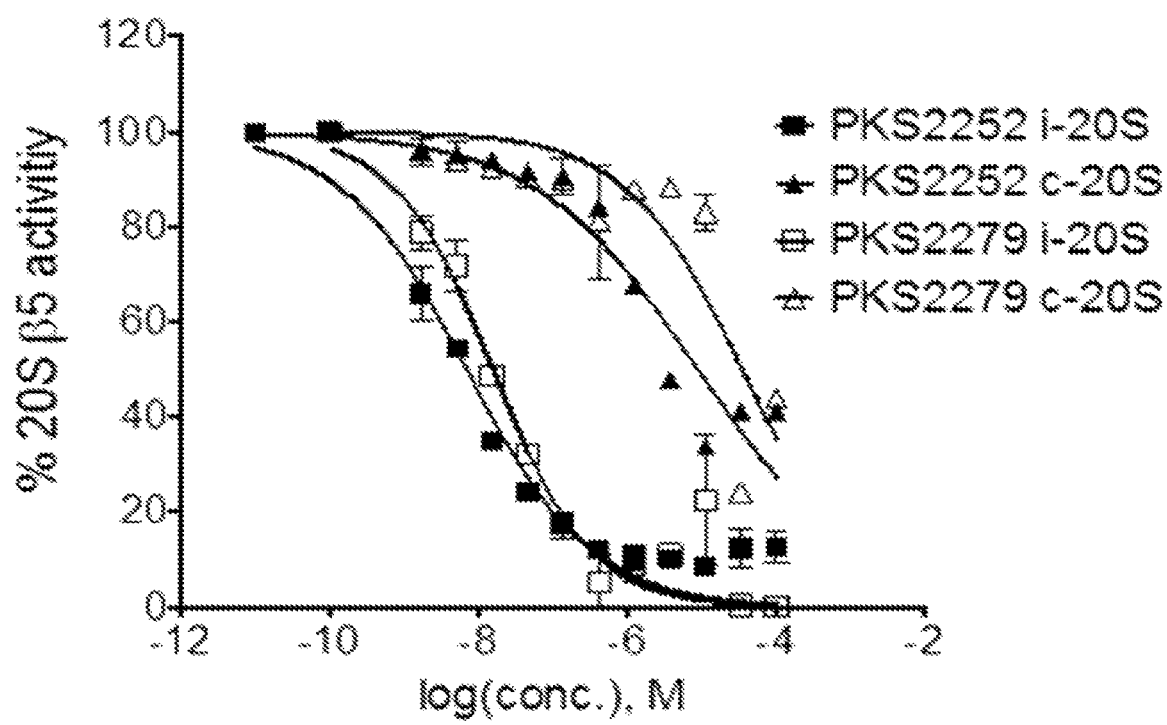

DIPEPTIDOMIMETICS AS INHIBITORS OF HUMAN IMMUNOPROTEASOMES

This invention was made with government support under 5R21 AI 01393 awarded by the National Institutes of Health. The government has certain rights in the invention.

This application is a national stage application under 35 U.S.C. § 371 of International Application No. PCT/US2015/044876, filed, Aug. 12, 2015, which claims the benefit of U.S. Provisional Patent Application Ser. No. 62/038,636, filed Aug. 18, 2014, which is hereby incorporated by reference in its entirety.

FIELD OF THE INVENTION

The present invention relates to inhibitors of human immunoproteasomes.

BACKGROUND OF THE INVENTION

The proteasome is a large, ATP-dependent, multi-subunit, barrel-shaped N-terminal nucleophile hydrolase present in the cytosol and nucleus of eukaryotic cells, and is responsible for the degradation of the majority of cellular proteins (Baumeister et ah, "The Proteasome: Paradigm of a Self-Compartmentalizing Protease," *Cell* 92:367-380 (1998); Goldberg, A. L., "Functions of the Proteasome: From Protein Degradation and Immune Surveillance to Cancer Therapy," *Biochemical Society Transactions* 35:12-17 (2007)). The proteasome not only controls many critical cellular checkpoints through degradation, but also generates peptides for antigen presentation (Goldberg, A. L., "Functions of the Proteasome: From Protein Degradation and Immune Surveillance to Cancer Therapy," *Biochemical Society Transactions* 35:12-17 (2007); Rock et al., "Inhibitors of the Proteasome Block the Degradation of Most Cell Proteins and the Generation of Peptides Presented on MHC Class I Molecules," *Cell* 78:761-771 (1994)). Highly specific proteasome inhibitors can markedly limit the overall supply of peptides for MHC class I molecules and thus block antigen presentation (Rock et al., "Protein Degradation and the Generation of MHC Class I-Presented Peptides," *Advances in Immunology* 80:1-70 (2002)). The constitutive proteasome core particle is called 20S (c-20S) because of its sedimentation properties. Inside the c-20S core reside two copies of each of three proteases with distinct specificities, β1 (caspase-like), β2 (tryptic-like) and β5 (chymotryptic-like) (Bedford et al., "Ubiquitin-Like Protein Conjugation and the Ubiquitin-Proteasome System as Drug Targets," *Nature Reviews. Drug Discovery* 10:29-46 (2011)). However, lymphocytes and cells that have responded to interferon-γ express a different proteasome, called the immunoproteasome (i-20S), in which the corresponding proteases are the products of different genes: β1i, β2i and β5i. Intermediate proteasomes that contain mixed β subunits are found in many cells, for example in the mucosa of the colon and small bowel (Guillaume et al., "Two Abundant Proteasome Subtypes that Uniquely Process Some Antigens Presented by HLA Class I Molecules," *Proc. Nat'l Acad. Sci. USA* 107:18599-18604 (2010)). The effects of replacement of constitutive subunits by immuno-β subunits include increased proteolytic activity and altered peptide preferences of the active sites (Rock et al., "Proteases in MHC Class I Presentation and Cross-Presentation," *Journal of Immunology* 184:9-15d (2010)). For example, the caspase-like β1 replacement, β1i, preferentially cleaves after small hydrophobic residues rather than after aspartate (Huber et al., "Immuno- and Constitutive Proteasome Crystal Structures Reveal Differences in Substrate and Inhibitor Specificity," *Cell* 148:727-738 (2012)). This results in altered peptide products, such that mice with combined deficiency of β1i, β2i, and β5i are viable, fertile and healthy but express a different antigenic peptide repertoire than wild type mice, as evidenced by their rejection of syngeneic wild type splenocytes (Kincaid et al., "Mice Completely Lacking Immunoproteasomes Show Major Changes in Antigen Presentation," *Nature Immunology* 13:129-135 (2012)). Hu C-20S and i-20S appear to regulate cytokine production through different pathways (Muchamuel et al., "A Selective Inhibitor of the Immunoproteasome Subunit LMP7 Blocks Cytokine Production and Attenuates Progression of Experimental Arthritis," *Nature Medicine* 15:781-787 (2009)). Hu c-20S controls the activation of NF-κB via the degradation of IκB, the binding partner of NF-κB in the cytosol (Perkins, N. D., "Integrating Cell-Signalling Pathways with NF-[Kappa]B and IKK Function," *Nat. Rev. Mol. Cell Biol.* 8:49-62 (2007)), and inhibition of C-20S blocks the activation of NF-κB (Meng et al., "Epoxomicin, a Potent and Selective Proteasome Inhibitor, Exhibits In Vivo Antiinflammatory Activity," *Proc. Nat'l Acad. Sci. USA* 96:10403-10408 (1999)). For its part, among other potential pathways, i-20S appears to control the co-translocation of TLR9 and Unc93B1, an endoplasmic reticulum (ER)-resident protein, to endosomes (Hirai et al., "Bortezomib Suppresses Function and Survival of Plasmacytoid Dendritic Cells by Targeting Intracellular Trafficking of Toll-Like Receptors and Endoplasmic Reticulum Homeostasis," *Blood* 117:500-509 (2011)). Proteasomes control diverse cellular functions, among them signal transduction for inflammatory cytokine release, antigen presentation, and the ability of plasma cells to secrete antibodies without dying from accumulation of misfolded immunoglobulins (Goldberg, A. L., "Functions of the Proteasome: From Protein Degradation and Immune Surveillance to Cancer Therapy," *Biochemical Society Transactions* 35:12-17 (2007); Bedford et al., "Ubiquitin-Like Protein Conjugation and the Ubiquitin-Protcasome System as Drug Targets," *Nature Reviews. Drug Discovery* 10:29-46 (2011); Neubert et al., "The Proteasome Inhibitor Bortezomib Depletes Plasma Cells and Protects Mice with Lupus-Like Disease from Nephritis," *Nature Medicine* 14:748-755 (2008)). Thus the proteasome could be a target for treating autoimmune and inflammatory diseases. For example, inhibition of the proteasome in plasmacytoid dendritic cells (pDCs) prevents the trafficking of TLRs, resulting in a block of nuclear translocation of IRF-7, consequently suppressing the production of IFNα (Hirai et al., "Bortezomib Suppresses Function and Survival of Plasmacytoid Dendritic Cells by Targeting Intracellular Trafficking of Toll-Like Receptors and Endoplasmic Reticulum Homeostasis," *Blood* 117:500-509 (2011)), a cytokine implicated in systemic lupus erythematosus (SLE). However, by the same token, widespread inhibition of proteasomes can be expected to be toxic and has proven toxic in the clinic.

Two proteasome inhibitors approved by the FDA for treatment of malignancy, Bortezomib and Carfilzomib, inhibit both the C-20S β5c and the i-20S β5i (Huber et al., "Inhibitors for the Immuno- and Constitutive Proteasome: Current and Future Trends in Drug Development," *Angewandte Chemie* 51:8708-8720 (2012)). Bortezomib, a dipeptidyl boronate, is a slow-binding, covalent but reversible inhibitor, whereas Carfilzomib is a peptide with an epoxyketone warhead that inhibits proteasomes irreversibly. In addition to treatment of malignancy, Bortezomib has been reported to be effective in inflammatory bowel disease (IBD), SLE, graft-versus-host disease, antibody-mediated graft rejection, rheumatoid arthritis (RA), and other immunologic, autoimmune and/or inflammatory conditions. However, such a broad-spectrum inhibitor is too toxic for chronic treatment of non-malignant diseases. ONX 0914, another peptide epoxyketone, has modest selectivity for i-20S β5i (Muchamuel et al., "A Selective Inhibitor of the Immunoproteasome Subunit LMP7 Blocks Cytokine Production and Attenuates Progression of Experimental Arthritis," *Nature Medicine* 15:781-787 (2009)) and is reported to have efficacy in rheumatoid arthritis (Muchamuel et al., "A Selective Inhibitor of the Immunoproteasome Subunit LMP7 Blocks Cytokine Production and Attenuates Progression of Experimental Arthritis," *Nature Medicine* 15:781-787 (2009)), SLE (Ichikawa et al., "Beneficial Effect of Novel Proteasome Inhibitors in Murine Lupus Via Dual Inhibition of Type I Interferon and Autoantibody-Secreting Cells," *Arthritis and Rheumatism* 64:493-503 (2012)), experimental colitis (Basler et al., "Prevention of Experimental Colitis by a Selective Inhibitor of the Immunoproteasome," *Journal of Immunology* 185:634-641 (2010)), and multiple sclerosis (Basler et al., "Inhibition of the immunoproteasome ameliorates experimental autoimmune encephalomyelitis," *EMBO Mol. Med.* 6:226-238 (2014)). Nonetheless, it, too, acts irreversibly and has considerable toxicity.

The present invention is directed to overcoming these and other deficiencies in the art.

SUMMARY OF THE INVENTION

One aspect of the present invention relates to a compound of Formula (I):

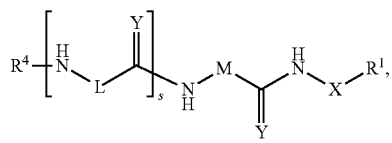

wherein
L is —(CR$^3$R$^x$)$_p$—;
M is —(CR$^2$R$^y$)$_r$—;
R$^1$ is selected from the group consisting of monocyclic and bicyclic aryl, biphenyl, monocyclic and bicyclic heteroaryl, monocyclic and bicyclic heterocyclyl, and monocyclic and bicyclic non-aromatic heterocycle, wherein monocyclic and bicyclic aryl, biphenyl, monocyclic and bicyclic heteroaryl, monocyclic and bicyclic heterocyclyl, and monocyclic and bicyclic non-aromatic heterocycle can be optionally substituted from 1 to 3 times with a substituent selected independently at each occurrence thereof from the group consisting of halogen, cyano, —CF$_3$, C$_{1-6}$ alkyl, and C$_{1-6}$ alkoxy;
R$^2$ is independently selected at each occurrence thereof from the group consisting of H, D, C$_{1-6}$ alkyl, —CH$_2$OC$_{1-6}$ alkyl, —CH$_2$Ar, and —CH$_2$heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;
R$^3$ is independently selected at each occurrence thereof from the group consisting of H, D, —CH$_2$OC$_{1-6}$ alkyl, —(CH$_2$)$_m$C(O)NHR$^5$, —(CH$_2$)$_m$C(O)NR$^6$R$^7$, —(CH$_2$)$_m$C(O)OH, and —(CH$_2$)$_m$C(O)OBn;

R$^4$ is selected from the group consisting of H, —C(O)(CH$_2$)$_n$Ph, —C(O)CH$_2$NR$^6$R$^7$, —SO$_2$Ar, —SO$_2$C$_{1-6}$ alkyl, —SO$_2$C$_{3-6}$ cycloalkyl, —C(O)(CH$_2$)$_n$Het, —C(O)C(O)Het, —C(O)C$_{1-6}$ alkyl, —C(O)OC$_{1-6}$ alkyl, —C(O)CF$_3$, heteroaryl, and —(CH$_2$)$_n$NR$^6$R$^7$, wherein aryl (Ar) and heteroaryl (Het) can be optionally substituted from 1 to 3 times with a substituent selected independently at each occurrence thereof from the group consisting of halogen, cyano, C$_{1-6}$ alkyl, and C$_{1-6}$ alkoxy;
R$^5$ is selected from the group consisting of C$_{1-6}$ alkyl, C$_{1-6}$ alkoxy, non-aromatic heterocycle, —NR$^6$R$^7$, and —CR$^8$R$^9$;
R$^6$, R$^7$, R$^8$, and R$^9$ are each independently selected from the group consisting of H, D, C$_{1-6}$ alkyl, and —(CH$_2$)$_k$OH;
or R$^6$ and R$^7$ are taken together with the nitrogen to which they are attached to form a morpholine ring;
or R$^8$ and R$^9$ are taken together with the carbon to which they are attached to form an oxetane ring;
R$^x$ is independently selected at each occurrence thereof from the group consisting of H, D, —CH$_2$OC$_{1-6}$ alkyl, —(CH$_2$)$_m$C(O)NHR$^5$, —(CH$_2$)$_m$C(O)NR$^6$R$^7$, and —CH$_2$C(O)R$^5$;
R$^y$ is independently selected at each occurrence thereof from the group consisting of H, D, C$_{1-6}$ alkyl, —CH$_2$OC$_{1-6}$ alkyl, —CH$_2$Ar, and —CH$_2$ heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;
X is —(CH$_2$)$_q$—, —O—, or —(CD$_2$)$_q$-;
Y is O or S;
k is 1, 2, or 3;
m is 0, 1, 2, 3, 4, or 5;
n is 0, 1, 2, or 3;
p is 1 or 2;
q is 0, 1, or 2;
r is 1 or 2; and
s is 0 or 1;
with a proviso that when s is 0, then r is 2; and when s is 1, then r+p≥3,
or an oxide thereof, a pharmaceutically acceptable salt thereof, a solvate thereof, or a prodrug thereof.

Another aspect of the present invention relates to a method of treating cancer, immunologic disorders, autoimmune disorders, neurodegenerative disorders, or inflammatory disorders in a subject or for providing immunosuppression for transplanted organs or tissues in a subject. This method includes administering to the subject in need thereof a compound of the Formula (I):

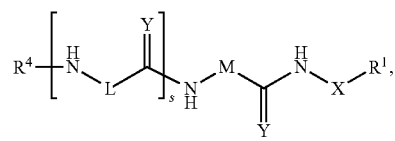

wherein
L is —(CR$^3$R$^x$)$_p$—;
M is —(CR$^2$R$^y$)$_r$—;
R$^1$ is selected from the group consisting of monocyclic and bicyclic aryl, biphenyl, monocyclic and bicyclic heteroaryl, monocyclic and bicyclic heterocyclyl, and monocyclic and bicyclic non-aromatic heterocycle, wherein monocyclic and bicyclic aryl, biphenyl, monocyclic and bicyclic heteroaryl, monocyclic and bicyclic heterocyclyl, and monocyclic and bicyclic non-aromatic heterocycle can be optionally substituted from 1 to 3 times with a substituent selected independently at each occurrence thereof from the group consisting of halogen, cyano, —CF$_3$, C$_{1-6}$ alkyl, and C$_{1-6}$ alkoxy;

R$^2$ is independently selected at each occurrence thereof from the group consisting of Fl, D, C$_6$ alkyl, —CH$_2$OC$_{1-6}$ alkyl, —CH$_2$Ar, and —CH$_2$heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;

R$^3$ is independently selected at each occurrence thereof from the group consisting of H, D, —CH$_2$OC$_{1-6}$ alkyl, —(CH$_2$)$_m$C(O)NHR$^5$, —(CH$_2$)$_m$C(O)NR$^6$R$^7$, —(CH$_2$)$_m$C(O)OH, and —(CH$_2$)$_m$C(O)OBn;

R$^4$ is selected from the group consisting of H, —C(O)(CH$_2$)$_n$Ph, —C(O)CH$_2$NR$^6$R$^7$, —SO$_2$Ar, —SO$_2$C$_{1-6}$ alkyl, —SO$_2$C$_{3-6}$ cycloalkyl, —C(O)(CH$_2$)$_n$Het, —C(O)C(O)Het, —C(O)C$_{1-6}$ alkyl, —C(O)OC$_{1-6}$ alkyl, —C(O)CF$_3$, heteroaryl, and —(CH$_2$)$_n$NR$^6$R$^7$, wherein aryl (Ar) and heteroaryl (Het) can be optionally substituted from 1 to 3 times with a substituent selected independently at each occurrence thereof from the group consisting of halogen, cyano, C$_{1-6}$ alkyl, and C$_{1-6}$ alkoxy;

R$^5$ is selected from the group consisting of C$_{1-6}$ alkyl, C$_{1-6}$ alkoxy, non-aromatic heterocycle, —NR$^6$R$^7$, and —CR$^8$R$^9$;

R$^6$, R$^7$, R$^8$, and R$^9$ are each independently selected from the group consisting of H, D, C$_{1-6}$ alkyl, and —(CH$_2$)$_k$OH;

or R$^6$ and R$^7$ are taken together with the nitrogen to which they are attached to form a morpholine ring;

or R$^8$ and R$^9$ are taken together with the carbon to which they are attached to form an oxetane ring;

R$^x$ is independently selected at each occurrence thereof from the group consisting of H, D, —CH$_2$OC$_{1-6}$ alkyl, —(CH$_2$)$_m$C(O)NHR$^5$, —(CH$_2$)$_m$C(O)NR$^6$R$^7$, and —CH$_2$C(O)R$^5$;

R$^y$ is independently selected at each occurrence thereof from the group consisting of H, D, C$_{1-6}$ alkyl, —CH$_2$OC$_{1-6}$ alkyl, —CH$_2$Ar, and —CH$_2$heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;

X is —(CH$_2$)$_q$—, —O—, or —(CD$_2$)$_q$-;
Y is O or S;
k is 1, 2, or 3;
m is 0, 1, 2, 3, 4, or 5;
n is 0, 1, 2, or 3;
p is 1 or 2;
q is 0, 1, or 2;
r is 1 or 2; and
s is 0 or 1;
with a proviso that when s is 0, then r is 2; and when s is 1, then r+p≥3.

Another aspect of the present invention relates to a compound of Formula (Ia), Formula (Ib), or Formula (Ic):

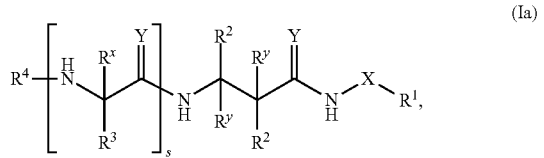

(Ia)

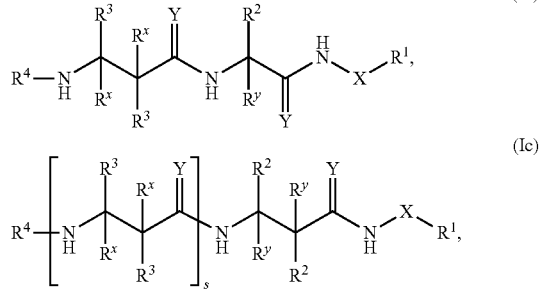

(Ib)

(Ic)

wherein

R$^1$ is selected from the group consisting of monocyclic and bicyclic aryl, biphenyl, monocyclic and bicyclic heteroaryl, monocyclic and bicyclic heterocyclyl, and monocyclic and bicyclic non-aromatic heterocycle, wherein monocyclic and bicyclic aryl, biphenyl, monocyclic and bicyclic heteroaryl, monocyclic and bicyclic heterocyclyl, and monocyclic and bicyclic non-aromatic heterocycle can be optionally substituted from 1 to 3 times with a substituent selected independently at each occurrence thereof from the group consisting of halogen, cyano, —CF$_3$, C$_{1-6}$ alkyl, and C$_{1-6}$ alkoxy;

R$^2$ is independently selected at each occurrence thereof from the group consisting of H, D, C$_{1-6}$ alkyl, —CH$_2$OC$_{1-6}$ alkyl, —CH$_2$Ar, and —CH$_2$heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;

R$^3$ is independently selected at each occurrence thereof from the group consisting of H, D, —CH$_2$OC$_{1-6}$ alkyl, —(CH$_2$)$_m$C(O)NHR$^5$, and —(CH$_2$)$_m$C(O)NR$^6$R$^7$;

R$^4$ is selected from the group consisting of —C(O)(CH$_2$)$_n$Ph, —C(O)CH$_2$NR$^6$R$^7$, —SO$_2$Ar, —SO$_2$C$_{1-6}$ alkyl, —SO$_2$C$_{3-6}$ cycloalkyl, —C(O)(CH$_2$)$_n$Het, —C(O)C(O)Het, —C(O)C$_{1-6}$ alkyl, —C(O)OC$_{1-6}$ alkyl, —C(O)CF$_3$, heteroaryl, and —(CH$_2$)$_n$NR$^6$R$^7$, wherein aryl (Ar) and heteroaryl (Het) can be optionally substituted from 1 to 3 times with a substituent selected independently at each occurrence thereof from the group consisting of halogen, cyano, C$_{1-6}$ alkyl, and C$_{1-6}$ alkoxy;

R$^5$ is selected from the group consisting of C$_{1-6}$ alkyl, C$_{1-6}$ alkoxy, non-aromatic heterocycle, —NR$^6$R$^7$, and —CR$^8$R$^9$;

R$^6$, R$^7$, R$^8$, and R$^9$ are each independently selected from the group consisting of H, D, C$_{1-6}$ alkyl, and —(CH$_2$)$_k$OH;

or R$^6$ and R$^7$ are taken together with the nitrogen to which they are attached to form a morpholine ring;

or R$^8$ and R$^9$ are taken together with the carbon to which they are attached to form an oxetane ring;

R$^x$ is independently selected at each occurrence thereof from the group consisting of H, D, —CH$_2$OC$_{1-6}$ alkyl, —(CH$_2$)$_m$C(O)NHR$^5$, —(CH$_2$)$_m$C(O)NR$^6$R$^7$, and —CH$_2$C(O)R$^5$;

R$^y$ is independently selected at each occurrence thereof from the group consisting of H, D, C$_{1-6}$ alkyl, —CH$_2$OC$_{1-6}$ alkyl, —CH$_2$Ar, and —CH$_2$heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;

X is —(CH$_2$)$_q$—, —O—, or —(CD$_2$)$_q$-;
Y is O or S;

k is 1, 2, or 3;
m is 0, 1, 2, 3, 4, or 5;
n is 0, 1, 2, or 3;
q is 0, 1, or 2; and
s is 0 or 1;
or an oxide thereof, a pharmaceutically acceptable salt thereof, a solvate thereof, or a prodrug thereof.

Yet another aspect of the present invention relates to a method of treating cancer, immunologic disorders, autoimmune disorders, neurodegenerative disorders, or inflammatory disorders in a subject or for providing immunosuppression for transplanted organs or tissues in a subject. This method includes administering to the subject in need thereof a compound of the Formula (Ia), Formula (Ib), or Formula (Ic):

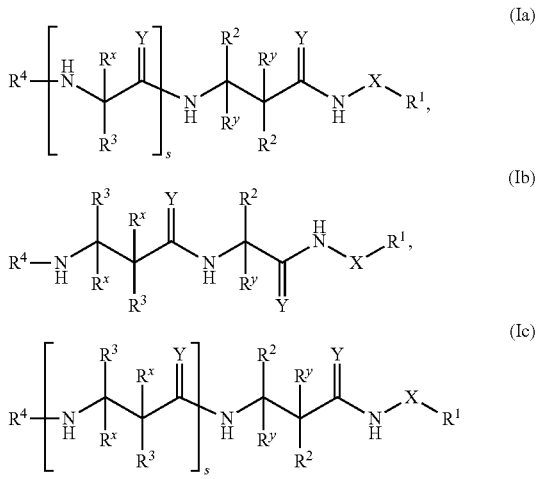

wherein $R^1$ is selected from the group consisting of monocyclic and bicyclic aryl, biphenyl, monocyclic and bicyclic heteroaryl, monocyclic and bicyclic heterocyclyl, and monocyclic and bicyclic non-aromatic heterocycle, wherein monocyclic and bicyclic aryl, biphenyl, monocyclic and bicyclic heteroaryl, monocyclic and bicyclic heterocyclyl, and monocyclic and bicyclic non-aromatic heterocycle can be optionally substituted from 1 to 3 times with a substituent selected independently at each occurrence thereof from the group consisting of halogen, cyano, —$CF_3$, $C_{1-6}$ alkyl, and $C_{1-6}$ alkoxy;

$R^2$ is independently selected at each occurrence thereof from the group consisting of H, D, $C_{1-6}$ alkyl, —$CH_2OC_{1-6}$ alkyl, —$CH_2Ar$, and —$CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

$R^3$ is independently selected at each occurrence thereof from the group consisting of H, D, —$CH_2OC_{1-6}$ alkyl, —$(CH_2)_mC(O)NHR^5$, and —$(CH_2)_mC(O)NR^6R^7$;

$R^4$ is selected from the group consisting of —C(O)$(CH_2)_n$Ph, —C(O)$CH_2NR^6R^7$, —$SO_2Ar$, —$SO_2C_{1-6}$ alkyl, —$SO_2C_{3-6}$ cycloalkyl, —C(O)$(CH_2)_n$Het, —C(O)C(O)Het, —C(O)$C_{1-6}$ alkyl, —C(O)O$C_{1-6}$ alkyl, —C(O)$CF_3$, heteroaryl, and —$(CH_2)_nNR^6R^7$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ alkoxy;

$R^5$ is selected from the group consisting of $C_{1-6}$ alkyl, $C_{1-6}$ alkoxy, non-aromatic heterocycle, —$NR^6R^7$, and —$CR^8R^9$;

$R^6$, $R^7$, $R^8$, and $R^9$ are each independently selected from the group consisting of H, D, $C_{1-6}$ alkyl, and —$(CH_2)_kOH$;

or $R^6$ and $R^7$ are taken together with the nitrogen to which they are attached to form a morpholine ring;

or $R^8$ and $R^9$ are taken together with the carbon to which they are attached to form an oxetane ring;

$R^x$ is independently selected at each occurrence thereof from the group consisting of H, D, —$CH_2OC_{1-6}$ alkyl, —$(CH_2)_mC(O)NHR^5$, —$(CH_2)_mC(O)NR^6R^7$, and —$CH_2C(O)R^5$;

$R^y$ is independently selected at each occurrence thereof from the group consisting of H, D, $C_{1-6}$ alkyl, —$CH_2OC_{1-6}$ alkyl, —$CH_2Ar$, and —$CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

X is —$(CH_2)_q$—, —O—, or —$(CD_2)_q$-;
Y is O or S;
k is 1, 2, or 3;
m is 0, 1, 2, 3, 4, or 5;
n is 0, 1, 2, or 3;
q is 0, 1, or 2; and
s is 0 or 1.

Selective inhibition of the i-20S is believed to impact the immune system but would otherwise be far less toxic than combined inhibition of both constitutive and immunoproteasomes. Here are presented inhibitors that act both with high selectivity and full reversibility on hu i-20S β5i over hu C-20S. Inhibitors that are selective for the i-20S β5 i are expected to be equally if not more efficacious in treating autoimmune disease, with less toxicity. These inhibitors could open a new path to the treatment of immunologic, autoimmune, inflammatory, neurodegenerative, and certain neoplastic disorders such as: systemic lupus erythematosus, chronic rheumatoid arthritis, inflammatory bowel disease, ulcerative colitis, Crohn's disease, multiple sclerosis, amyotrophic lateral sclerosis (ALS), atherosclerosis, scleroderma, systemic sclerosis, autoimmune hepatitis, Sjogren Syndrome, lupus nephritis, glomerulonephritis, rheumatoid arthritis, psoriasis, Myasthenia Gravis, Imunoglobuline A nephropathy, atherosclerosis, vasculitis, renal fibrosis, lung fibrosis, liver fibrosis, transplant rejection, idiopathic pulmonary fibrosis, asthma, and inflammation driven cancers such as: triple negative breast cancers.

BRIEF DESCRIPTION OF THE DRAWINGS

FIG. 1 is a graph showing inhibition of human i-20S β5i and c-20S β5c by selected dipeptidomimetics.

DETAILED DESCRIPTION OF THE INVENTION

One aspect of the present invention relates to a compound of Formula (I):

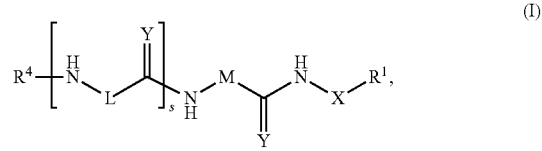

wherein

L is —(CR$^3$R$^x$)$_p$—;

M is —(CR$^2$R$^y$)$_r$—;

R$^1$ is selected from the group consisting of monocyclic and bicyclic aryl, biphenyl, monocyclic and bicyclic heteroaryl, monocyclic and bicyclic heterocyclyl, and monocyclic and bicyclic non-aromatic heterocycle, wherein monocyclic and bicyclic aryl, biphenyl, monocyclic and bicyclic heteroaryl, monocyclic and bicyclic heterocyclyl, and monocyclic and bicyclic non-aromatic heterocycle can be optionally substituted from 1 to 3 times with a substituent selected independently at each occurrence thereof from the group consisting of halogen, cyano, —CF$_3$, C$_{1-6}$ alkyl, and C$_{1-6}$ alkoxy;

R$^2$ is independently selected at each occurrence thereof from the group consisting of H, D, C$_{1-6}$ alkyl, —CH$_2$OC$_{1-6}$ alkyl, —CH$_2$Ar, and —CH$_2$heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;

R$^3$ is independently selected at each occurrence thereof from the group consisting of H, D, —CH$_2$OC$_{1-6}$ alkyl, —(CH$_2$)$_m$C(O)NHR$^5$, —(CH$_2$)$_m$C(O)NR$^6$R$^7$, —(CH$_2$)$_m$C(O)OH, and —(CH$_2$)$_m$C(O)OBn;

R$^4$ is selected from the group consisting of H, —C(O)(CH$_2$)$_n$Ph, —C(O)CH$_2$NR$^6$R$^7$, —SO$_2$Ar, —SO$_2$C$_{1-6}$ alkyl, —SO$_2$C$_{3-6}$ cycloalkyl, —C(O)(CH$_2$)$_n$Het, —C(O)C(O)Het, —C(O)C$_{1-6}$ alkyl, —C(O)OC$_{1-6}$ alkyl, —C(O)CF$_3$, heteroaryl, and —(CH$_2$)$_n$NR$^6$R$^7$, wherein aryl (Ar) and heteroaryl (Het) can be optionally substituted from 1 to 3 times with a substituent selected independently at each occurrence thereof from the group consisting of halogen, cyano, C$_{1-6}$ alkyl, and C$_{1-6}$ alkoxy;

R$^5$ is selected from the group consisting of C$_{1-6}$ alkyl, C$_{1-6}$ alkoxy, non-aromatic heterocycle, —NR$^6$R$^7$, and —CR$^8$R$^9$;

R$^6$, R$^7$, R$^8$, and R$^9$ are each independently selected from the group consisting of H, D, C$_{1-6}$ alkyl, and —(CH$_2$)$_k$OH;

or R$^6$ and R$^7$ are taken together with the nitrogen to which they are attached to form a morpholine ring;

or R$^8$ and R$^9$ are taken together with the carbon to which they are attached to form an oxetane ring;

R$^x$ is independently selected at each occurrence thereof from the group consisting of H, D, —CH$_2$OC$_{1-6}$ alkyl, —(CH$_2$)$_m$C(O)NHR$^5$, —(CH$_2$)$_m$C(O)NR$^6$R$^7$, and —CH$_2$C(O)R$^5$;

R$^y$ is independently selected at each occurrence thereof from the group consisting of H, D, C$_{1-6}$ alkyl, —CH$_2$OC$_{1-6}$ alkyl, —CH$_2$Ar, and —CH$_2$heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;

X is —(CH$_2$)$_q$—, —O—, or —(CD$_2$)$_q$-;

Y is O or S;

k is 1, 2, or 3;

m is 0, 1, 2, 3, 4, or 5;

n is 0, 1, 2, or 3;

p is 1 or 2;

q is 0, 1, or 2;

r is 1 or 2; and s is 0 or 1;

with a proviso that when s is 0, then r is 2; and when s is 1, then r+p≥3, or an oxide thereof, a pharmaceutically acceptable salt thereof, a solvate thereof, or a prodrug thereof.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "cycloalkyl" means a non-aromatic mono- or multicyclic ring system of about 3 to about 7 carbon atoms, preferably of about 5 to about 7 carbon atoms. Exemplary monocyclic cycloalkyls include cyclopentyl, cyclohexyl, cycloheptyl, and the like.

The term "aryl" means an aromatic monocyclic or multicyclic ring system of 6 to about 14 carbon atoms, preferably of 6 to about 10 carbon atoms. Representative aryl groups include phenyl and naphthyl.

The term "heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxopyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocyclyl" or "heterocycle" refers to a stable 3- to 18-membered ring (radical) which consists of carbon atoms and from one to five heteroatoms selected from the group consisting of nitrogen, oxygen and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidinyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The term "non-aromatic heterocycle" means a non-aromatic monocyclic system containing 3 to 10 atoms, preferably 4 to about 7 carbon atoms, in which one or more of the atoms in the ring system is/are element(s) other than carbon, for example, nitrogen, oxygen, or sulfur. Representative non-aromatic heterocycle groups include pyrrolidinyl, 2-oxopyrrolidinyl, piperidinyl, 2-oxopiperidinyl, azepanyl, 2-oxoazepanyl, 2-oxooxazolidinyl, morpholino, 3-oxomorpholino, thiomorpholino, 1,1-dioxothiomorpholino, piperazinyl, tetrohydro-2H-oxazinyl, and the like.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups." Suitable groups for that purpose are discussed in standard textbooks in the field of chemistry, such as Greene, *Protective Groups in Organic Synthesis*, John Wiley & Sons, New York (1991), which is hereby incorporated by reference in its entirety.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

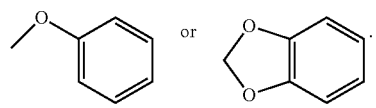

A compound with a hydroxy group drawn next to a nitrogen on a heterocycle can exist as the "keto" form. For example, 3-(2-hydroxy-[1,2,4]triazolo[1,5-a]pyridin-6-yl) propanoic acid can exist as 3-(2-oxo-2,3-dihydro-[1,2,4] triazolo[1,5-a]pyridin-6-yl)propanoic acid.

The term "halo" or "halogen" means fluoro, chloro, bromo, or iodo.

The term "substituted" or "substitution" of an atom means that one or more hydrogen on the designated atom is replaced with a selection from the indicated group, provided that the designated atom's normal valency is not exceeded.

"Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "method of treating" means amelioration or relief from the symptoms and/or effects associated with the disorders described herein. As used herein, reference to "treatment" of a patient is intended to include prophylaxis.

The term "compounds of the invention", and equivalent expressions, are meant to embrace compounds of general formula (I), formula (Ia), formula (Ib), and formula (Ic) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic, and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-β-toluoyltartrates, methane-sulphonates, ethanesulphonates, benzenesulphonates, p-toluenesulphonates, cyclohexylsulphamates and quinateslaurylsulphonate salts, and the like (see, for example, Berge et al., "Pharmaceutical Salts," *J. Pharm. Sci.,* 66:1-9 (1977) and Remington's Pharmaceutical Sciences, 17th ed., Mack Publishing Company, Easton, Pa., 1985, p. 1418, which are hereby incorporated by reference in their entirety). Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include, for example, sodium hydride, sodium hydroxide, potassium hydroxide, calcium hydroxide, aluminium hydroxide, lithium hydroxide, magnesium hydroxide, and zinc hydroxide. Suitable amine base addition salts are prepared from amines which have sufficient basicity to form a stable salt, and preferably include those amines which are frequently used in medicinal chemistry because of their low toxicity and acceptability for medical use, such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: *Design of Prodrugs,* H. Bundgaard, ed., Elsevier (1985); *Methods in Enzymology,* K. Widder et al, Ed., Academic Press, 42, p. 309-396 (1985); *A Textbook of Drug Design and Development,* Krogsgaard-Larsen and H. Bundgaard, ed., Chapter 5; "Design and Applications of Prodrugs" p. 113-191 (1991); *Advanced Drug Delivery Reviews,* H. Bundgard, 8, p. 1-38 (1992); *J. Pharm. Sci.,* 77:285 (1988); Nakeya et al, *Chem. Pharm. Bull.,* 32:692 (1984); Higuchi et al., "Pro-drugs as Novel Delivery Systems," Vol. 14 of the *A.C.S. Symposium Series, and Bioreversible Carriers in Drug Design,* Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The term "solvate" refers to a compound of Formula (I), Formula (Ia), Formula (Ib), and Formula (Ic) in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amounts" is meant to describe an amount of compound of the present invention effective to produce the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history; the particular compound used, as well as the carrier in which it is formulated and the route of administration selected for it; and, the nature and severity of the condition being treated.

The term "pharmaceutical composition" means a composition comprising a compound of Formula (I) Formula (Ia), Formula (Ib), and Formula (Ic) and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgement, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This technology also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

Compounds of the present invention can be produced according to known methods. For example, compounds of the present invention wherein s is 0 can be prepared according to Scheme 1 and Scheme 2 outlined below.

Scheme 1

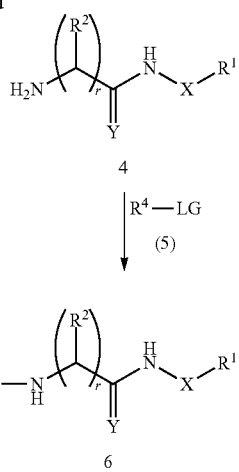

R = OH, Bt, or OSu
LG is a leaving group
PG is a protecting group

Reaction of the carboxylic acid derivative (1) with amine R¹X—NH₂ (2) leads to formation of the compound (3). The reaction can be carried out in a variety of solvents, for example in methylene chloride (CH₂Cl₂), tetrahydrofuran (THF), dimethylformamide (DMF), or other such solvents or in the mixture of such solvents. During the reaction process, the non-participating carboxylic acids or amines on the reacting set of amino acids or peptide fragments can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Following the deprotection, amine (4) is reacted with R⁴-LG (5) (wherein LG is a suitable leaving group) to form final product (6).

Scheme 2

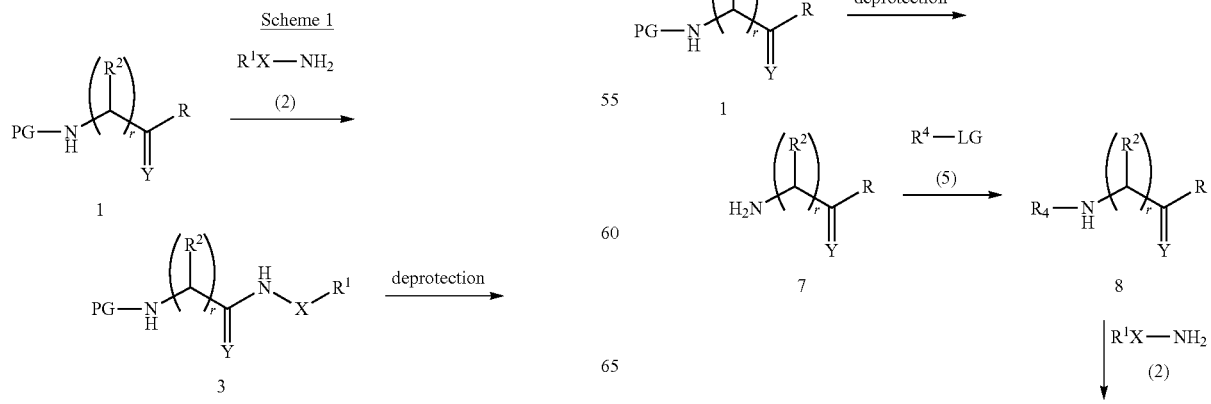

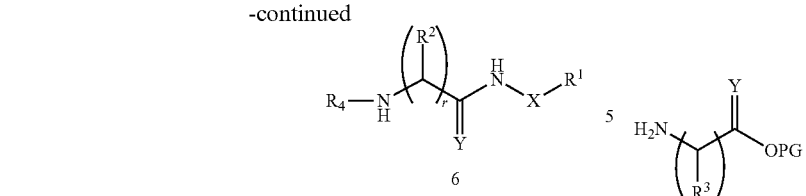

R = OH, Bt, or OSu
LG is a leaving group
PG is a protecting group

Alternatively, carboxylic acid derivative bearing protecting group (PG) (1) can be first deprotected and then reacted with the R⁴-LG (5) (wherein LG is a suitable leaving group) to form compound (8). Compound (8) can be then reacted with amine (2), R¹X—NH₂, to form final product (6).

Compounds of the present invention wherein s is 1 can be prepared according to the general schemes outlined below (Schemes 3-7).

Scheme 4

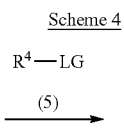

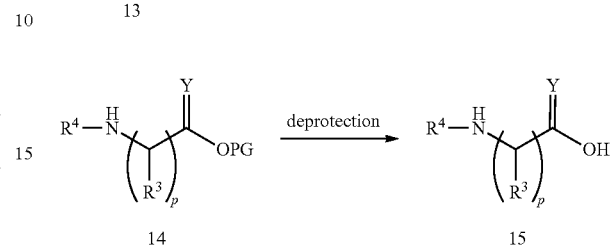

Scheme 3

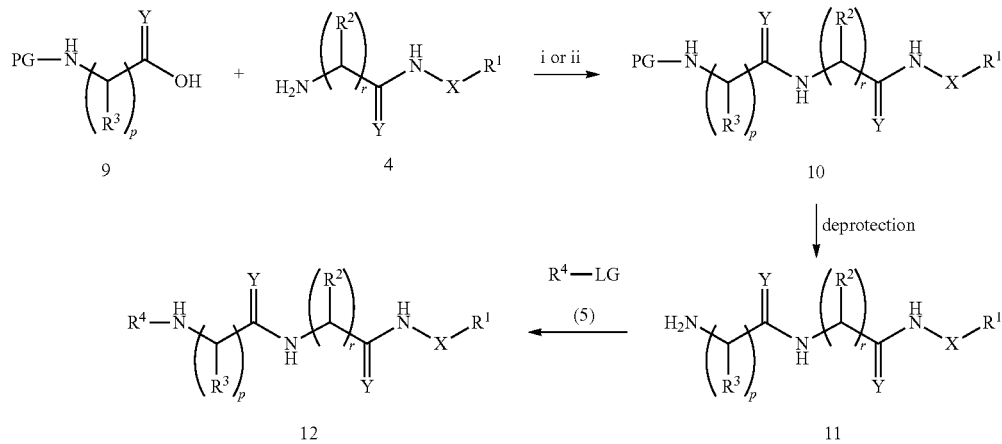

i) HATU, HOAt, DMF
ii) EDC, HOBt, DMF
LG is a leaving group
PG is a protecting group The compounds of the present invention may be prepared by stepwise coupling of the amino acids. The coupling reactions are conducted in solvents such as methylene chloride (CH₂Cl₂), tetrahydrofuran (THF), dimethylformamide (DMF), or other such solvents. During the coupling process, the non-participating carboxylic acids or amines on the reacting set of amino acids or peptide fragments can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Carboxylic acid bearing protecting group (PG) (9) is coupled with the amine (4) to form compound (10). Following the deprotection reaction, compound (11) is reacted with R⁴-LG (5) to form final product (12).

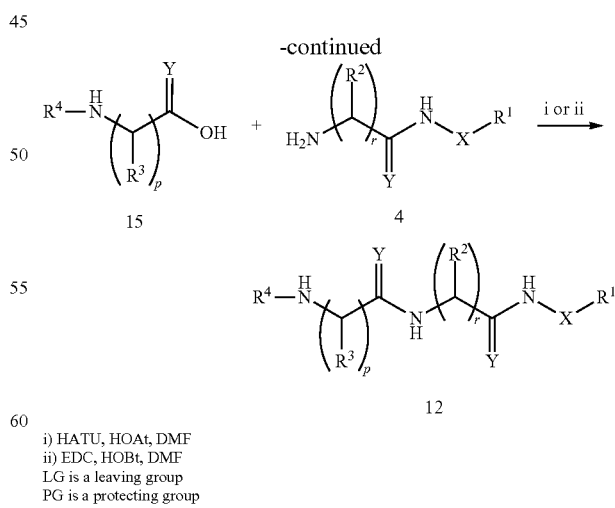

i) HATU, HOAt, DMF
ii) EDC, HOBt, DMF
LG is a leaving group
PG is a protecting group Alternatively, carboxylic acid bearing protecting group (PG) (13) can be first reacted with R⁴-LG (wherein LG is a suitable leaving group) (5) to form compound (14). Then, following the deprotection reaction, acid (15) can be coupled with amine (4) to form final product (12).

Scheme 5

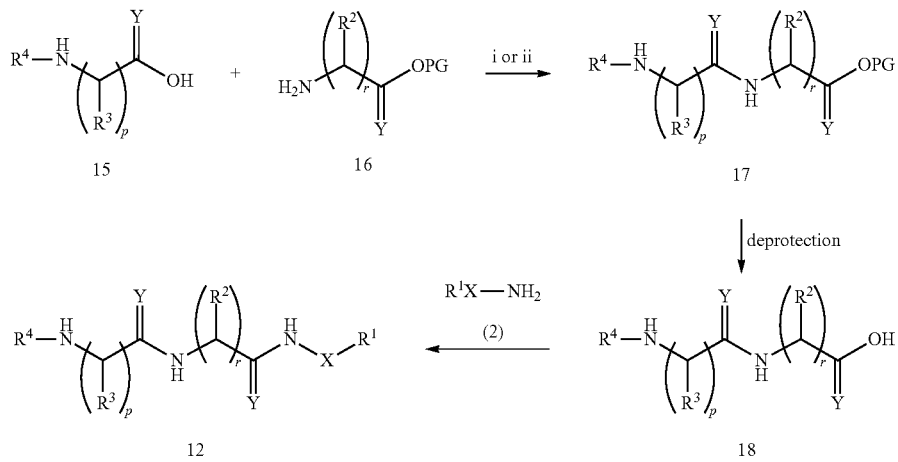

i) HATU, HOAt, DMF
ii) EDC, HOBt, DMF
LG is a leaving group
PG is a protecting group Alternatively, acid (15) can be first coupled with amino acid (16) to form compound (17). Following the deprotection reaction, acid (18) can be reacted with amine (2), $R^1X$—$NH_2$, to form final product (12).

Scheme 6

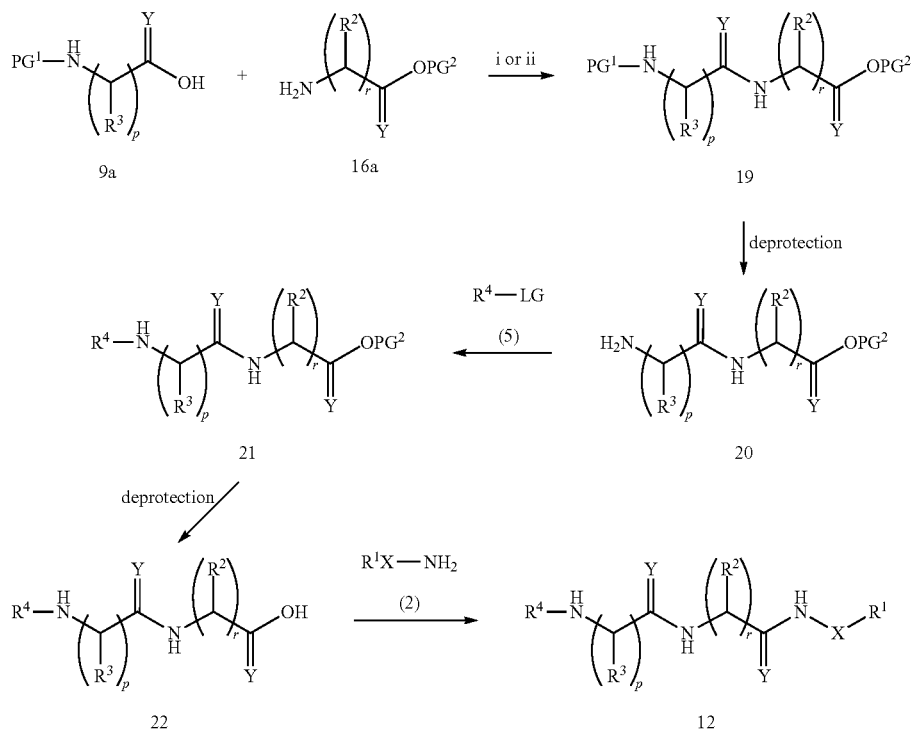

i) HATU, HOAt, DMF
ii) EDC, HOBt, DMF
LG is a leaving group
$PG^1$ and $PG^2$ are protecting groups Alternatively, amino acid (9a) can be coupled with amino acid (16a) to form compound (19). Following the deprotection reaction, acid (20) can be reacted with R⁴-LG (wherein LG is a suitable leaving group) (5) to form compound (21). Following the deprotection reaction, acid (22) can be coupled with amine (2), R¹X—NH₂, to form final product (12).

Scheme 7

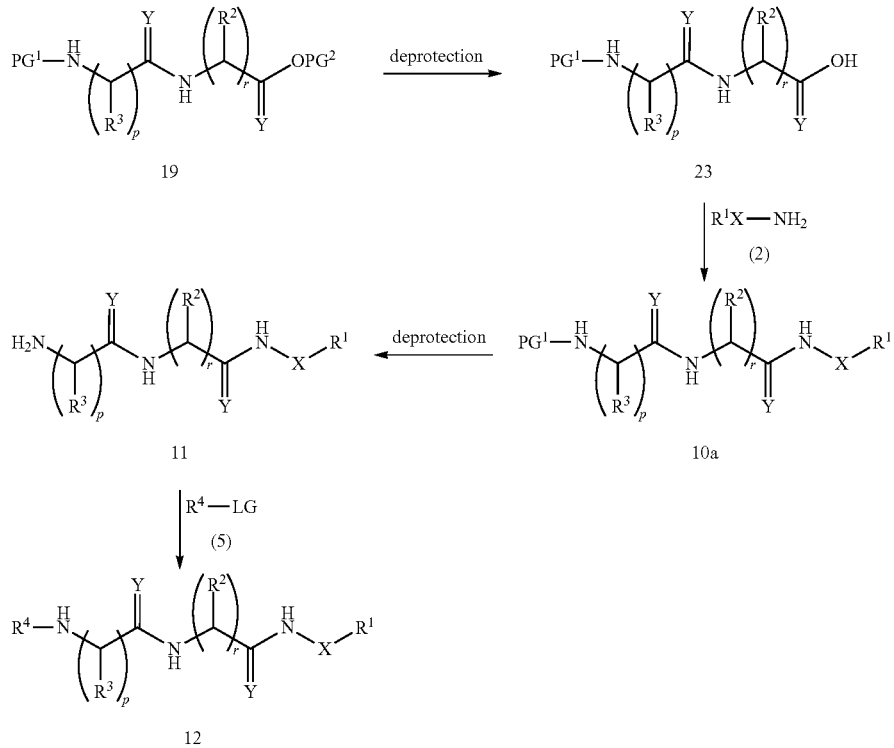

i) HATU, HOAt, DMF
ii) EDC, HOBt, DMF
LG is a leaving group
PG¹ and PG² are protecting groups Alternatively, following the deprotection reaction, acid (23) can be coupled with amine (2), R¹X—NH₂, to form compound (10a). Following the deprotection reaction, amine (11) can then be reacted with R⁴-LG (wherein LG is a suitable leaving group) (5) to form final product (12).

Compounds of the present invention wherein Y is O can be easily converted to their analogs wherein Y is S, according to known methods. For example by using Lawesson's reagent.

Another aspect of the present invention relates to a compound of Formula (Ia), Formula (Ib), or Formula (Ic):

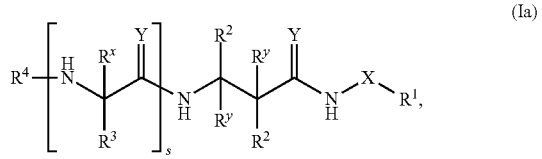

wherein
R¹ is selected from the group consisting of monocyclic and bicyclic aryl, biphenyl, monocyclic and bicyclic heteroaryl, monocyclic and bicyclic heterocyclyl, and monocyclic and bicyclic non-aromatic heterocycle, wherein monocyclic and bicyclic aryl, biphenyl, monocyclic and bicyclic heteroaryl, monocyclic and bicyclic heterocyclyl, and monocyclic and bicyclic non-aromatic heterocycle can be optionally substituted from 1 to 3 times with a substituent selected independently at each occurrence thereof from the group consisting of halogen, cyano, —CF$_3$, C$_{1-6}$ alkyl, and C$_{1-6}$ alkoxy;

R$^2$ is independently selected at each occurrence thereof from the group consisting of H, D, C$_{1-6}$ alkyl, —CH$_2$OC$_{1-6}$ alkyl, —CH$_2$Ar, and —CH$_2$heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;

R$^3$ is independently selected at each occurrence thereof from the group consisting of H, D, —CH$_2$OC$_{1-6}$ alkyl, —(CH$_2$)$_m$C(O)NHR$^5$, and —(CH$_2$)$_m$C(O)NR$^6$R$^7$;

R$^4$ is selected from the group consisting of —C(O)(CH$_2$)$_n$Ph, —C(O)CH$_2$NR$^6$R$^7$, —SO$_2$Ar, —SO$_2$C$_{1-6}$ alkyl, —SO$_2$C$_{3-6}$ cycloalkyl, —C(O)(CH$_2$)$_n$Het, —C(O)C(O)Het, —C(O)C$_{1-6}$ alkyl, —C(O)OC$_{1-6}$ alkyl, —C(O)CF$_3$, heteroaryl, and —(CH$_2$)$_n$NR$^6$R$^7$, wherein aryl (Ar) and heteroaryl (Het) can be optionally substituted from 1 to 3 times with a substituent selected independently at each occurrence thereof from the group consisting of halogen, cyano, C$_{1-6}$ alkyl, and C$_{1-6}$ alkoxy;

R$^5$ is selected from the group consisting of C$_{1-6}$ alkyl, C$_{1-6}$ alkoxy, non-aromatic heterocycle, —NR$^6$R$^7$, and —CR$^8$R$^9$;

R$^6$, R$^7$, R$^8$, and R$^9$ are each independently selected from the group consisting of H, D, C$_{1-6}$ alkyl, and —(CH$_2$)$_k$OH;

or R$^6$ and R$^7$ are taken together with the nitrogen to which they are attached to form a morpholine ring;

or R$^8$ and R$^9$ are taken together with the carbon to which they are attached to form an oxetane ring;

R$^x$ is independently selected at each occurrence thereof from the group consisting of H, D, —CH$_2$OC$_{1-6}$ alkyl, —(CH$_2$)$_m$C(O)NHR$^5$, —(CH$_2$)$_m$C(O)NR$^6$R$^7$, and —CH$_2$C(O)R$^5$;

R$^y$ is independently selected at each occurrence thereof from the group consisting of H, D, C$_{1-6}$ alkyl, —CH$_2$OC$_{1-6}$ alkyl, —CH$_2$Ar, and —CH$_2$heteroaryl, wherein aryl (Ar) can be optionally substituted from 1 to 3 times with a substituent selected independently at each occurrence thereof from the group consisting of halogen, cyano, C$_{1-6}$ alkyl, and C$_{1-6}$ alkoxy;

X is —(CH$_2$)$_q$—, —O—, or —(CD$_2$)$_q$-;
Y is O or S;
k is 1, 2, or 3;
m is 0, 1, 2, 3, 4, or 5;
n is 0, 1, 2, or 3;
q is 0, 1, or 2; and
s is 0 or 1;

or an oxide thereof, a pharmaceutically acceptable salt thereof, a solvate thereof, or a prodrug thereof.

Compounds according to the present invention include compounds of Formula (I), Formula (Ia), Formula (Ib), and Formula (Ic). In one embodiment compound according to the present invention is a compound of Formula (I). In another embodiment the compound according to the present invention is a compound of Formula (Ia), Formula (Ib), or Formula (Ic).

In one embodiment, compound has the formula:

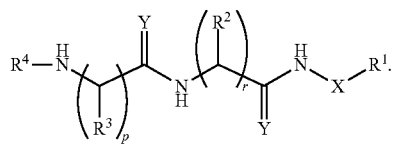

In another embodiment, compound has the formula

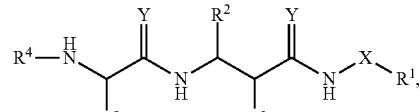

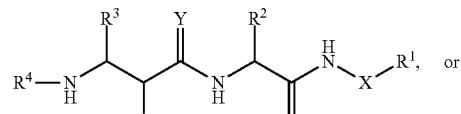

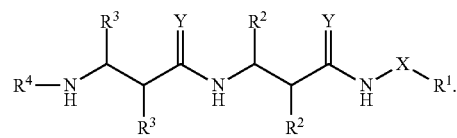

One embodiment relates to the compounds of the present invention where R$^1$ is selected from the group consisting of

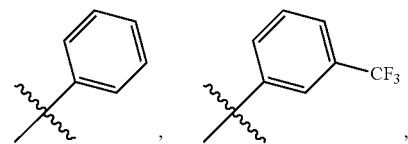

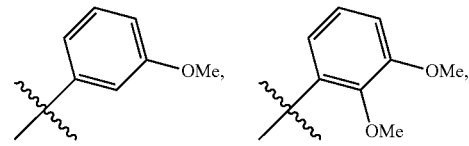

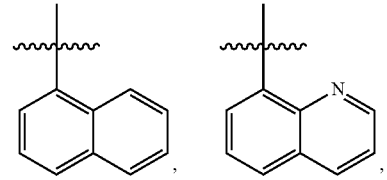

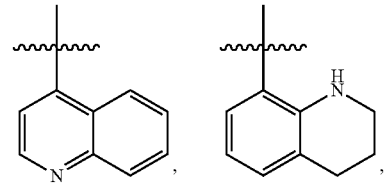

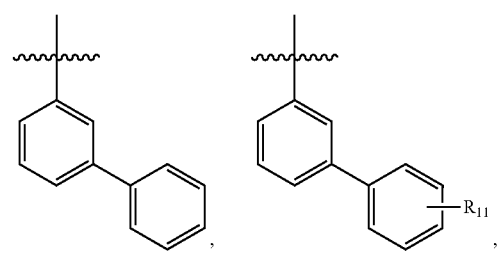

-continued

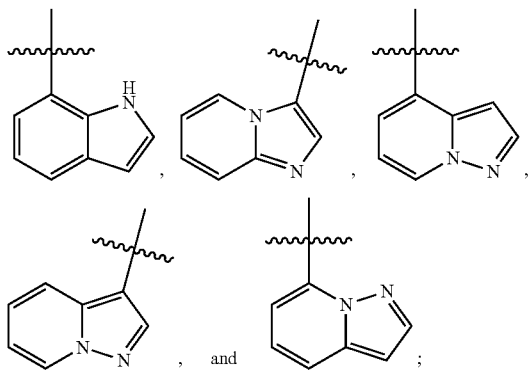

and $R^{11}$ is selected from the group consisting of halogen, cyano, —CF$_3$, C$_{1-6}$ alkyl, and C$_{1-6}$ alkoxy.

Another embodiment relates to the compounds of the present invention where $R^2$ is selected from the group consisting of H, Me, —CH$_2$(Me)$_2$, —CH$_2$OMe,

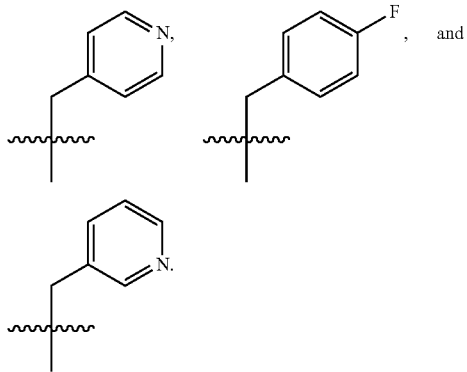

Another embodiment relates to the compounds of the present invention where $R^2$ is selected from the group consisting of Me, —CH$_2$(Me)$_2$, —CH$_2$OMe,

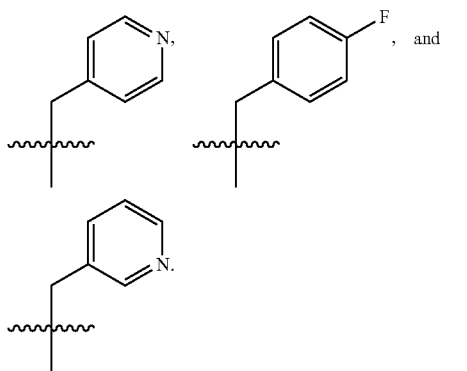

One embodiment relates to the compounds of the present invention where $R^3$ is selected from the group consisting of —CH$_2$OMe, —CH$_2$C(O)OH, —CH$_2$C(O)OBn, —(CH$_2$)$_2$C(O)OBn, —(CH$_2$)$_2$C(O)OH,

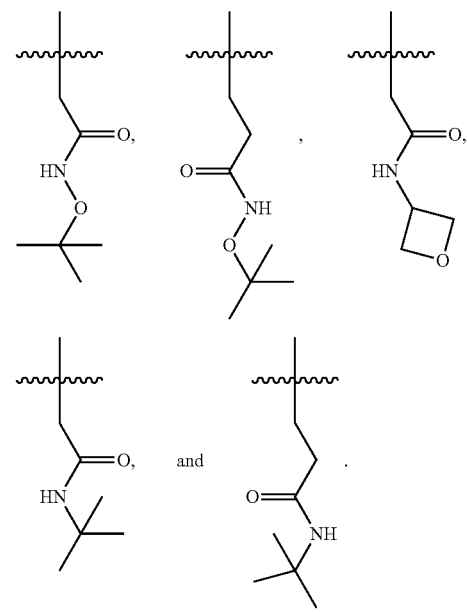

Another embodiments relates to the compounds of the present invention where $R^3$ is selected from the group consisting of —CH$_2$OMe,

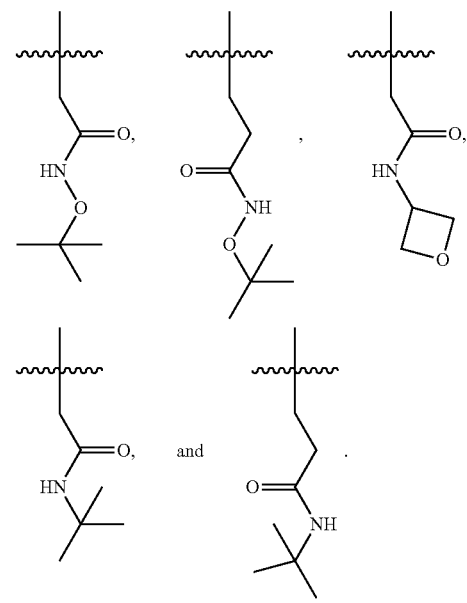

Another embodiment relates to the compounds of the present invention where $R^4$ is selected from the group consisting of H, trifluoroacetyl,

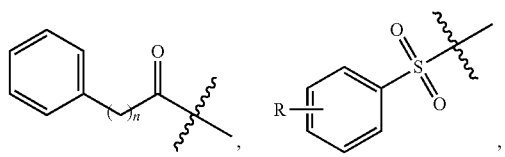

-continued

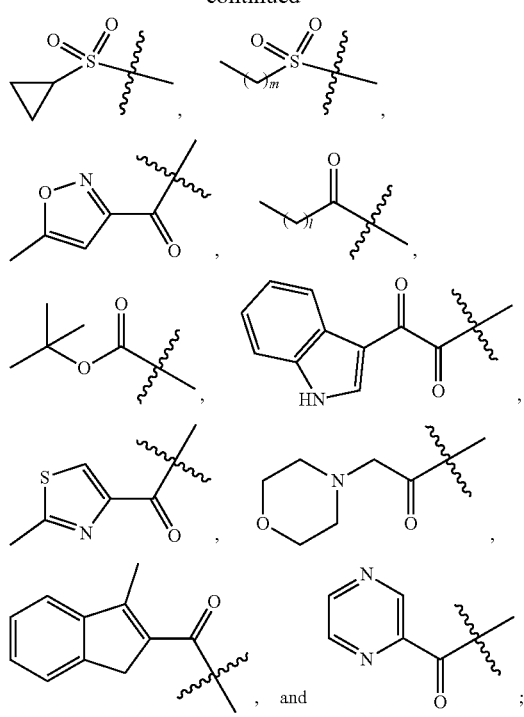

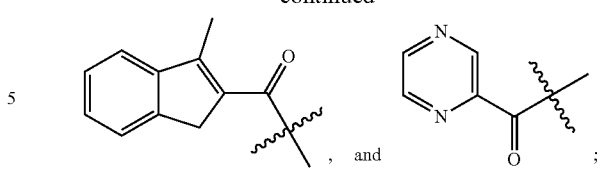
, and l is 0, 1, 2, 3, or 4;

m is 0, 1, 2, 3, 4, or 5;

n is 0, 1, 2, or 3; and

R is selected from the group consisting of H, halogen, cyano, $C_{1-6}$ alkyl, and $C_{1-6}$ alkoxy.

One embodiment relates to the compounds of the present invention where the compound has a structure selected from the group consisting of:

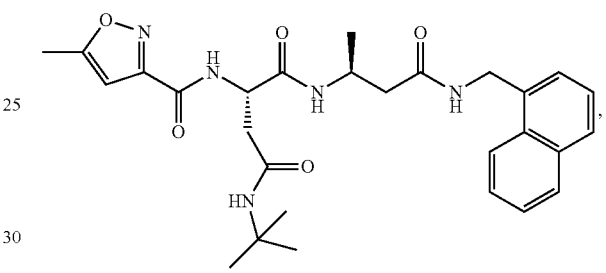

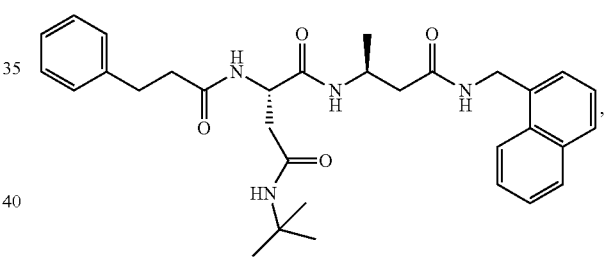

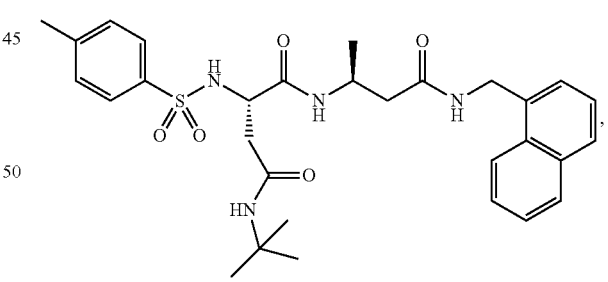

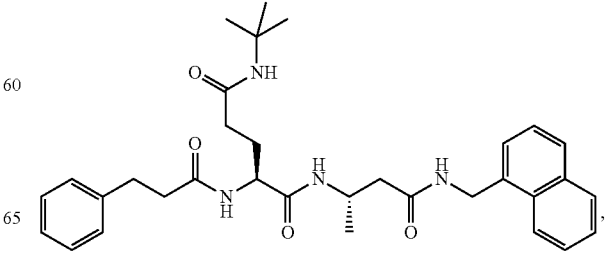

l is 0, 1, 2, 3, or 4;

m is 0, 1, 2, 3, 4, or 5;

n is 0, 1, 2, or 3; and

R is selected from the group consisting of H, halogen, cyano, $C_{1-6}$ alkyl, and $C_{1-6}$ alkoxy.

Yet another embodiment relates to the compounds of the present invention where $R^4$ is selected from the group consisting of trifluoroacetyl,

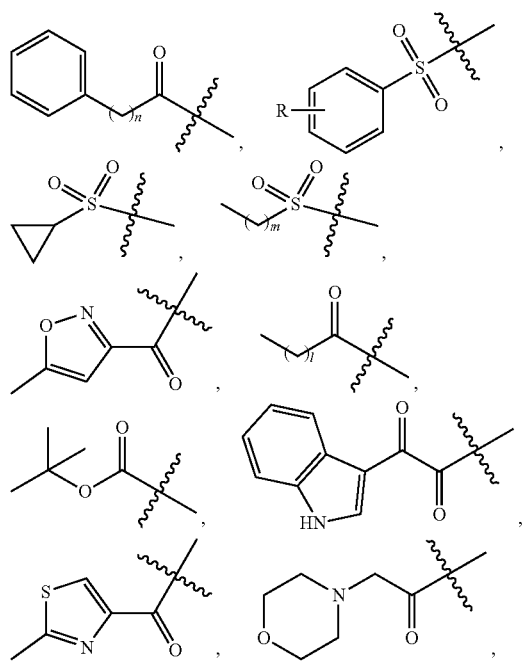

-continued
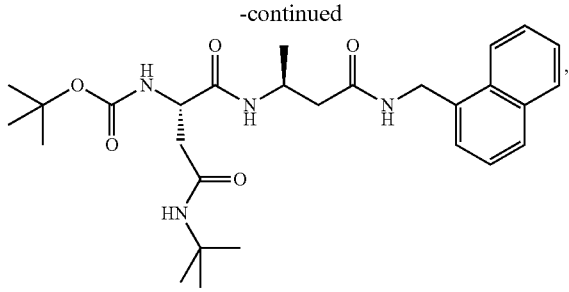
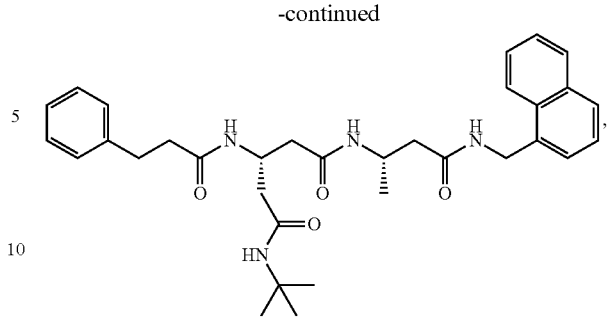
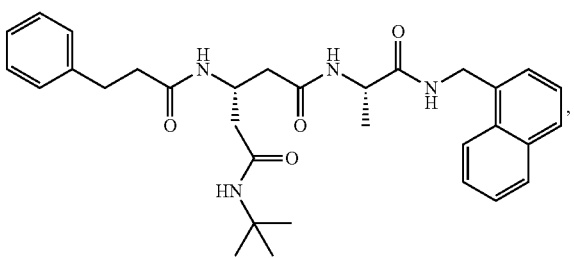
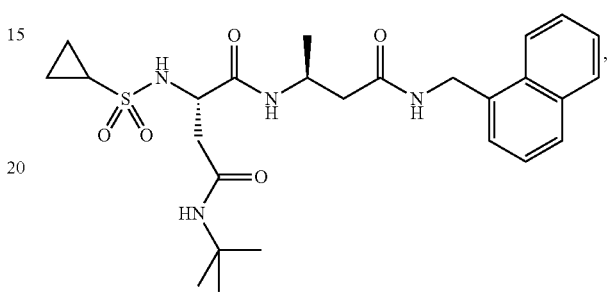
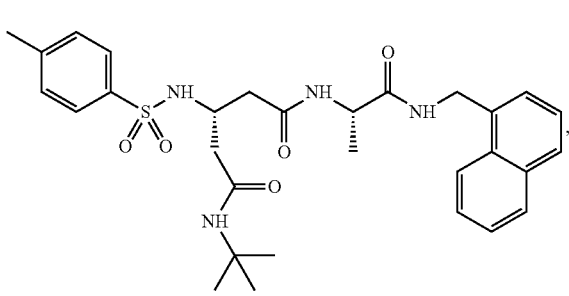
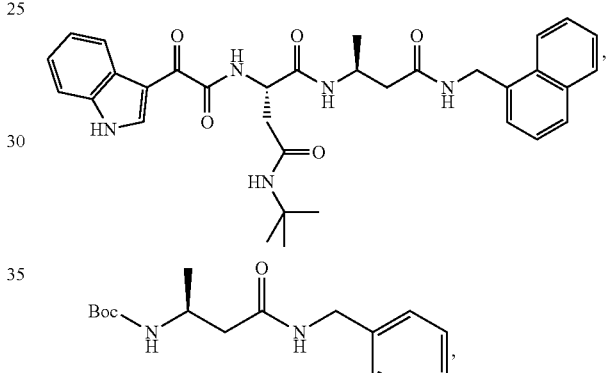
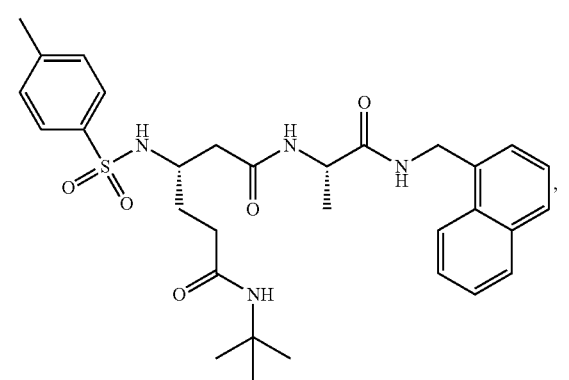
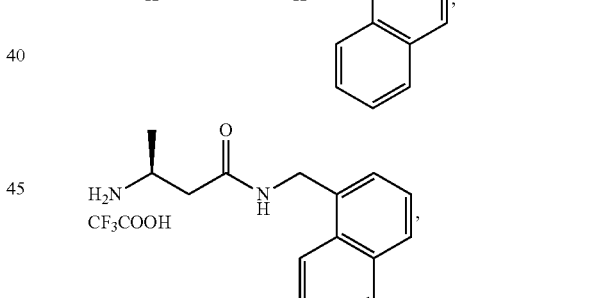
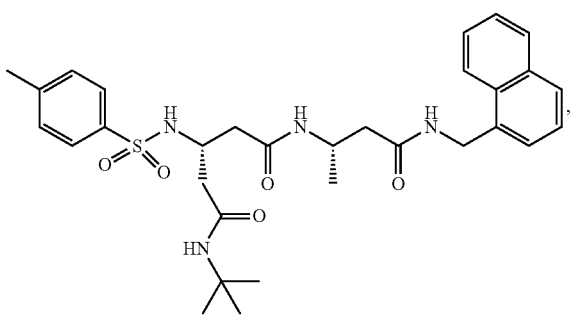
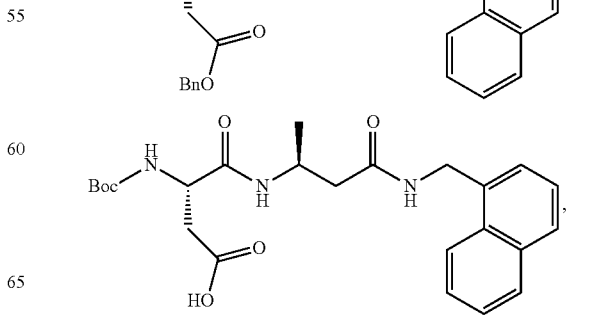

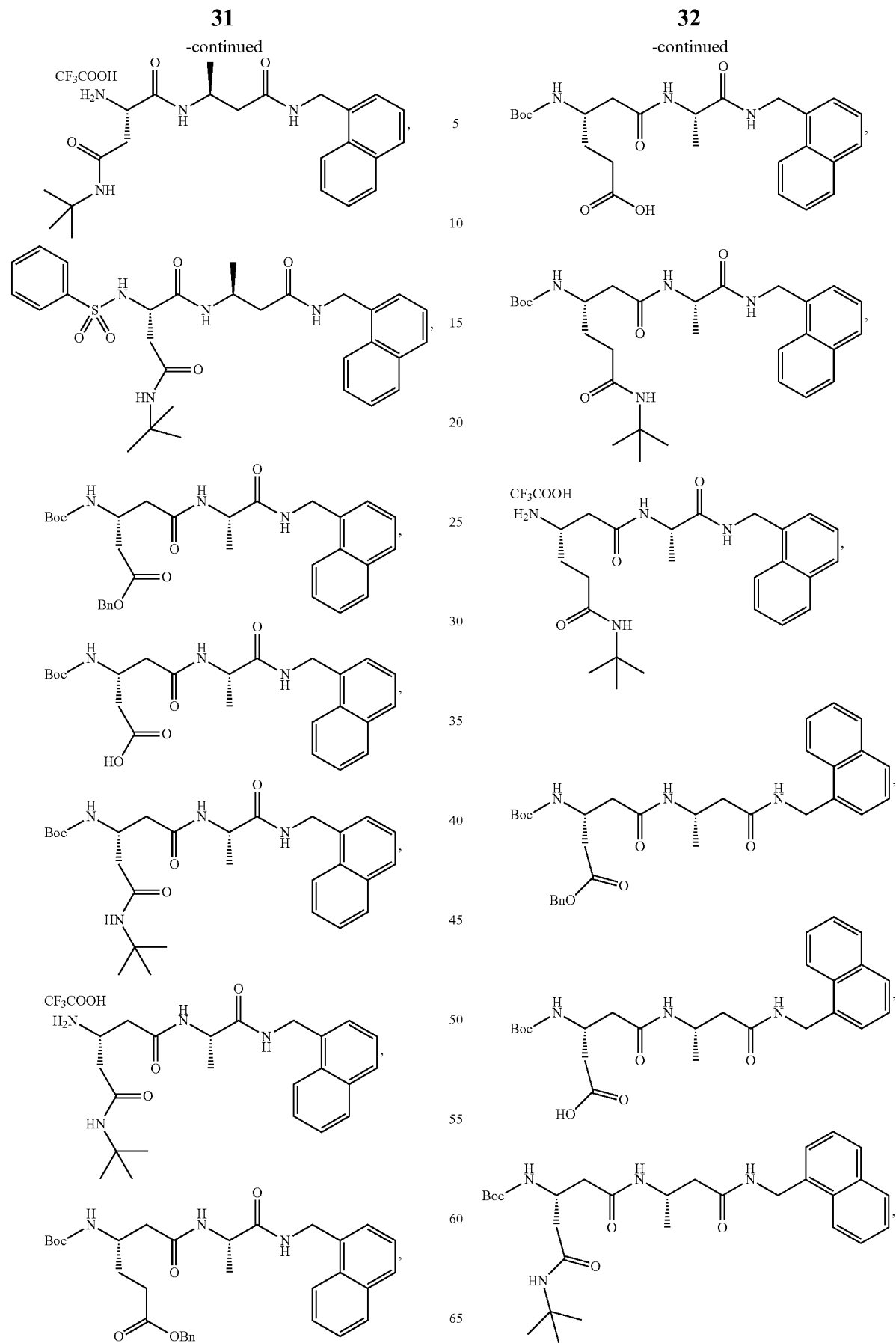

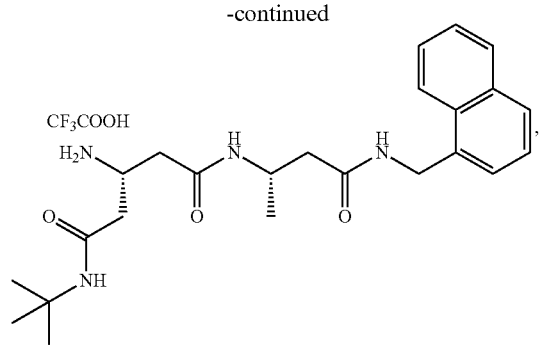
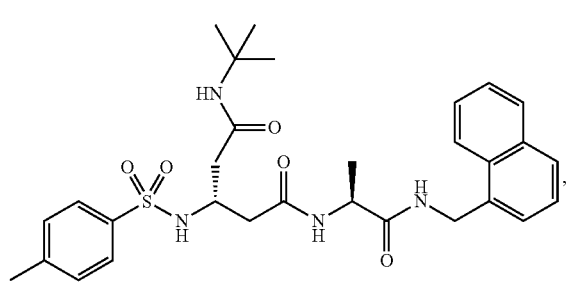
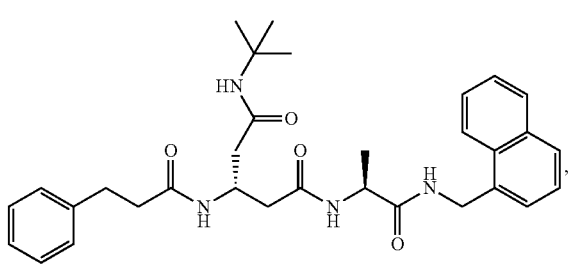
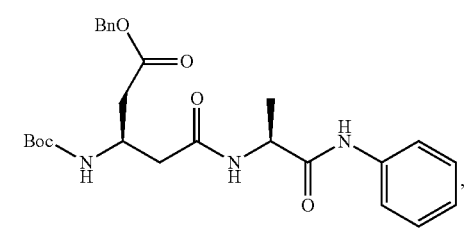
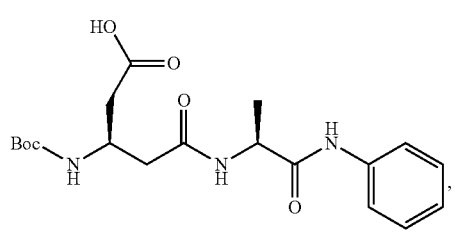
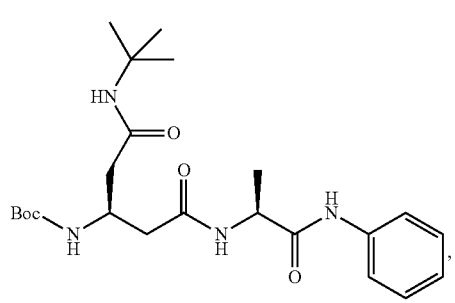
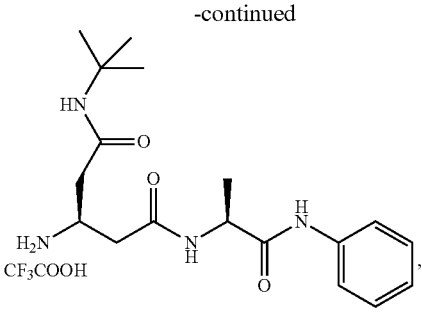
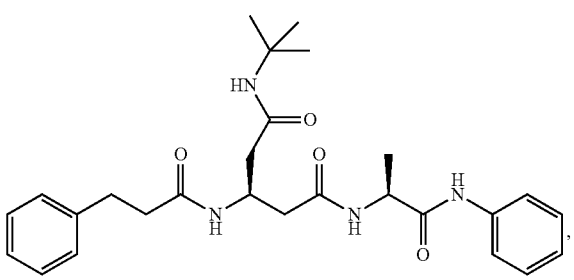
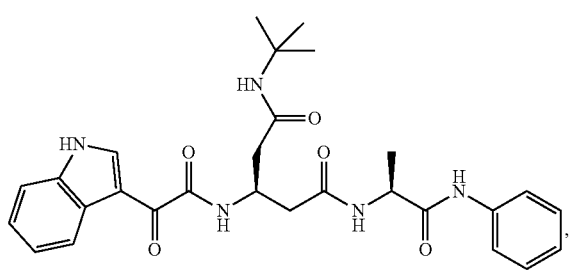
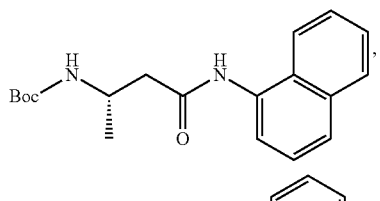
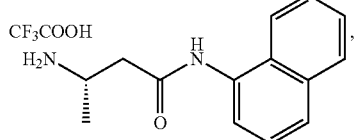
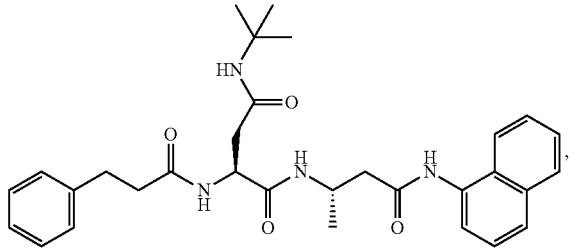
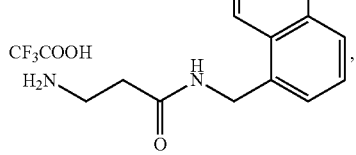

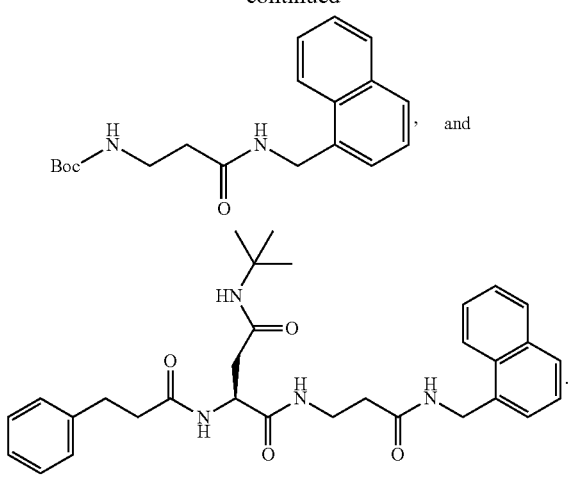
Another embodiments relates to the compound of the present invention where the compound has a structure selected from the group consisting of:
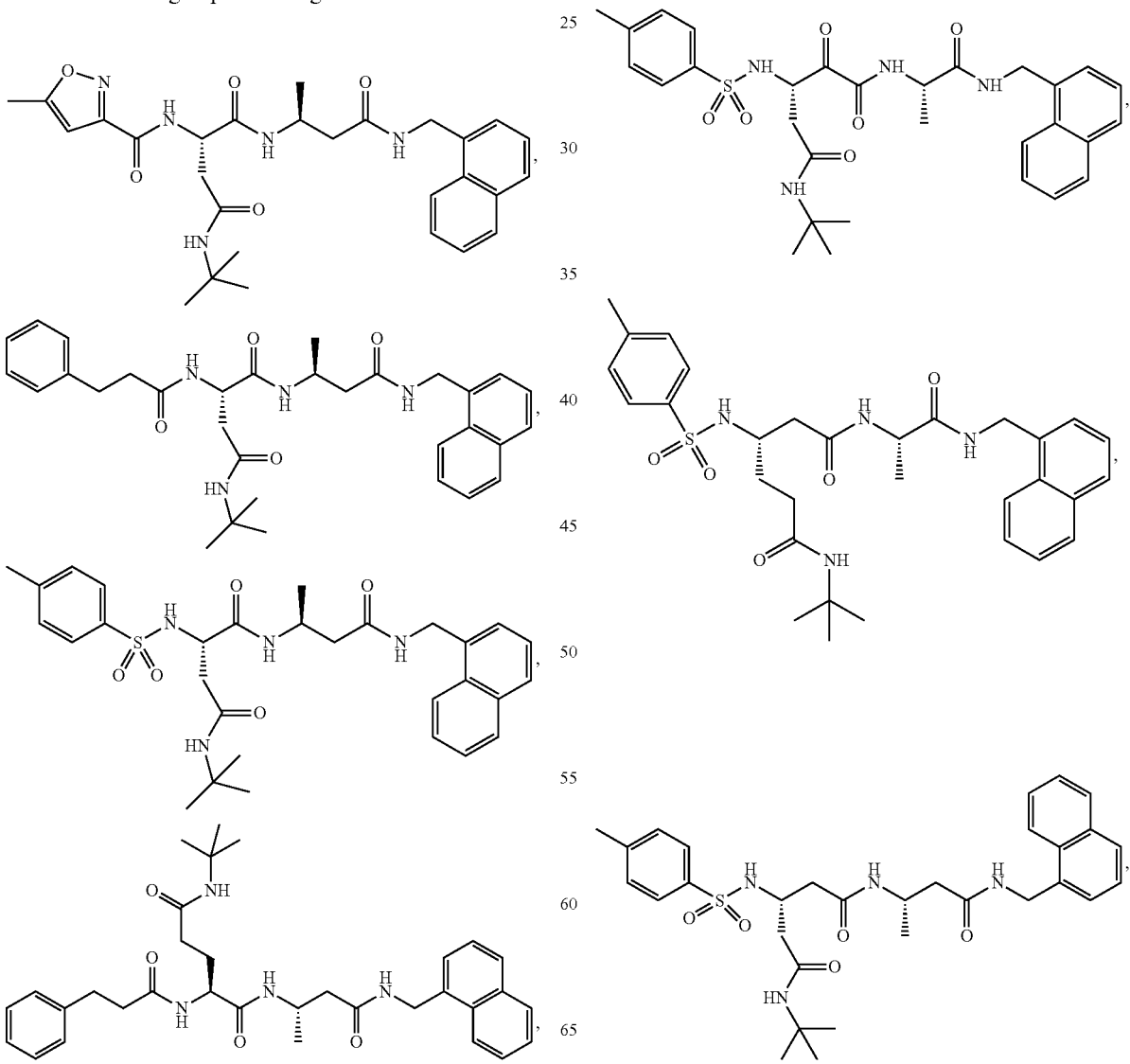
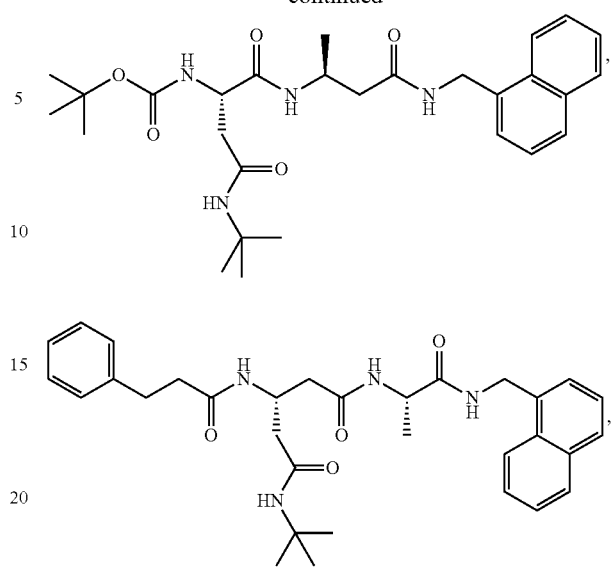

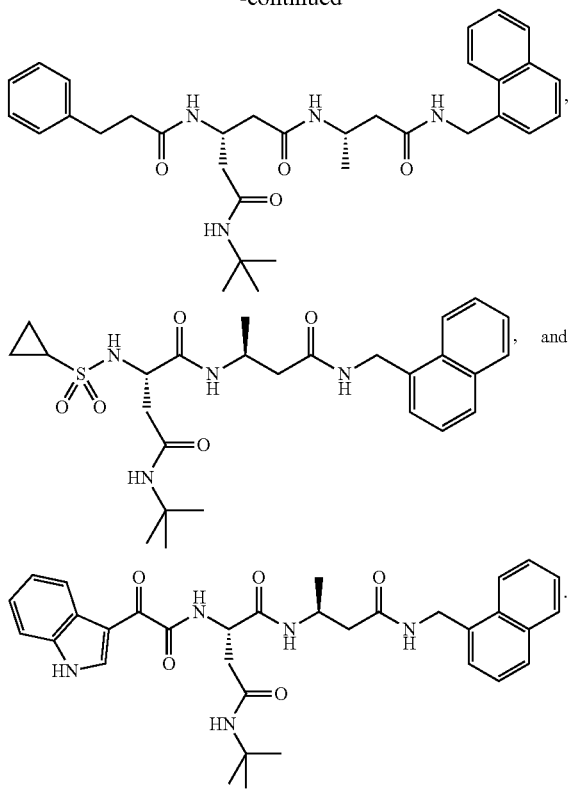

While it may be possible for compounds of the present invention to be administered as raw chemicals, it will often be preferable to present them as a part of a pharmaceutical composition. Accordingly, another aspect of the present invention is a pharmaceutical composition containing a therapeutically effective amount of the compound of the present invention, or a pharmaceutically acceptable salt or solvate thereof, and a pharmaceutically acceptable carrier. The carrier must be "acceptable" in the sense of being compatible with the other ingredients of the formulation and not deleterious to the recipient thereof.

Compounds according to the present invention include compounds of Formula (I), Formula (Ia), Formula (Ib), and Formula (Ic). In one embodiment compound according to the present invention is a compound of Formula (I). In another embodiment the compound according to the present invention is a compound of Formula (Ia), Formula (Ib), or Formula (Ic).

In practicing the method of the present invention, agents suitable for treating a subject can be administered using any method standard in the art. The agents, in their appropriate delivery form, can be administered orally, intradermally, intramuscularly, intraperitoneally, intravenously, subcutaneously, or intranasally. The compositions of the present invention may be administered alone or with suitable pharmaceutical carriers, and can be in solid or liquid form, such as tablets, capsules, powders, solutions, suspensions, or emulsions.

The agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the agents of the present invention. The agents may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. (Abuchowski and Davis, "Soluble Polymer-Enzyme Adducts," In: Enzymes as Drugs, Hocenberg and Roberts, eds., Wiley-Interscience, New York, N.Y., pp. 367-383 (1981), which are hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, sucrulose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The agents of the present invention may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The agents of the present invention may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. The agent of the present invention also may be administered in a non-pressurized form such as in a nebulizer or atomizer.

Effective doses of the compositions of the present invention, for the treatment of cancer or pathogen infection vary depending upon many different factors, including type and stage of cancer or the type of pathogen infection, means of administration, target site, physiological state of the patient, other medications or therapies administered, and physical state of the patient relative to other medical complications. Treatment dosages need to be titrated to optimize safety and efficacy.

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.1 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

Another aspect of the present invention relates to a method of treating cancer, immunologic disorders, autoimmune disorders, neurodegenerative disorders, or inflammatory disorders in a subject or for providing immunosuppression for transplanted organs or tissues in a subject. This method includes administering to the subject in need thereof a compound of the Formula (I):

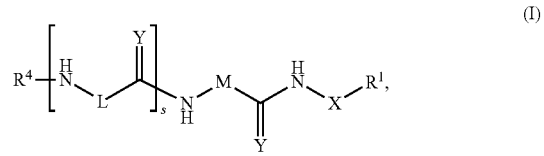

wherein
L is —$(CR^3R^x)_p$—;
M is —$(CR^2R^y)_r$—;
$R^1$ is selected from the group consisting of monocyclic and bicyclic aryl, biphenyl, monocyclic and bicyclic heteroaryl, monocyclic and bicyclic heterocyclyl, and monocyclic and bicyclic non-aromatic heterocycle, wherein monocyclic and bicyclic aryl, biphenyl, monocyclic and bicyclic heteroaryl, monocyclic and bicyclic heterocyclyl, and monocyclic and bicyclic non-aromatic heterocycle can be optionally substituted from 1 to 3 times with a substituent selected independently at each occurrence thereof from the group consisting of halogen, cyano, —$CF_3$, $C_{1-6}$ alkyl, and $C_{1-6}$ alkoxy;
$R^2$ is independently selected at each occurrence thereof from the group consisting of H, D, $C_{1-6}$ alkyl, —$CH_2OC_{1-6}$ alkyl, —$CH_2Ar$, and —$CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;
$R^3$ is independently selected at each occurrence thereof from the group consisting of H, D, —$CH_2OC_{1-6}$ alkyl, —$(CH_2)_mC(O)NHR^5$, —$(CH_2)_mC(O)NR^6R^7$, —$(CH_2)_mC(O)OH$, and —$(CH_2)_mC(O)OBn$;
$R^4$ is selected from the group consisting of H, —$C(O)(CH_2)_nPh$, —$C(O)CH_2NR^6R^7$, —$SO_2Ar$, —$SO_2C_{1-6}$ alkyl, —$SO_2C_{3-6}$ cycloalkyl, —$C(O)(CH_2)_n$Het, —$C(O)C(O)$Het, —$C(O)C_{1-6}$ alkyl, —$C(O)OC_{1-6}$ alkyl, —$C(O)CF_3$, heteroaryl, and —$(CH_2)_nNR^6R^7$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ alkoxy;
$R^5$ is selected from the group consisting of $C_{1-6}$ alkyl, $C_{1-6}$ alkoxy, non-aromatic heterocycle, —$NR^6R^7$, and —$CR^8R^9$;

$R^6$, $R^7$, $R^8$, and $R^9$ are each independently selected from the group consisting of H, D, $C_{1-6}$ alkyl, and —$(CH_2)_k$OH;

or $R^6$ and $R^7$ are taken together with the nitrogen to which they are attached to form a morpholine ring;

or $R^8$ and $R^9$ are taken together with the carbon to which they are attached to form an oxetane ring;

$R^x$ is independently selected at each occurrence thereof from the group consisting of H, D, —$CH_2OC_{1-6}$ alkyl, —$(CH_2)_mC(O)NHR^5$, —$(CH_2)_mC(O)NR^6R^7$, and —$CH_2C(O)R^5$;

$R^y$ is independently selected at each occurrence thereof from the group consisting of H, D, $C_{1-6}$ alkyl, —$CH_2OC_{1-6}$ alkyl, —$CH_2Ar$, and —$CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

X is —$(CH_2)_q$—, —O—, or —$(CD_2)_q$-;
Y is O or S;
k is 1, 2, or 3;
m is 0, 1, 2, 3, 4, or 5;
n is 0, 1, 2, or 3;
p is 1 or 2;
q is 0, 1, or 2;
r is 1 or 2; and
s is 0 or 1;

with a proviso that when s is 0, then r is 2; and when s is 1, then r+p≥3.

Yet another aspect of the present invention relates to a method of treating cancer, immunologic disorders, autoimmune disorders, neurodegenerative disorders, or inflammatory disorders in a subject or for providing immunosuppression for transplanted organs or tissues in a subject. This method includes administering to the subject in need thereof a compound of the Formula (Ia), Formula (Ib), or Formula (Ic):

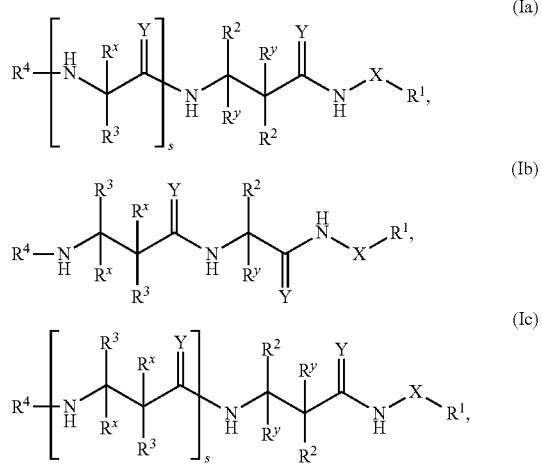

wherein
$R^1$ is selected from the group consisting of monocyclic and bicyclic aryl, biphenyl, monocyclic and bicyclic heteroaryl, monocyclic and bicyclic heterocyclyl, and monocyclic and bicyclic non-aromatic heterocycle, wherein monocyclic and bicyclic aryl, biphenyl, monocyclic and bicyclic heteroaryl, monocyclic and bicyclic heterocyclyl, and monocyclic and bicyclic non-aromatic heterocycle can be optionally substituted from 1 to 3 times with a substituent selected independently at each occurrence thereof from the group consisting of halogen, cyano, —$CF_3$, $C_{1-6}$ alkyl, and $C_{1-6}$ alkoxy;

$R^2$ is independently selected at each occurrence thereof from the group consisting of H, D, $C_{1-6}$ alkyl, —$CH_2OC_{1-6}$ alkyl, —$CH_2Ar$, and —$CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

$R^3$ is independently selected at each occurrence thereof from the group consisting of H, D, —$CH_2OC_{1-6}$ alkyl, —$(CH_2)_mC(O)NHR^5$, and —$(CH_2)_mC(O)NR^6R^7$;

$R^4$ is selected from the group consisting of —$C(O)(CH_2)_n$Ph, —$C(O)CH_2NR^6R^7$, —$SO_2Ar$, —$SO_2C_{1-6}$ alkyl, —$SO_2C_{3-6}$ cycloalkyl, —$C(O)(CH_2)_n$Het, —$C(O)C(O)$Het, —$C(O)C_{1-6}$ alkyl, —$C(O)OC_{1-6}$ alkyl, —$C(O)CF_3$, heteroaryl, and —$(CH_2)_nNR^6R^7$, wherein aryl (Ar) and heteroaryl (Het) can be optionally substituted from 1 to 3 times with a substituent selected independently at each occurrence thereof from the group consisting of halogen, cyano, $C_{1-6}$ alkyl, and $C_{1-6}$ alkoxy;

$R^5$ is selected from the group consisting of $C_{1-6}$ alkyl, $C_{1-6}$ alkoxy, non-aromatic heterocycle, —$NR^6R^7$, and —$CR^8R^9$;

$R^6$, $R^7$, $R^8$, and $R^9$ are each independently selected from the group consisting of H, D, $C_{1-6}$ alkyl, and —$(CH_2)_k$OH;

or $R^6$ and $R^7$ are taken together with the nitrogen to which they are attached to form a morpholine ring;

or $R^8$ and $R^9$ are taken together with the carbon to which they are attached to form an oxetane ring;

$R^x$ is independently selected at each occurrence thereof from the group consisting of H, D, —$CH_2OC_{1-6}$ alkyl, —$(CH_2)_mC(O)NHR^5$, —$(CH_2)_mC(O)NR^6R^7$, and —$CH_2C(O)R^5$;

$R^y$ is independently selected at each occurrence thereof from the group consisting of H, D, $C_{1-6}$ alkyl, —$CH_2OC_{1-6}$ alkyl, —$CH_2Ar$, and —$CH_2$heteroaryl, wherein aryl (Ar) can be optionally substituted from 1 to 3 times with a substituent selected independently at each occurrence thereof from the group consisting of halogen, cyano, $C_{1-6}$ alkyl, and $C_{1-6}$ alkoxy;

X is —$(CH_2)_q$—, —O—, or —$(CD_2)_q$-;
Y is O or S;
k is 1, 2, or 3;
m is 0, 1, 2, 3, 4, or 5;
n is 0, 1, 2, or 3;
q is 0, 1, or 2; and
s is 0 or 1.

In one embodiment, an autoimmune disorder is treated. The autoimmune disorder is selected from the group consisting of arthritis, colitis, multiple sclerosis, lupus, systemic sclerosis, and sjögren syndrome. Alternatively, the autoimmune disorder is selected from the group consisting of arthritis, colitis, multiple sclerosis, and lupus.

In another embodiment, immunosuppression is provided for transplanted organs or tissues. The immunosuppression is used to prevent transplant rejection and graft-verse-host disease.

In another embodiment, an inflammatory disorder is treated. The inflammatory disorder is Crohn's disease, and ulcerative colitis. Alternatively, the inflammatory disorder is Crohn's disease.

In yet another embodiment, cancer is treated. The cancer is selected from the group consisting of neoplastic disorders, hematologic malignances, and lymphocytic malignancies.

EXAMPLES

The following examples are provided to illustrate embodiments of the present invention but are by no means intended to limit its scope.

Example 1—General Procedure for HATU Coupling

Carboxylic acid (1.0 eq.), O-(7-Azabenzotriazol-1-yl)-N,N,N',N'-tetramethyluronium hexafluorophosphate (HATU) (1.2 eq.), and 1-Hydroxy-7-Azabenzotriazole (HOAt) 0.6M in DMF (1.0 eq.) were dissolved in DMF under argon atmosphere. The solution was cooled to 0° C. and amine was added. After stirring for 5 minutes at 0° C., Hünig's base (3-4 eq.) was added. The reaction mixture was stirred at 0° C. for 1 hour. After completion of reaction (1 hour, monitored by LCMS), water (10 mL) was added to reaction mixture and stirred 30 minutes. Product was isolated either by ethyl acetate extraction or filtering the precipitate.

Example 2—General Procedure for EDC Couping

Carboxylic acid (1.0 eq.), N-(3-Dimethylaminopropyl)-N'-ethylcarbodiimide hydrochloride (EDC) (1.2 eq.), and 1-Hydroxybenzotriazole (HOBt) (1.3 eq.) were dissolved in DMF under argon atmosphere. The solution was cooled to 0° C. and tert-butylamine was added. After stirring for 5 minutes at 0° C., Hünig's base (2-3 eq.) was added. The reaction mixture was allowed to warm to room temperature slowly and stirred at room temperature overnight.

Example 3—General Procedure for Boc-Deprotection

The substrate was dissolved in dichloromethane and the solution was cooled to 0° C. Trifluoroacetic acid (20% v/v with respect to dichloromethane) was added to the solution drop wise at 0° C. with constant stirring. The mixture was allowed to warm to room temperature slowly (over a period of 1 hour), and stirred until the completion of reaction (monitored by LCMS). Excess trifluoroacetic acid and dichloromethane were evaporated and crude was dried under vacuum.

Example 4—General Procedure for O-Debenzylation

The substrate was dissolved in methanol. Palladium on carbon (10%) was added carefully. Residual air from the flask was removed and the mixture was stirred at room temperature for 3-4 hours under hydrogen atmosphere using a hydrogen balloon. After completion of reaction, the mixture was filtered through celite. Filtrate was evaporated and dried under vacuum to give product.

Example 5—General Procedure for N-Sulfonamide Preparation of Amines

The primary amine (generally TFA salt) was dissolved in dichloromethane. The solution was cooled to 0° C. and triethylamine (2.0-3.0 eq.) was added. Sulfonyl chloride (1.5 eq.) was added to the solution in one portion and reaction mixture was warmed to room temperature (over 15 minutes). After completion of reaction (2-3 hours), dichloromethane was evaporated and crude was purified by HPLC to give pure product.

Example 6—Preparation of tert-butyl (S)-(4-((naphthalen-1-ylmethyl)amino)-4-oxobutan-2-yl)carbamate (PKS2241, PKS2261)

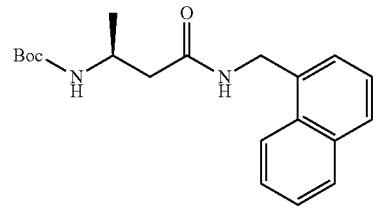 [SMILES: C[C@@H](CC(=O)NCc1cccc2ccccc12)NC(=O)OC(C)(C)C]

The title compound was synthesized by following the general protocol for HATU mediated coupling of Boc-L-β-homoalanine and 1-naphthylmethylamine on a 1.5 mmol scale. After completion of reaction, water was added to reaction mixture to give white precipitate. Precipitate was filtered, washed with water and dried in air to give product (490 mg, 95%) as a white solid. $^1$H NMR (500 MHz, DMSO-$d_6$) δ 8.38 (t, J=5.7 Hz, 1H), 8.06-8.04 (m, 1H), 7.95-7.93 (m, 1H), 7.86-7.84 (m, 1H), 7.56-7.52 (m, 2H), 7.48-7.42 (m, 2H), 6.72 (d, J=8.3 Hz, 1H), 4.76-4.68 (m, 2H), 3.89-3.80 (m, 11H), 2.35 (dd, J=13.9, 5.7 Hz, 1H), 2.18 (dd, J=13.9, 8.2 Hz, 1H), 1.37 (s, 9H), 1.01 (d, J=6.5 Hz, 3H).

Example 7—Preparation of (S)-3-amino-N-(naphthalen-1-ylmethyl)butanamide 2,2,2-trifluoroacetate (PKS2245, PKS2262)

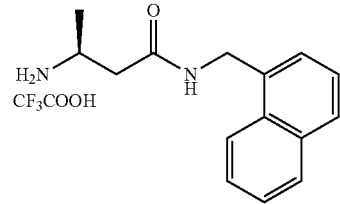 [SMILES: "CF3COOH" ; C[C@H](N)CC(=O)NCc1cccc2ccccc12]

The title compound was prepared by following the general protocol for Boc-deprotection of PKS2261 (480 mg, 1.40 mmol). The crude yellow paste was triturated with diethyl ether and kept standing overnight. The white solid was filtered and dried to give product (480 mg, 96%). $^1$H NMR (500 MHz, DMSO-$d_6$) δ 8.69 (t, J=5.7 Hz, 1H), 8.06-8.05 (m, 1H), 7.97-7.95 (m, 1H), 7.88 (dd, J=7.4, 2.0 Hz, 1H), 7.80 (bs, 3H), 7.58-7.53 (m, 2H), 7.50-7.45 (m, 2H), 4.79 (dd, J=15.0, 5.7 Hz, 1H), 4.73 (dd, J=15.0, 5.5 Hz, 1H), 3.57-3.50 (m, 1H), 2.51-2.43 (m, 2H), 1.17 (d, J=6.5 Hz, 3H).

Example 8—Preparation of benzyl (S)-3-((tert-butoxycarbonyl)amino)-4-(((S)-4-((naphthalen-1-ylmethyl)amino)-4-oxobutan-2-yl)amino)-4-oxobutanoate (PKS2265)

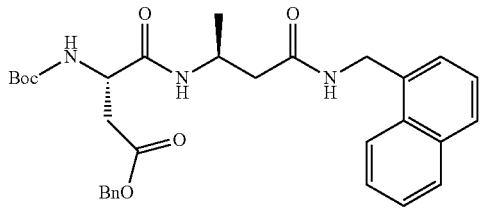 [SMILES: C[C@@H](CC(=O)NCc1cccc2ccccc12)NC(=O)[C@H](CC(=O)OCc1ccccc1)NC(=O)OC(C)(C)C]

The title compound was synthesized by following the general protocol for HATU mediated coupling of Boc-Asp(OBn)-OH (142.3 mg, 0.44 mg) and PKS2262 (143 mg, 0.40 mmol). After completion of reaction, water was added to reaction mixture to give white precipitate. Precipitate was filtered, washed with water and dried in air to give product (202 mg, 92%) as a white solid. $^1$H NMR (500 MHz, DMSO-$d_6$) δ 8.41 (t, J=5.8 Hz, 1H), 8.06-8.04 (m, 1H), 7.95-7.93 (m, 1H), 7.86 (d, J=8.3 Hz, 1H), 7.84 (d, J=7.7 Hz, 1H), 7.56-7.51 (m, 2H), 7.47-7.42 (m, 2H), 7.36-7.29 (m, 5H), 7.11 (d, J=8.3 Hz, 1H), 5.10-5.05 (m, 2H), 4.76-4.68 (m, 2H), 4.30-4.25 (m, 1H), 4.14-4.08 (m, 1H), 2.73-2.69 (m, 1H), 2.57 (dd, J=16.1, 8.8 Hz, 1H), 2.34 (dd, J=14.1, 5.6 Hz, 1H), 2.23 (dd, J=14.1, 7.5 Hz, 1H), 1.37 (s, 9H), 1.03 (d, J=6.6 Hz, 3H).

Example 9—Preparation of (S)-3-((tert-butoxycarbonyl)amino)-4-(((S)-4-((naphthalen-1-ylmethyl)amino)-4-oxobutan-2-yl)amino)-4-oxobutanoic acid (PKS2267)

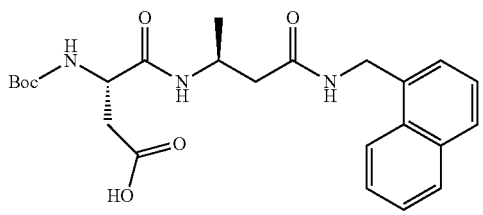 [SMILES: C[C@@H](CC(=O)NCc1cccc2ccccc12)NC(=O)[C@H](CC(=O)O)NC(=O)OC(C)(C)C]

The title compound was synthesized by following the O-debenzylation protocol of PKS2265 (202 mg, 0.37 mmol). Product (168 mg, quant.) was isolated as a white solid. $^1$H NMR (500 MHz, DMSO-$d_6$) δ 8.44-8.41 (m, 1H), 8.06-8.04 (m, 1H), 7.95-7.94 (m, 1H), 7.85 (d, J=8.0 Hz, 1H), 7.81 (d, J=8.3 Hz, 1H), 7.57-7.52 (m, 2H), 7.48-7.43 (m, 2H), 7.02 (d, J=8.2 Hz, 1H), 4.75 (dd, J=15.1, 5.7 Hz, 1H), 4.70 (dd, J=15.1, 5.7 Hz, 1H), 4.21-4.16 (m, 1H), 4.13-4.08 (m, 1H), 2.58 (dd, J=16.4, 5.1 Hz, 1H), 2.43 (dd, J=16.4, 8.5 Hz, 1H), 2.35 (dd, J=14.1, 5.4 Hz, 1H), 2.23 (dd, J=14.1, 7.7 Hz, 1H), 1.38 (s, 9H), 1.03 (d, J=6.6 Hz, 3H).

Example 10—Preparation tert-butyl ((S)-4-(tert-butylamino)-1-(((S)-4-((naphthalen-1-ylmethyl)amino)-4-oxobutan-2-yl)amino)-1,4-dioxobutan-2-yl)carbamate (PKS2247, PKS2272)

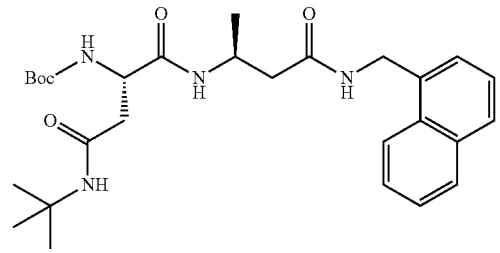 [SMILES: C[C@@H](CC(=O)NCc1cccc2ccccc12)NC(=O)[C@H](CC(=O)NC(C)(C)C)NC(=O)OC(C)(C)C]

The title compound was synthesized following the general protocol of EDC mediated coupling of PKS2267 (168 mg, 0.367 mmol) and tert-butyl amine (58 μL, 0.551 mmol). A white precipitate appeared which was filtered, washed with water and dried in air to give product (170 mg, 90%) as a white solid. $^1$H NMR (500 MHz, DMSO-$d_6$) δ 8.43 (t, J=5.6 Hz, 1H), 8.06-8.04 (m, 1H), 7.95-7.94 (m, 1H), 7.86-7.81 (m, 2H), 7.57-7.52 (m, 2H), 7.48-7.43 (m, 2H), 7.34 (s, 1H), 6.76 (d, J=8.3 Hz, 1H), 4.75 (dd, J=15.1, 5.7 Hz, 1H), 4.70 (dd, J=15.1, 5.5 Hz, 1H), 4.19-4.07 (m, 2H), 2.36-2.21 (m, 4H), 1.37 (s, 9H), 1.22 (s, 9H), 1.03 (d, J=6.6 Hz, 3H).

Example 11—Preparation of (S)-2-amino-N$^4$-(tert-butyl)-N$^1$-((S)-4-((naphthalen-1-ylmethyl)amino)-4-oxobutan-2-yl)succinamide 2,2,2-trifluoroacetate (PKS2248)

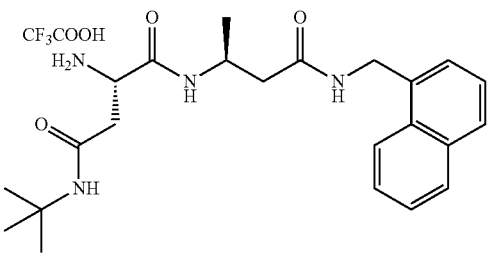 [SMILES: "CF3COOH" ; C[C@@H](CC(=O)NCc1cccc2ccccc12)NC(=O)[C@@H](N)CC(=O)NC(C)(C)C]

The title compound was prepared by following the general protocol for Boc-Deprotection of PKS2272 (62 mg, 0.12 mmol). The crude was treated with diethyl ether and kept standing 3 hours. The white solid was filtered and dried to give product (60 mg, 95%). $^1$H NMR (500 MHz, DMSO-$d_6$) δ 8.47 (t, J=5.6 Hz, 1H), 8.32 (d, J=7.9 Hz, 1H), 8.06-8.03 (m, 4H), 7.96-7.95 (m, 1H), 7.87-7.85 (m, 1H), 7.80 (s, 1H), 7.57-7.53 (m, 2H), 7.49-7.43 (m, 2H), 4.78 (dd, J=15.1, 5.8 Hz, 1H), 4.69 (dd, J=15.1, 5.4 Hz, 1H), 4.21-4.13 (m, 1H), 3.95 (m, 1H), 2.60 (dd, J=16.7, 4.6 Hz, 1H), 2.55-2.49 (m, 1H), 2.34 (dd, J=14.1, 5.7 Hz, 1H), 2.26 (dd, J=14.1, 8.0 Hz, 1H), 1.26 (s, 9H), 1.07 (d, J=6.6 Hz, 3H).

Example 12—Preparation of (S)—N⁴-(tert-butyl)-2-(5-methylisoxazole-3-carboxamido)-N¹—((S)-4-((naphthalen-1-ylmethyl)amino)-4-oxobutan-2-yl)succinamide (PKS2249)

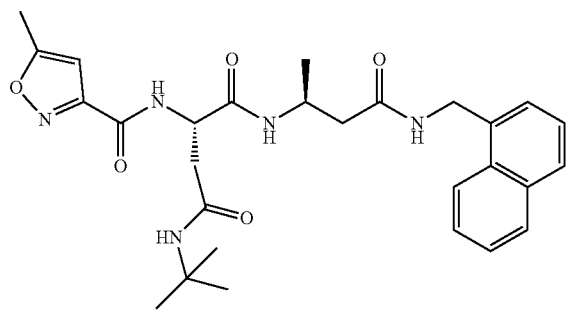 [SMILES: Cc1cc(C(=O)N[C@@H](CC(=O)NC(C)(C)C)C(=O)N[C@@H](C)CC(=O)NCc2cccc3ccccc23)no1]

The title compound was prepared by following the general protocol for HATU mediated coupling of 5-methylisoxazole-3-carboxylic acid (5.6 mg, 0.044 mmol) and PKS2248 (21.1 mg, 0.04 mmol). After completion of reaction, the mixture was purified by HPLC to give pure product (14.4 mg, 69%) as a white solid. $^1$H NMR (500 MHz, DMSO-d$_6$) δ 8.50 (d, J=8.1 Hz, 1H), 8.41 (t, J=5.7 Hz, 1H), 8.05-8.03 (m, 1H), 7.99 (d, J=8.1 Hz, 1H), 7.95-7.93 (m, 1H), 7.84 (d, J=8.0 Hz, 1H), 7.57-7.51 (m, 2H), 7.48-7.42 (m, 3H), 6.53 (s, 1H), 4.74 (dd, J=15.1, 5.7 Hz, 1H), 4.68 (dd, J=15.1, 5.5 Hz, 1H), 4.63 (td, J=8.4, 4.8 Hz, 1H), 4.16-4.08 (m, 1H), 2.54 (dd, J=14.3, 8.7 Hz, 1H), 2.45 (s, 3H), 2.41 (dd, J=14.3, 4.8 Hz, 1H), 2.35 (dd, J=14.0, 5.7 Hz, 1H), 2.25 (dd, J=14.0, 7.7 Hz, 1H), 1.18 (s, 9H), 1.04 (d, J=6.6 Hz, 3H). $^{13}$C NMR (126 MHz, DMSO) δ 171.34, 169.90, 169.22, 168.86, 158.58, 158.24, 134.57, 133.32, 130.89, 128.53, 127.62, 126.25, 125.85, 125.62, 125.43, 123.52, 101.35, 50.51, 50.14, 42.57, 41.61, 40.19, 38.33, 28.38, 19.98, 11.86.

Example 13—Preparation of (S)—N⁴-(tert-butyl)-N¹—((S)-4-((naphthalen-1-ylmethyl)amino)-4-oxobutan-2-yl)-2-(3-phenylpropanamido)succinamide (PKS2251)

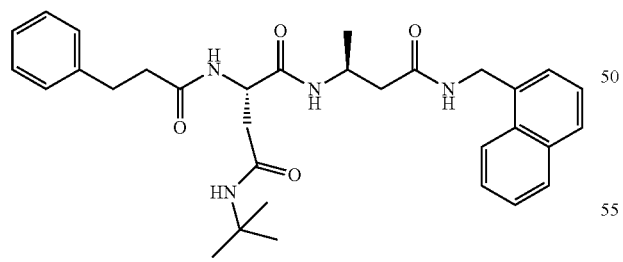

The title compound was prepared by following the general protocol for HATU mediated coupling of 3-phenylpropanoic acid (5.0 mg, 0.033 mmol) and PKS2248 (15.8 mg, 0.03 mmol). After completion of reaction, the mixture was purified by HPLC to give pure product (14.3 mg, 88%) as a white solid. $^1$H NMR (500 MHz, DMSO-d$_6$) δ 8.44 (t, J=5.7 Hz, 1H), 8.06-8.04 (m, 1H), 7.99 (d, J=8.1 Hz, 1H), 7.95-7.93 (m, 1H), 7.86-7.83 (m, 2H), 7.57-7.53 (m, 2H), 7.49-7.43 (m, 2H), 7.33 (s, 1H), 7.26-7.23 (m, 2H), 7.20-7.14 (m, 3H), 4.75 (dd, J=15.1, 5.7 Hz, 1H), 4.71 (dd, J=15.1, 5.6 Hz, 1H), 4.48 (td, J=8.2, 5.6 Hz, 1H), 4.14-4.06 (m, 1H), 2.82-2.78 (m, 2H), 2.44-2.33 (m, 4H), 2.29 (dd, J=14.6, 8.3 Hz, 1H), 2.23 (dd, J=14.1, 7.8 Hz, 1H), 1.21 (s, 9H), 1.03 (d, J=6.6 Hz, 3H). $^{13}$C NMR (126 MHz, DMSO) δ 171.10, 169.97, 169.92, 168.75, 141.31, 134.56, 133.28, 130.86, 128.49, 128.25, 128.11, 127.57, 126.19, 125.82, 125.79, 125.56, 125.38, 123.48, 50.10, 50.02, 42.32, 41.50, 40.15, 38.73, 36.89, 31.00, 28.44, 19.87.

Example 14—Preparation of (S)—N⁴-(tert-butyl)-2-((4-methylphenyl)sulfonamido)-N¹—((S)-4-((naphthalen-1-ylmethyl)amino)-4-oxobutan-2-yl)succinamide (PKS2252)

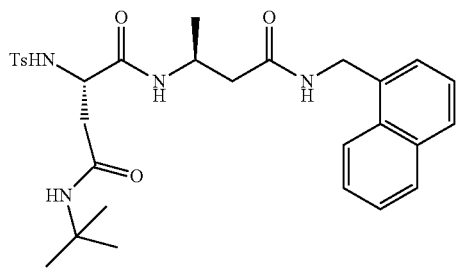

The title compound was prepared by following the general procedure for N-sulfonamide formation of PKS2248 (21.1 mg, 0.04 mmol) with tosyl chloride (11.5 mg, 0.06 mmol). The product was isolated as white solid (12.7 mg, 56%) after HPLC purification. $^1$H NMR (500 MHz, DMSO-d$_6$) δ 8.38 (t, J=5.7 Hz, 1H), 8.05-8.03 (m, 1H), 7.95-7.93 (m, 1H), 7.84 (d, J=8.1 Hz, 1H), 7.78 (d, J=8.1 Hz, 1H), 7.71 (bs, 1H), 7.65 (d, J=8.2 Hz, 2H), 7.56-7.52 (m, 2H), 7.48-7.41 (m, 2H), 7.32-7.29 (m, 3H), 4.73 (dd, J=15.1, 5.7 Hz, 1H), 4.68 (dd, J=15.1, 5.6 Hz, 1H), 4.01 (m, 1H), 3.94-3.85 (m, 1H), 2.33 (s, 3H), 2.29-2.15 (m, 3H), 2.11 (dd, J=14.1, 8.2 Hz, 1H), 1.18 (s, 9H), 0.83 (d, J=6.6 Hz, 3H). $^{13}$C NMR (126 MHz, DMSO) δ 169.67, 168.87, 168.02, 142.36, 138.33, 134.59, 133.28, 130.86, 129.24, 128.48, 127.57, 126.63, 126.17, 125.79, 125.60, 125.37, 123.50, 53.60, 50.07, 42.18, 41.52, 40.13, 39.39, 28.40, 20.91, 19.43.

Example 15—Preparation of (S)—N⁵-(tert-butyl)-N¹—((S)-4-((naphthalen-1-ylmethyl)amino)-4-oxobutan-2-yl)-2-(3-phenylpropanamido)pentanediamide (PKS2253)

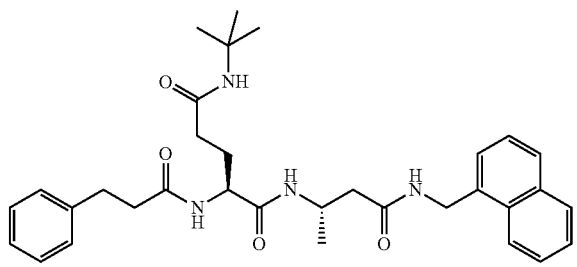 [SMILES: C[C@@H](CC(=O)NCc1cccc2ccccc12)NC(=O)[C@H](CCC(=O)NC(C)(C)C)NC(=O)CCc1ccccc1]

The title compound was synthesized by following the general protocol for HATU mediated coupling of PhCH$_2$CH$_2$C(O)-Glu(NHtBu)-OH (18.4 mg, 0.055 mmol) and H-β-homo-Ala-CH$_2$-naphth TFA salt (17.8 mg, 0.05 mmol). Purification by HPLC provided the product (23.5 mg, 84%) as a white solid. $^1$H NMR (500 MHz, DMSO-d$_6$) δ 8.45 (t, J=5.7 Hz, 1H), 8.07-8.05 (m, 1H), 8.00-7.93 (m, 2H), 7.89 (d, J=8.1 Hz, 1H), 7.85-7.83 (m, 1H), 7.57-7.51 (m, 2H), 7.48-7.43 (m, 2H), 7.34 (s, 1H), 7.27-7.23 (m, 2H), 7.21-7.14 (m, 3H), 4.77 (dd, J=15.1, 5.7 Hz, 1H), 4.70 (dd, J=15.1, 5.6 Hz, 1H), 4.18-4.13 (m, 2H), 2.81 (t, J=7.9 Hz, 2H), 2.46-2.42 (m, 2H), 2.38 (dd, J=14.0, 5.6 Hz, 1H), 2.24 (dd, J=14.0, 7.8 Hz, 1H), 1.99 (t, J=8.1 Hz, 2H), 1.82-1.75 (m, 1H), 1.70-1.62 (m, 1H), 1.21 (s, 9H), 1.05 (d, J=6.6 Hz, 3H). $^{13}$C NMR (126 MHz, DMSO) δ 171.24, 171.08, 170.30, 169.92, 141.35, 134.54, 133.28, 130.85, 128.48, 128.22, 128.16, 127.56, 126.19, 125.80, 125.52, 125.39, 123.49, 52.30, 49.80, 42.27, 41.82, 40.14, 36.78, 32.57, 31.06, 28.54, 28.51, 20.12.

Example 16—Preparation of (S)—N-(tert-butyl)-N$^1$—((S)-4-((naphthalen-1-ylmethyl)amino)-4-oxobutan-2-yl)-2-(phenylsulfonamido)succinamide (PKS2260)

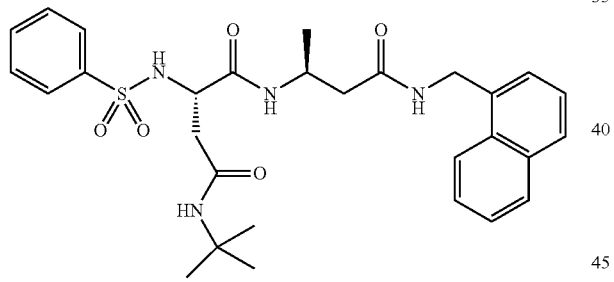

The title compound was prepared by following the general procedure for N-sulfonamide formation of PKS2248 (12.1 mg, 0.023 mmol) with phenylsulfonyl chloride (4 µL, 0.028 mmol). The product was isolated as a white solid (10.0 mg, 79%) after HPLC purification. $^1$H NMR (500 MHz, DMSO-d$_6$) δ 8.37 (t, J=5.7 Hz, 1H), 8.04-8.02 (m, 1H), 7.95-7.93 (m, 1H), 7.85-7.81 (m, 3H), 7.77 (d, J=7.6 Hz, 2H), 7.60-7.41 (m, 7H), 7.32 (s, 1H), 4.73 (dd, J=15.1, 5.8 Hz, 1H), 4.68 (dd, J=15.1, 5.5 Hz, 1H), 4.07-4.03 (m, 1H), 3.92-3.86 (m, 1H), 2.28-2.17 (m, 3H), 2.12 (dd, J=14.1, 8.3 Hz, 1H), 1.18 (s, 9H), 0.83 (d, J=6.6 Hz, 3H). $^{13}$C NMR (126 MHz, DMSO-d$_6$) δ 169.67, 168.85, 167.98, 141.25, 134.59, 133.28, 132.17, 130.86, 128.80, 128.48, 127.57, 126.54, 126.19, 125.80, 125.60, 125.38, 123.50, 53.62, 50.07, 42.16, 41.55, 40.13, 39.69, 28.42, 19.49.

Example 17—Preparation of (S)—N$^4$-(tert-butyl)-2-(cyclopropanesulfonamido)-N$^1$—((S)-4-((naphthalen-1-ylmethyl)amino)-4-oxobutan-2-yl)succinamide (PKS2295)

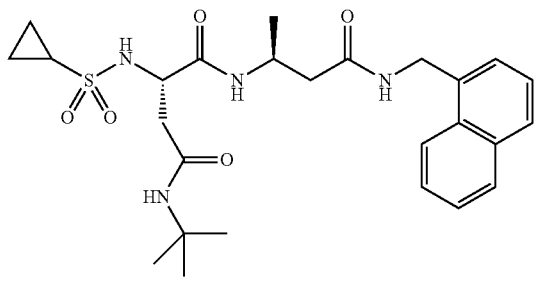 [SMILES: C[C@@H](CC(=O)NCc1cccc2ccccc12)NC(=O)[C@H](CC(=O)NC(C)(C)C)NS(=O)(=O)C1CC1]

The title compound was prepared by following the general procedure for N-sulfonamide formation of PKS2248 (21.1 mg, 0.04 mmol) with cyclopropylsulfonyl chloride (6 µL, 0.06 mmol). The product was isolated as a white solid (16.3 mg, 79%) after HPLC purification. $^1$H NMR (500 MHz, DMSO-d$_6$) δ 8.42 (t, J=5.6 Hz, 1H), 8.06-8.04 (m, 1H), 7.97-7.94 (m, 2H), 7.85 (d, J=7.9 Hz, 1H), 7.57-7.52 (m, 2H), 7.48-7.43 (m, 2H), 7.40 (s, 1H), 7.26 (d, J=9.1 Hz, 1H), 4.75 (dd, J=15.1, 5.7 Hz, 1H), 4.70 (dd, J=15.1, 5.5 Hz, 1H), 4.17-4.06 (m, 2H), 2.50-2.46 (m, 1H), 2.41-2.32 (m, 3H), 2.25 (dd, J=14.1, 8.0 Hz, 1H), 1.23 (s, 9H), 1.04 (d, J=6.6 Hz, 3H), 0.90-0.82 (m, 4H). $^{13}$C NMR (126 MHz, DMSO-d$_6$) δ 169.93, 169.75, 168.37, 134.57, 133.28, 130.87, 128.48, 127.58, 126.19, 125.80, 125.62, 125.38, 123.51, 53.71, 50.12, 42.41, 41.59, 40.15, 39.82, 30.28, 28.45, 19.80, 5.13, 4.84.

Example 18—Preparation of benzyl (R)-3-((tert-butoxycarbonyl)amino)-5-(((S)-1-((naphthalen-1-ylmethyl)amino)-1-oxopropan-2-yl)amino)-5-oxopentanoate (PKS2266)

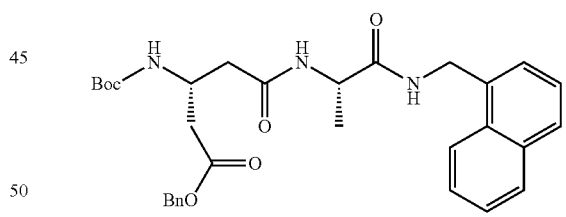

The title compound was synthesized by following the general protocol for HATU mediated coupling of N-Boc-L-β-glutamic acid 5-benzyl ester (84 mg, 0.25 mmol) and H-Ala-CH$_2$-naphth TFA salt (94 mg, 0.275 mmol). After completion of reaction, water was added to reaction mixture to give white precipitate. Precipitate was filtered, washed with water and dried in air to give product (115 mg, 84%) as a white solid. $^1$H NMR (500 MHz, DMSO-d$_6$) δ 8.40 (t, J=5.6 Hz, 1H), 8.11 (d, J=7.4 Hz, 1H), 8.04-8.02 (m, 1H), 7.95-7.93 (m, 1H), 7.83 (d, J=7.9 Hz, 1H), 7.56-7.51 (m, 2H), 7.47-7.41 (m, 2H), 7.37-7.30 (m, 5H), 6.82 (d, J=8.3 Hz, 1H), 5.05 (s, 2H), 4.77-4.69 (m, 2H), 4.33-4.28 (m, 1H), 4.22-4.13 (m, 1H), 2.55 (dd, J=15.0, 5.0 Hz, 1H), 2.49-2.44 (m, 1H), 2.38 (dd, J=14.6, 6.3 Hz, 1H), 2.32 (dd, J=14.6, 7.5 Hz, 1H), 1.34 (s, 9H), 1.21 (d, J=7.1 Hz, 3H).

Example 19—Preparation of (R)-3-((tert-butoxycarbonyl)amino)-5-(((S)-1-((naphthalen-1-ylmethyl)amino)-1-oxopropan-2-yl)amino)-5-oxopentanoic-acid (PKS2268)

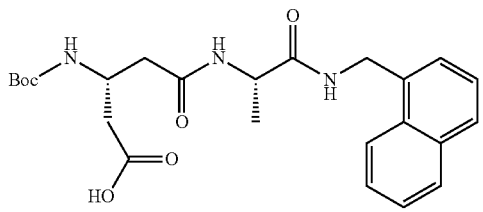 [SMILES: C[C@H](NC(=O)C[C@H](CC(=O)O)NC(=O)OC(C)(C)C)C(=O)NCc1cccc2ccccc12]

The title compound was synthesized by following the O-debenzylation protocol of PKS2266 (110 mg, 0.2 mmol). Product (92 mg, quant.) was isolated as a white solid. $^1$H NMR (500 MHz, DMSO-d$_6$) δ 8.49 (t, J=5.8 Hz, 1H), 8.16 (d, J=7.4 Hz, 1H), 8.04 (d, J=7.8 Hz, 1H), 7.94 (d, J=7.3 Hz, 1H), 7.83 (d, J=7.8 Hz, 1H), 7.56-7.51 (m, 2H), 7.48-7.42 (m, 2H), 6.74 (d, J=8.2 Hz, 1H), 4.74-4.71 (m, 2H), 4.33-4.28 (m, 1H), 4.11-4.04 (m, 1H), 2.41-2.29 (m, 4H), 1.35 (s, 9H), 1.23 (d, J=7.1 Hz, 3H).

Example 20—Preparation of tert-butyl ((R)-1-(tert-butylamino)-5-(((S)-1-((naphthalen-1-ylmethyl)amino)-1-oxopropan-2-yl)amino)-1,5-dioxopentan-3-yl)carbamate (PKS2271)

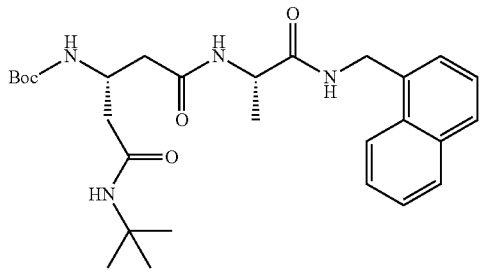 [SMILES: C[C@H](NC(=O)C[C@H](CC(=O)NC(C)(C)C)NC(=O)OC(C)(C)C)C(=O)NCc1cccc2ccccc12]

The title compound was prepared by following the general protocol for EDC mediated coupling of PKS2268 (92 mg, 0.2 mmol) and tert-butylamine (31.5 μL, 0.3 mmol). After completion of reaction, water was added to reaction mixture to give white precipitate. Precipitate was filtered, washed with water and dried in air to give product (85 mg, 83%) as a white solid. $^1$H NMR (500 MHz, DMSO-d$_6$) δ 8.44 (t, J=5.9 Hz, 1H), 8.05-8.03 (m, 2H), 7.95-7.93 (m, 1H), 7.84 (d, J=7.7 Hz, 1H), 7.56-7.53 (m, 2H), 7.48-7.43 (m, 2H), 7.34 (s, 1H), 6.56 (d, J=8.4 Hz, 1H), 4.78-4.69 (m, 2H), 4.34-4.28 (m, 1H), 4.10-4.00 (m, 1H), 2.36-2.12 (m, 4H), 1.35 (s, 9H), 1.23-1.22 (m, 12H).

Example 21—Preparation of (R)-3-amino-N'-(tert-butyl)-N$^5$—((S)-1-((naphthalen-1-ylmethyl)amino)-1-oxopropan-2-yl)pentanediamide 2,2,2-trifluoroacetate (PKS2273)

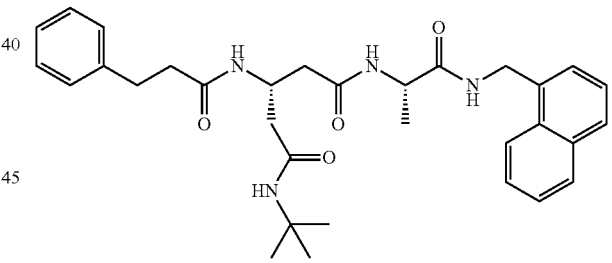

The title compound was synthesized by following the general protocol for Boc-deprotection of PKS2271 (80 mg, 0.156 mmol). $^1$H NMR (500 MHz, DMSO-d$_6$) δ 8.54 (t, J=5.7 Hz, 1H), 8.46 (d, J=7.3 Hz, 1H), 8.05-8.03 (m, 1H), 7.96-7.94 (m, 1H), 7.89-7.82 (m, 5H), 7.56-7.54 (m, 2H), 7.49-7.43 (m, 2H), 4.78 (dd, J=15.4, 5.9 Hz, 1H), 4.70 (dd, J=15.4, 5.5 Hz, 1H), 4.39-4.33 (m, 1H), 3.67-3.61 (m, 1H), 2.53-2.49 (m, 2H), 2.42 (dd, J=15.9, 5.8 Hz, 1H), 2.36 (dd, J=15.9, 7.2 Hz, 1H), 1.26-1.24 (m, 12H).

Example 22—Preparation of (R)—N$^1$-(tert-butyl)-N$^5$—((S)-1-((naphthalen-1-ylmethyl)amino)-1-oxopropan-2-yl)-3-(3-phenylpropanamido)pentanediamide (PKS2278)

The title compound was synthesized by following the general protocol for HATU mediated coupling of 3-phenylproapnoic acid (6.6 mg, 0.044 mmol) and PKS2273 (21.1 mg, 0.04 mmol). After completion of reaction, mixture was purified by HPLC to give pure product (20.7 mg, 95%) as a white solid. $^1$H NMR (500 MHz, DMSO-d$_6$) δ 8.44-8.42 (m, 1H), 8.07 (d, J=7.3 Hz, 1H), 8.02-8.00 (m, 1H), 7.95-7.93 (m, 1H), 7.83 (d, J=7.9 Hz, 1H), 7.68 (d, J=8.1 Hz, 1H), 7.54-7.52 (m, 2H), 7.45-7.39 (m, 2H), 7.37 (s, 1H), 7.24-7.21 (m, 2H), 7.16-7.13 (m, 3H), 4.71 (d, J=5.7 Hz, 2H), 4.33-4.29 (m, 2H), 2.76-2.73 (m, 2H), 2.37-2.16 (m, 6H), 1.24-1.22 (m, 12H). $^{13}$C NMR (126 MHz, DMSO) δ 172.36, 170.51, 169.71, 169.42, 141.31, 134.41, 133.21, 130.74, 128.46, 128.23, 128.07, 127.39, 126.12, 125.79, 125.73, 125.37, 124.90, 123.32, 49.96, 48.42, 44.21, 40.73, 40.11, 39.75, 37.21, 31.14, 28.45, 18.27.

Example 23—Preparation of (R)—N¹-(tert-butyl)-3-(4-methylphenylsulfonamido)-N—((S)-1-((naphthalen-1-ylmethyl)amino)-1-oxopropan-2-yl)pentanediamide (PKS2279)

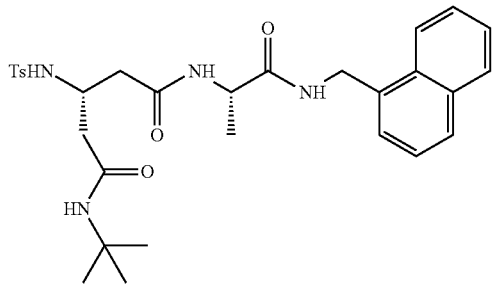

The title compound was prepared by following the general procedure for N-sulfonamide formation of PKS2273 (21.1 mg, 0.04 mmol) with tosyl chloride (11.4 mg, 0.06 mmol). The product was isolated as a white solid (17.8 mg, 78%) after HPLC purification. $^1$H NMR (500 MHz, DMSO-d$_6$) δ 8.42 (t, J=5.8 Hz, 1H), 8.08-8.03 (m, 2H), 7.95-7.94 (m, 1H), 7.84 (d, J=7.9 Hz, 1H), 7.66 (d, J=8.1 Hz, 2H), 7.55-7.53 (m, 2H), 7.48-7.42 (m, 3H), 7.39 (s, 1H), 7.32 (d, J=8.1 Hz, 2H), 4.78-4.70 (m, 2H), 4.28-4.23 (m, 1H), 3.81-3.74 (m, 1H), 2.35 (s, 3H), 2.29-2.20 (m, 2H), 2.13 (d, J=6.6 Hz, 2H), 1.20-1.18 (m, 12H). $^{13}$C NMR (126 MHz, DMSO) δ 172.19, 169.22, 168.94, 142.43, 138.54, 134.41, 133.24, 130.77, 129.45, 128.48, 127.46, 126.50, 126.14, 125.77, 125.38, 125.07, 123.37, 50.05, 48.51, 48.30, 40.71, 40.13, 39.95, 28.39, 20.94, 18.26.

Example 24—Preparation of (S)-benzyl 4-((tert-butoxycarbonyl)amino)-6-(((S)-1-((naphthalen-1-ylmethyl)amino)-1-oxopropan-2-yl)amino)-6-oxohexanoate (PKS2274)

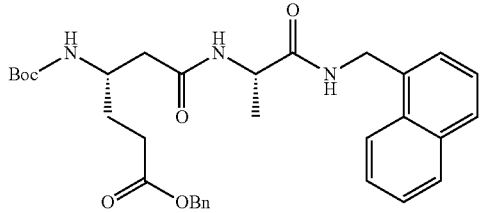 [SMILES: C[C@H](NC(=O)C[C@H](CCC(=O)OCc1ccccc1)NC(=O)OC(C)(C)C)C(=O)NCc1cccc2ccccc12]

The title compound was synthesized by following the general protocol for HATU mediated coupling of (S)-3-(Boc-amino)adipic acid 6-benzyl ester (23.7 mg, 0.0675 mmol) and H-Ala-CH$_2$-naphth TFA salt (23.1 mg, 0.0675 mmol). After completion of reaction, mixture was purified by HPLC to give product (23.0 mg, 61%) as a white solid. $^1$H NMR (500 MHz, Chloroform-d) δ 7.96 (d, J=8.3 Hz, 1H), 7.86-7.84 (m, 1H), 7.78 (dd, J=7.3, 2.1 Hz, 1H), 7.55-7.47 (m, 2H), 7.42-7.38 (m, 2H), 7.36-7.28 (m, 5H), 6.66-6.64 (m, 1H), 6.24 (d, J=7.2 Hz, 1H), 5.13 (d, J=8.9 Hz, 1H), 5.05-5.00 (m, 2H), 4.91 (dd, J=14.6, 5.6 Hz, 1H), 4.84 (dd, J=14.6, 5.3 Hz, 1H), 4.45-4.39 (m, 1H), 3.75-3.70 (m, 1H), 2.37-2.23 (m, 4H), 1.73-1.61 (m, 2H), 1.39 (s, 9H), 1.37 (d, J=7.0 Hz, 3H).

Example 25—Preparation of (S)-4-((tert-butoxycarbonyl)amino)-6-(((S)-1-((naphthalen-1-ylmethyl)amino)-1-oxopropan-2-yl)amino)-6-oxohexanoic acid (PKS2277)

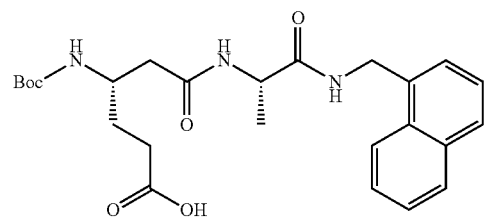 [SMILES: C[C@H](NC(=O)C[C@H](CCC(=O)O)NC(=O)OC(C)(C)C)C(=O)NCc1cccc2ccccc12]

The title compound was synthesized by following the O-debenzylation protocol of PKS2274 (23 mg, 0.04 mmol). The crude was purified by HPLC to give product (17.5 mg, 91%) as a white solid. $^1$H NMR (500 MHz, DMSO-d$_6$) δ 8.44 (t, J=5.8 Hz, 1H), 8.13-8.11 (m, 1H), 8.04 (d, J=7.9 Hz, 1H), 7.95-7.93 (m, 1H), 7.84 (d, J=7.8 Hz, 1H), 7.56-7.51 (m, 2H), 7.48-7.42 (m, 2H), 6.71 (d, J=8.8 Hz, 1H), 4.72-4.71 (m, 2H), 4.33-4.31 (m, 1H), 3.75 (m, 1H), 2.32-2.14 (m, 4H), 1.70-1.65 (m, 1H), 1.57-1.51 (m, 1H), 1.36 (s, 9H), 1.22 (d, J=7.2 Hz, 3H).

Example 26—Preparation of tert-butyl ((S)-6-(tert-butylamino)-1-(((S)-1-((naphthalen-1-ylmethyl)amino)-1-oxopropan-2-yl)amino)-1,6-dioxohexan-3-yl)carbamate (PKS2282)

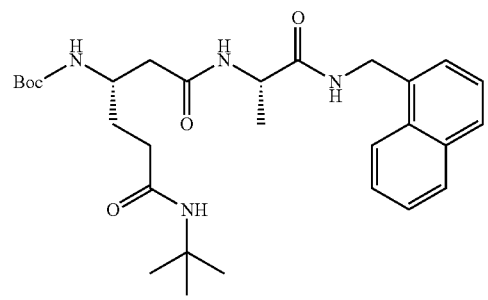 [SMILES: C[C@H](NC(=O)C[C@H](CCC(=O)NC(C)(C)C)NC(=O)OC(C)(C)C)C(=O)NCc1cccc2ccccc12]

Title compound was prepared by following the general protocol for EDC mediated coupling of PKS2277 (17.5 mg, 0.037 mmol) and tert-butylamine (6.0 µL, 0.056 mmol). After completion of reaction, mixture was purified by HPLC to give product (6.8 mg, 35%) as a white solid. $^1$H NMR (500 MHz, DMSO-d$_6$) δ 8.42 (t, J=5.8 Hz, 1H), 8.07-8.03 (m, 2H), 7.95-7.93 (m, 1H), 7.84 (d, J=7.9 Hz, 1H), 7.56-7.53 (m, 2H), 7.48-7.42 (m, 2H), 7.33 (s, 1H), 6.61 (d, J=8.7 Hz, 1H), 4.78-4.69 (m, 2H), 4.35-4.29 (m, 1H), 3.75-3.68 (m, 1H), 2.31-2.22 (m, 2H), 2.02-1.97 (m, 2H), 1.62-1.57 (m, 1H), 1.53-1.48 (m, 1H), 1.36 (s, 9H), 1.23-1.21 (m, 12H).

Example 27—Preparation of (S)-3-amino-N⁶-(tert-butyl)-N¹—((S)-1-((naphthalen-1-ylmethyl)amino)-1-oxopropan-2-yl)hexanediamide 2,2,2-trifluoroacetate (PKS2289)

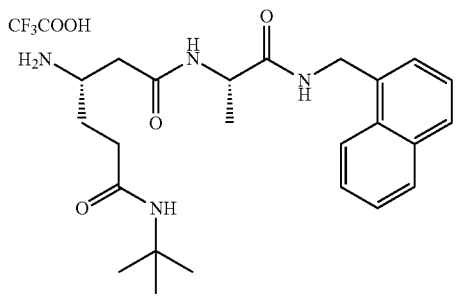 [SMILES: "CF3COOH" ; C[C@H](NC(=O)C[C@@H](N)CCC(=O)NC(C)(C)C)C(=O)NCc1cccc2ccccc12]

The title compound was synthesized by following the general protocol for Boc-deprotection of PKS2282 (6.8 mg, 0.013 mmol). The product was used in next step without further purification. $^1$H NMR (500 MHz, Chloroform-d) δ 8.24 (s, 3H), 8.10 (m, 1H), 7.88-7.80 (m, 3H), 7.55-7.49 (m, 2H), 7.42-7.40 (m, 2H), 6.82 (m, 1H), 5.98 (s, 1H), 5.00-4.95 (m, 1H), 4.76-4.72 (m, 1H), 4.37 (m, 1H), 3.55 (m, 1H), 2.75-2.72 (m, 1H), 2.61-2.57 (m, 1H), 2.40 (t, J=5.4 Hz, 2H), 1.93 (m, 1H), 1.80 (m, 1H), 1.39-1.38 (m, 3H), 1.32 (s, 9H).

Example 28—Preparation of (S)—N⁶-(tert-butyl)-3-(4-methylphenylsulfonamido)-N¹—((S)-1-((naphthalen-1-ylmethyl)amino)-1-oxopropan-2-yl)hexanediamide (PKS2290)

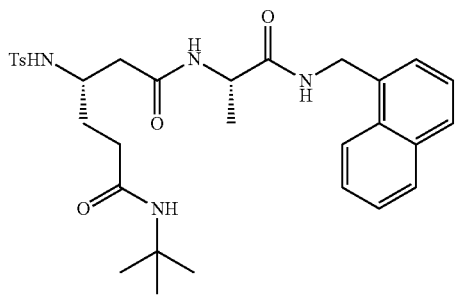

The title compound was prepared by following the general procedure for N-sulfonamide formation of PKS2289 (crude from previous step, 0.013 mmol) with tosyl chloride (5.0 mg, 0.026 mmol). The product was isolated as a white solid (6.0 mg, 79% for 2 steps) after HPLC purification. $^1$H NMR (500 MHz, DMSO-d$_6$) δ 8.41 (t, J=5.8 Hz, 1H), 8.10 (d, J=7.5 Hz, 1H), 8.03-8.01 (m, 1H), 7.96-7.94 (m, 1H), 7.84 (d, J=8.0 Hz, 1H), 7.66 (d, J=8.2 Hz, 2H), 7.59 (d, J=7.8 Hz, 1H), 7.55-7.52 (m, 2H), 7.47-7.40 (m, 2H), 7.35 (d, J=8.0 Hz, 2H), 7.31 (s, 1H), 4.74 (dd, J=15.4, 5.8 Hz, 1H), 4.70 (dd, J=15.4, 5.7 Hz, 1H), 4.28-4.22 (m, 1H), 3.45-3.39 (m, 1H), 2.36 (s, 3H), 2.20-2.00 (m, 3H), 1.94-1.88 (m, 1H), 1.57-1.50 (m, 1H), 1.47-1.39 (m, 1H), 1.20 (s, 9H), 1.18 (d, J=7.4 Hz, 4H). $^{13}$C NMR (126 MHz, DMSO) δ 172.13, 171.40, 169.29, 142.40, 138.78, 134.41, 133.23, 130.76, 129.54, 128.47, 127.44, 126.37, 126.12, 125.76, 125.37, 124.98, 123.35, 50.76, 49.80, 48.19, 40.72, 40.13, 32.47, 30.27, 28.47, 20.96, 18.27.

Example 29—Preparation of (R)-benzyl 3-((tert-butoxycarbonyl)amino)-5-(((S)-4-((naphthalen-1-ylmethyl)amino)-4-oxobutan-2-yl)amino)-5-oxopentanoate (PKS2281)

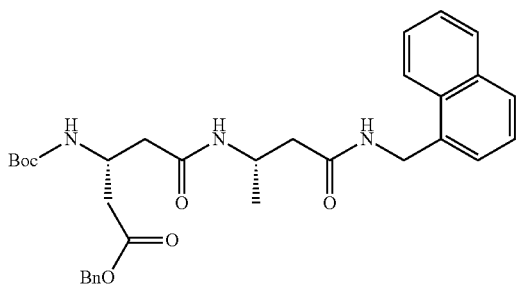 [SMILES: C[C@@H](CC(=O)NCc1cccc2ccccc12)NC(=O)C[C@H](CC(=O)OCc1ccccc1)NC(=O)OC(C)(C)C]

The title compound was synthesized by following the general protocol for HATU mediated coupling of N-Boc-L-beta-glutamic acid 5-benzyl ester (47 mg, 0.14 mmol) and H-homo-β-Ala-CH$_2$-naphth TFA salt (50 mg, 0.14 mmol). The reaction mixture was purified by HPLC to give product (73 mg, 93%) as a white solid. $^1$H NMR (500 MHz, DMSO-d$_6$) δ 8.39 (t, J=5.5 Hz, 1H), 8.06-8.04 (m, 1H), 7.95-7.93 (m, 1H), 7.84 (d, J=7.9 Hz, 1H), 7.81 (d, J=8.0 Hz, 1H), 7.56-7.51 (m, 2H), 7.48-7.42 (m, 2H), 7.37-7.30 (m, 5H), 6.79 (d, J=8.5 Hz, 1H), 5.05 (s, 2H), 4.76-4.68 (m, 2H), 4.16-4.09 (m, 2H), 2.55-2.43 (m, 2H), 2.36 (dd, J=14.0, 5.7 Hz, 1H), 2.26-2.17 (m, 3H), 1.35 (s, 9H), 1.02 (d, J=6.0 Hz, 3H).

Example 30—Preparation of (R)-3-((tert-butoxycarbonyl)amino)-5-(((S)-4-((naphthalen-1-ylmethyl)amino)-4-oxobutan-2-yl)amino)-5-oxopentanoic acid (PKS2285)

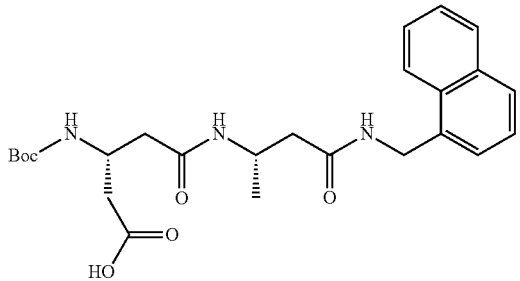 [SMILES: C[C@@H](CC(=O)NCc1cccc2ccccc12)NC(=O)C[C@H](CC(=O)O)NC(=O)OC(C)(C)C]

The title compound was synthesized by following the O-debenzylation protocol of PKS2281 (73 mg, 0.13 mmol). Yield 61.0 mg (quant.). $^1$H NMR (500 MHz, DMSO-d$_6$) δ 12.12 (s, 1H), 8.39 (t, J=5.6 Hz, 1H), 8.06-8.04 (m, 1H), 7.95-7.93 (m, 1H), 7.85 (d, J=8.0 Hz, 1H), 7.79 (d, J=8.0 Hz, 1H), 7.56-7.52 (m, 2H), 7.48-7.42 (m, 2H), 6.69 (d, J=8.4 Hz, 1H), 4.77-4.68 (m, 2H), 4.15-4.01 (m, 2H), 2.38-2.34 (m, 3H), 2.26-2.16 (m, 3H), 1.36 (s, 9H), 1.02 (d, J=6.6 Hz, 3H).

Example 31—Preparation of tert-butyl ((R)-1-(tert-butylamino)-5-(((S)-4-((naphthalen-1-ylmethyl)amino)-4-oxobutan-2-yl)amino)-1,5-dioxopentan-3-yl)carbamate (PKS2286)

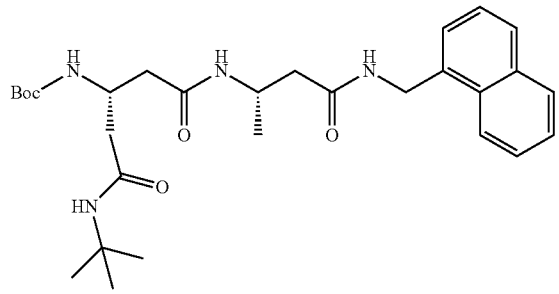 [SMILES: C[C@@H](CC(=O)NCc1cccc2ccccc12)NC(=O)C[C@H](CC(=O)NC(C)(C)C)NC(=O)OC(C)(C)C]

The title compound was prepared by following the general protocol for EDC mediated coupling of PKS2285 (61.0 mg, 0.13 mmol) and tert-butylamine (20.0 µL, 0.195 mmol). After completion of reaction, mixture was purified by HPLC to give product (13.0 mg, 19%) as a white solid. $^1$H NMR (500 MHz, DMSO-$d_6$) δ 8.41 (t, J=5.6 Hz, 1H), 8.06-8.04 (m, 1H), 7.95-7.93 (m, 1H), 7.84 (d, J=7.7 Hz, 1H), 7.72 (d, J=8.1 Hz, 1H), 7.56-7.51 (m, 2H), 7.48-7.43 (m, 2H), 7.31 (s, 1H), 6.50 (d, J=8.7 Hz, 1H), 4.77-4.68 (m, 2H), 4.18-4.10 (m, 1H), 4.06-3.98 (m, 1H), 2.36 (dd, J=13.9, 5.6 Hz, 1H), 2.22-2.14 (m, 5H), 1.36 (s, 9H), 1.22 (s, 9H), 1.02 (d, J=6.5 Hz, 3H).

Example 32—Preparation of (R)-3-amino-N'-(tert-butyl)-N$^5$—((S)-4-((naphthalen-1-ylmethyl)amino)-4-oxobutan-2-yl)pentanediamide 2,2,2-trifluoroacetate (PKS2288)

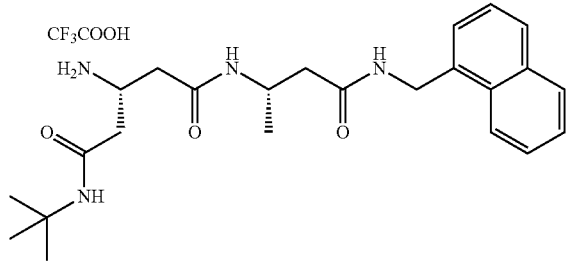 [SMILES: "CF3COOH" ; C[C@@H](CC(=O)NCc1cccc2ccccc12)NC(=O)C[C@@H](N)CC(=O)NC(C)(C)C]

The title compound was synthesized by following the general protocol for Boc-deprotection of PKS2286 (13.0 mg, 0.025 mmol). Yield 13.5 mg (quant.). $^1$H NMR (500 MHz, Chloroform-d) δ 8.65 (bs, 3H), 8.47 (d, J=7.9 Hz, 1H), 7.94 (d, J=8.3 Hz, 1H), 7.86 (d, J=8.1 Hz, 1H), 7.82-7.78 (m, 1H), 7.57-7.49 (m, 2H), 7.43-7.40 (m, 2H), 6.52 (t, J=5.3 Hz, 1H), 5.98 (s, 1H), 4.81-4.74 (m, 2H), 4.35-4.30 (m, 1H), 3.86 (m, 1H), 2.73-2.68 (m, 1H), 2.64-2.58 (m, 1H), 2.46-2.36 (m, 3H), 2.30 (dd, J=14.2, 8.9 Hz, 1H), 1.32 (s, 9H), 1.18 (d, J=6.6 Hz, 3H).

Example 33—Preparation of (R)—N$^1$-(tert-butyl)-3-(4-methylphenylsulfonamido)-N$^5$—((S)-4-((naphthalen-1-ylmethyl)amino)-4-oxobutan-2-yl)pentanediamide (PKS2291)

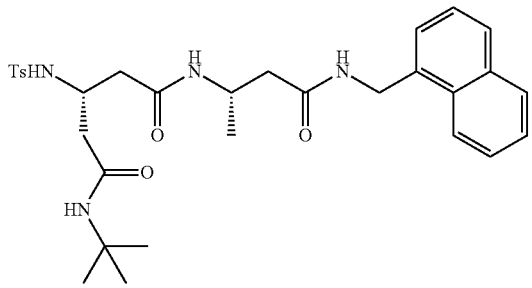

The title compound was prepared by following the general procedure for N-sulfonamide formation of PKS2288 (6.5 mg, 0.012 mmol) with tosyl chloride (4.6 mg, 0.024 mmol). The product was isolated as a white solid (5.2 mg, 74%) after HPLC purification. $^1$H NMR (500 MHz, DMSO-$d_6$) δ 8.40 (t, J=5.6 Hz, 1H), 8.06-8.04 (m, 1H), 7.96-7.94 (m, 1H), 7.85 (d, J=7.8 Hz, 1H), 7.74 (d, J=8.1 Hz, 1H), 7.67-7.66 (m, 2H), 7.55-7.52 (m, 2H), 7.47-7.42 (m, 3H), 7.37-7.33 (m, 3H), 4.74 (dd, J=15.2, 5.6 Hz, 1H), 4.70 (dd, J=15.2, 5.6 Hz, 1H), 4.11-4.05 (m, 1H), 3.80-3.73 (m, 1H), 2.34 (s, 3H), 2.31 (dd, J=13.9, 5.5 Hz, 1H), 2.18-2.08 (m, 5H), 1.18 (s, 9H), 0.98 (d, J=6.6 Hz, 3H). $^{13}$C NMR (126 MHz, DMSO) δ $^{13}$C NMR (126 MHz, DMSO) δ 169.78, 168.94, 168.36, 142.43, 138.65, 134.60, 133.28, 130.86, 129.47, 128.48, 127.56, 126.49, 126.17, 125.80, 125.56, 125.36, 123.52, 50.02, 48.52, 42.19, 41.93, 40.54, 40.13, 40.09, 28.42, 20.93, 19.98.

Example 34—Preparation of (R)—N'-(tert-butyl)-N$^5$—((S)-4-((naphthalen-1-ylmethyl)amino)-4-oxobutan-2-yl)-3-(3-phenylpropanamido)pentanediamide (PKS2292)

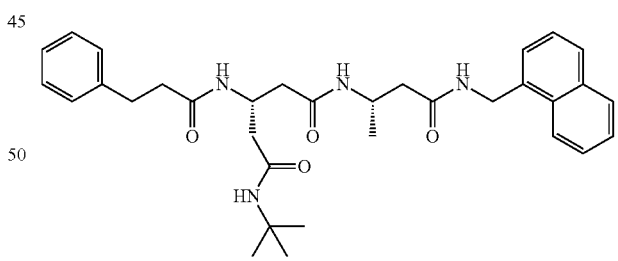

The title compound was synthesized by following the general protocol for HATU mediated coupling of 3-phenylpropanoic acid (2.0 mg, 0.012) and PKS2288 (6.5 mg, 0.012 mmol). The reaction mixture was purified by HPLC to give product (6.0 mg, 90%) as a white solid. $^1$H NMR (500 MHz, DMSO-$d_6$) δ 8.40 (t, J=5.6 Hz, 1H), 8.06-8.04 (m, 1H), 7.95-7.93 (m, 1H), 7.85 (d, J=7.8 Hz, 1H), 7.73 (d, J=8.1 Hz, 1H), 7.64 (d, J=8.3 Hz, 1H), 7.56-7.51 (m, 2H), 7.48-7.42 (m, 2H), 7.33 (s, 1H), 7.26-7.23 (m, 2H), 7.18-7.14 (m, 3H), 4.76-4.68 (m, 2H), 4.31-4.24 (m, 1H), 4.19-4.10 (m, 1H), 2.78 (t, J=7.9 Hz, 2H), 2.38-2.30 (m, 2H), 2.23-2.17 (m, 5H), 1.22 (s, 9H), 1.02 (d, J=6.6 Hz, 3H). $^{13}$C NMR (126

MHz, DMSO) δ 170.46, 169.84, 169.42, 168.78, 141.31, 134.61, 133.27, 130.87, 128.47, 128.25, 128.09, 127.56, 126.18, 125.82, 125.79, 125.57, 125.37, 123.51, 49.94, 44.22, 42.16, 42.04, 40.59, 40.13, 40.06, 37.22, 31.19, 28.48, 20.06.

Example 35—Preparation of PKS3024

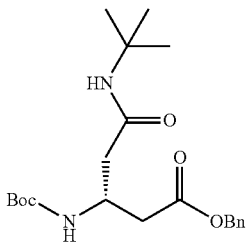 [SMILES: CC(C)(C)NC(=O)C[C@H](CC(=O)OCc1ccccc1)NC(=O)OC(C)(C)C]

The title compound was prepared following the general procedure for EDC mediated coupling of N-Boc-L-β-glutamic acid 5-benzyl ester (168 mg, 0.5 mmol) and tert-butylamine (80 μL, 0.75 mmol). After completion of reaction, water was added to the mixture and extracted twice with ethyl acetate. The organic layer was washed with 1N HCl, water, aq. NaHCO₃, water, and brine. The organic layer was dried over anhydrous sodium sulfate and evaporated and dried to give product (196 mg, quat.). Product was used in next step without any further purification. ¹H NMR (500 MHz, Chloroform-d) δ 7.38-7.30 (m, 5H), 5.72 (bs, 1H), 5.59 (bs, 1H), 5.12 (s, 2H), 4.24-4.15 (m, 1H), 2.79 (dd, J=16.3, 5.2 Hz, 1H), 2.58 (dd, J=15.7, 7.5 Hz, 1H), 2.44-2.34 (m, 2H), 1.41 (s, 9H), 1.30 (s, 9H).

Example 36—Preparation of PKS3028

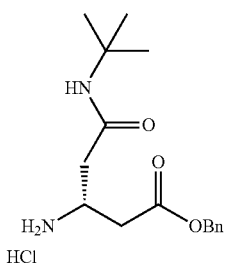 [SMILES: CC(C)(C)NC(=O)C[C@@H](N)CC(=O)OCc1ccccc1 ; Cl]

PKS3024 (196 mg, 0.5 mmol) was dissolved in 5 mL 4N HCl (in dioxane) and mixture was stirred at room temperature for 1 hour. After completion of reaction, dioxane was evaporated and the mixture was diluted with water. The solution was washed with diethyl ether. Aqueous layer was frozen and lyophilized to give product (143 mg, 87%). Complex NMR due to 73:27 rotamers. ¹H NMR (500 MHz, DMSO-d₆) δ 8.35-8.26 (m, 2.1H), 8.17 (s, 0.9H), 7.87 (s, 1H), 7.48-7.26 (m, 4H), 5.12 (s, 2H), 3.75-3.66 (m, 0.73H), 3.66-3.56 (m, 0.27H), 2.83 (dd, J=16.7, 6.6 Hz, 0.73H), 2.75-2.65 (m, 1.27H), 2.60-2.52 (m, 2H), 1.24 (d, J=4.5 Hz, 9H).

Example 37—Preparation of PKS3034

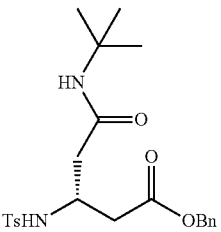

The title compound was prepared by following the general procedure for N-sulfonamide formation of PKS3028 (72.3 mg, 0.22 mmol) with tosyl chloride (63 mg, 0.33 mmol). The product was isolated by dichloromethane extraction and purified by column chromatography to give product as a white solid (50.1 mg, 51%). ¹H NMR (500 MHz, DMSO-d₆) δ 7.73 (d, J=8.2 Hz, 1H), 7.65 (d, J=7.8 Hz, 2H), 7.44 (s, 1H), 7.41-7.29 (m, 7H), 4.98 (d, J=12.6 Hz, 1H), 4.90 (d, J=12.6 Hz, 1H), 3.88 (dtd, J=13.5, 8.0, 5.3 Hz, 1H), 2.46 (dd, J=15.4, 5.4 Hz, 1H), 2.40-2.32 (m, 4H), 2.18 (dd, J=14.6, 8.2 Hz, 1H), 2.12 (dd, J=14.6, 5.4 Hz, 1H), 1.17 (s, 9H).

Example 38—Preparation of PKS3041

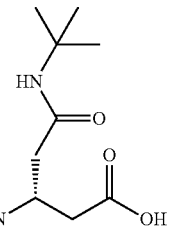

The title compound was synthesized by following the general protocol for O-debenzylation of PKS3034 (14.3 mg, 0.032 mmol). Filtrate was evaporated and dried under vacuum to give product (11.4 mg, quant.). H NMR (500 MHz, DMSO-d₆) δ 7.66 (d, J=7.9 Hz, 2H), 7.42 (s, 1H), 7.35 (d, J=7.9 Hz, 2H), 3.75-3.66 (m, 1H), 2.37 (s, 3H), 2.20-2.11 (m, 4H), 1.18 (s, 9H).

Example 39—Preparation of PKS3044

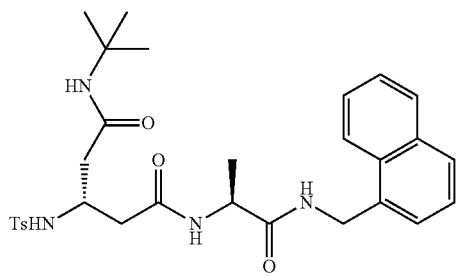

The title compound was prepared following the general procedure for HATU mediated coupling of PKS3041 (11.4 mg, 0.032 mmol) and H-Ala-CH$_2$-naphth TFA salt (13.1 mg, 0.038 mmol). Purification by HPLC gave product (8.0 mg, 44%) as a white solid. $^1$H NMR (500 MHz, DMSO-d$_6$) δ 8.45 (t, J=5.8 Hz, 1H), 8.05-8.00 (m, 2H), 7.96-7.92 (m, 1H), 7.83 (d, J=7.9 Hz, 1H), 7.67 (d, J=8.0 Hz, 2H), 7.55-7.50 (m, 2H), 7.47-7.40 (m, 3H), 7.39 (s, 1H), 7.35 (d, J=8.0 Hz, 2H), 4.74 (dd, J=15.5, 5.7 Hz, 1H), 4.70 (dd, J=15.5, 5.6 Hz, 1H), 4.28-4.18 (m, 1H), 3.86-3.76 (m, 1H), 2.37 (s, 3H), 2.22 (d, J=6.8 Hz, 2H), 2.15-2.05 (m, 2H), 1.22-1.15 (m, 12H). $^{13}$C NMR (126 MHz, DMSO) δ 172.35, 169.18, 168.95, 142.42, 138.82, 134.39, 133.23, 130.76, 129.48, 128.47, 127.44, 126.44, 126.13, 125.76, 125.38, 125.01, 123.36, 50.08, 48.60, 48.35, 40.75, 40.15, 40.10, 28.40, 20.96, 18.09.

Example 40—Preparation of PKS3035

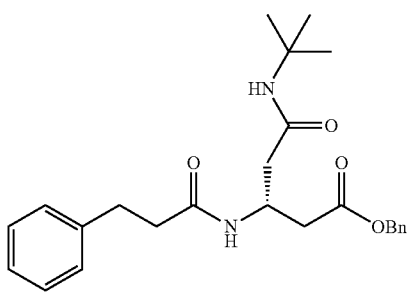 [SMILES: CC(C)(C)NC(=O)C[C@H](CC(=O)OCc1ccccc1)NC(=O)CCc1ccccc1]

Title compound was synthesized by following the general protocol for HATU mediated coupling of 3-phenylpropanoic acid (40 mg, 0.264 mmol) with PKS3028 (72.3 mg, 0.22 mmol). After completion of reaction, water was added to reaction mixture to give white precipitate. Precipitate was filtered, washed with water, and dried in air to give product (50 mg, 45%) as a white solid. $^1$H NMR (500 MHz, DMSO-d$_6$) δ 7.82 (d, J=8.1 Hz, 1H), 7.40 (s, 1H), 7.38-7.28 (m, 5H), 7.28-7.22 (m, 2H), 7.20-7.13 (m, 3H), 5.05 (s, 2H), 4.43-4.30 (m, 1H), 2.82-2.68 (m, 2H), 2.55 (dd, J=15.3, 5.6 Hz, 1H), 2.41-2.08 (m, 5H), 1.22 (s, 9H).

Example 41—Preparation of PKS3038

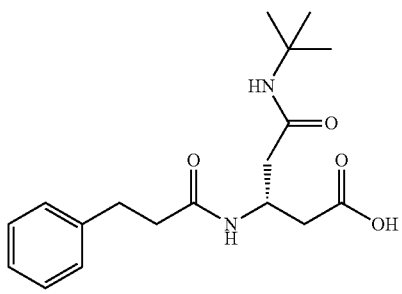 [SMILES: CC(C)(C)NC(=O)C[C@H](CC(=O)O)NC(=O)CCc1ccccc1]

Title compound was prepared following the general protocol for O-debenzylation of PKS3035 (45 mg, 0.106 mmol). The product was isolated as a white solid (35 mg, quant.). $^1$H NMR (500 MHz, DMSO-d$_6$) δ 7.87 (d, J=8.0 Hz, 1H), 7.44 (s, 1H), 7.29-7.22 (m, 2H), 7.21-7.12 (m, 3H), 4.30-4.20 (m, 1H), 2.77 (t, J=7.9 Hz, 2H), 2.37-2.13 (m, 6H), 1.22 (s, 9H).

Example 42—Preparation of PKS3039

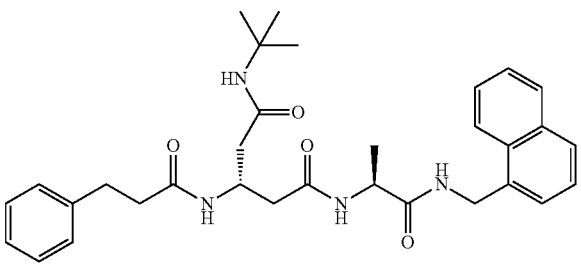 [SMILES: C[C@H](NC(=O)C[C@@H](CC(=O)NC(C)(C)C)NC(=O)CCc1ccccc1)C(=O)NCc1cccc2ccccc12]

The title compound was prepared following the general procedure for HATU mediated coupling of PKS3038 (35.0 mg, 0.032 mmol) and H-Ala-CH$_2$-naphth TFA salt (40.0 mg, 0.116 mmol). Purification by HPLC gave product (17.6 mg, 31%) as a white solid. $^1$H NMR (500 MHz, DMSO-d$_6$) δ 8.45 (t, J=5.8 Hz, 1H), 8.08-8.01 (m, 2H), 7.97-7.90 (m, 1H), 7.83 (dd, J=7.2, 2.4 Hz, 1H), 7.69 (d, J=8.4 Hz, 1H), 7.57-7.49 (m, 2H), 7.49-7.41 (m, 2H), 7.35 (s, 1H), 7.27-7.20 (m, 2H), 7.19-7.11 (m, 3H), 4.79-4.69 (m, 2H), 4.38-4.27 (m, 2H), 2.75 (t, J=8.0 Hz, 2H), 2.35-2.27 (m, 4H), 2.20 (d, J=6.8 Hz, 2H), 1.24-1.19 (m, 12H). $^{13}$C NMR (126 MHz, DMSO) δ 172.44, 170.56, 169.71, 169.40, 141.29, 134.44, 133.23, 130.77, 128.47, 128.26, 128.08, 127.43, 126.14, 125.83, 125.76, 125.38, 124.99, 123.36, 49.99, 48.36, 44.32, 40.82, 40.19, 40.01, 37.29, 31.15, 28.46, 18.22.

Example 43—Preparation of PKS3006

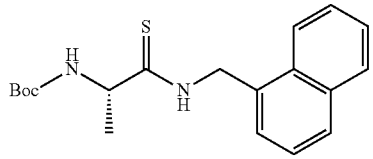 [SMILES: C[C@H](NC(=O)OC(C)(C)C)C(=S)NCc1cccc2ccccc12]

Lawesson reagent (61 mg, 0.15 mmol) was suspended in 1 mL THF and a solution of Boc-Ala-CH$_2$-naphth (98.5 mg, 0.3 mmol) in 2 mL THF was added at room temperature. The reaction mixture was stirred overnight. Reaction was not complete. Additional 30 mg of Lawesson reaction was added and the mixture was stirred additional 18 hours. THF was evaporated and crude was purified by column chromatography to give product (100 mg, 97%). Complex NMR due to rotamers. H NMR (500 MHz, Chloroform-d) δ 8.31 (s, 1H), 7.96-7.78 (m, 3H), 7.58-7.39 (m, 4H), 5.37-5.26 (m, 1H), 5.26-5.10 (m, 2H), 4.56-4.36 (m, 1H), 1.48-1.41 (m, 3H), 1.33-1.21 (m, 9H).

Example 44—Preparation of PKS3019

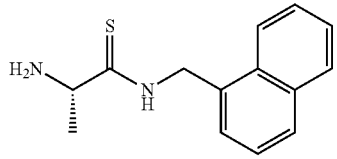 [SMILES: C[C@H](N)C(=S)NCc1cccc2ccccc12]

To a stirred solution of PKS3006 (40 mg, 0.116 mmol) in 2 mL ethyl acetate, SnCl$_4$ (IM in heptane, 0.23 mL, 0.230 mmol) was added at room temperature. Reaction mixture was stirred at room temperature overnight. Solvent was evaporated and crude was triturated with diethyl ether. The solid was filtered and dried to give product as a white solid. The solid was dissolved in DMF and used in next step. $^1$H NMR (500 MHz, DMSO-d$_6$) δ 8.01-7.91 (m, 3H), 7.63-7.46 (m, 5H), 5.25 (d, J=15.2 Hz, 1H), 5.16 (d, J=15.2 Hz, 1H), 4.28-4.17 (m, 1H), 1.40 (d, J=6.6 Hz, 3H).

Example 45—Preparation of PKS3020

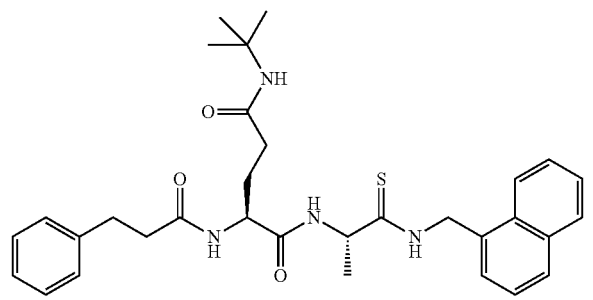 [SMILES: C[C@H](NC(=O)[C@H](CCC(=O)NC(C)(C)C)NC(=O)CCc1ccccc1)C(=S)NCc1cccc2ccccc12]

The title compound was synthesized by following the general protocol for HATU mediated coupling of PhCH$_2$CH$_2$C(O)-Glu(CONHtBu)-OH (18.4 mg, 0.055) and PKS3019 (6.5 mg, 0.05 mmol). The reaction mixture was purified by HPLC to give product (17.3 mg, 62%) as a white solid. $^1$H NMR (500 MHz, DMSO-d$_6$) δ 10.50 (t, J=5.2 Hz, 1H), 8.12 (d, J=7.5 Hz, 1H), 8.09 (d, J=7.7 Hz, 1H), 8.00-7.93 (m, 2H), 7.89 (dd, J=6.5, 3.0 Hz, 1H), 7.61-7.51 (m, 2H), 7.51-7.44 (m, 2H), 7.31-7.21 (m, 3H), 7.21-7.13 (m, 3H), 5.23-5.18 (m, 2H), 4.78-4.68 (m, 1H), 4.25-4.17 (m, 1H), 2.80 (t, J=8.0 Hz, 2H), 2.49-2.38 (m, 2H), 2.05 (t, J=8.0 Hz, 2H), 1.96-1.85 (m, 1H), 1.73-1.62 (m, 1H), 1.32 (d, J=6.8 Hz, 3H), 1.23 (s, 9H). $^{13}$C NMR (126 MHz, DMSO) δ 204.98, 171.62, 171.16, 170.69, 141.29, 133.29, 132.10, 131.01, 128.55, 128.26, 128.13, 127.98, 126.42, 125.99, 125.93, 125.83, 125.40, 123.39, 53.87, 52.35, 49.85, 46.77, 36.81, 32.68, 31.06, 28.53, 27.77, 21.40.

Example 46—Preparation of PKS3021

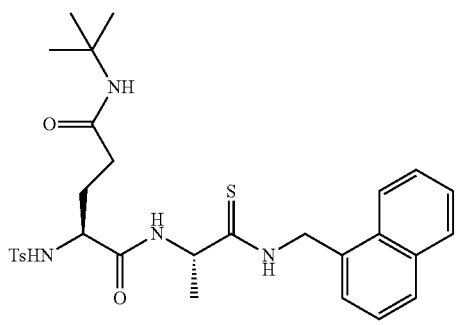

The title compound was synthesized by following the general protocol for HATU mediated coupling of Ts-Glu(CONHtBu)-OH (19.6 mg, 0.055) and PKS3019 (6.5 mg, 0.05 mmol). The reaction mixture was purified by HPLC to give product (15.4 mg, 53%) as a white solid. $^1$H NMR (500 MHz, DMSO-d$_6$) δ 10.44 (t, J=5.2 Hz, 1H), 8.18 (d, J=7.4 Hz, 1H), 7.99-7.94 (m, 1H), 7.94-7.90 (m, 1H), 7.90-7.83 (m, 2H), 7.63 (d, J=8.3 Hz, 2H), 7.58-7.50 (m, 2H), 7.50-7.40 (m, 2H), 7.34-7.29 (m, 3H), 5.20-5.14 (m, 2H), 4.51-4.42 (m, 1H), 3.76-3.67 (m, 1H), 2.35 (s, 3H), 2.10-1.95 (m, 2H), 1.80-1.70 (m, 1H), 1.64-1.53 (m, 1H), 1.21 (s, 9H), 1.17 (d, J=6.7 Hz, 3H). $^{13}$C NMR (126 MHz, DMSO) δ 204.82, 171.07, 169.63, 142.42, 137.96, 133.27, 132.07, 130.98, 129.24, 128.53, 127.95, 126.67, 126.40, 125.91, 125.37, 123.37, 55.72, 53.85, 49.86, 46.67, 32.33, 28.77, 28.48, 20.99, 20.96.

Example 47—Preparation of PKS3049

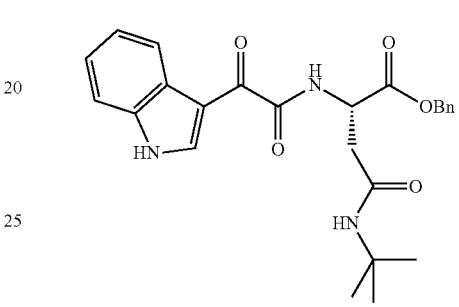

The title compound was synthesized following the general protocol for HATU mediated coupling of 3-indoleglyoxylic acid (189 mg, 1.0 mmol) and H-Asp(CONHtBu)-OH TFA salt (432 mg, 1.1 mmol). The compound was isolated by ethyl acetate extraction and purified by column chromatography to give product (270 mg, 60%) as an off-white solid. $^1$H NMR (500 MHz, Chloroform-d) δ 10.14 (s, 1H), 9.13 (d, J=3.3 Hz, 1H), 8.42-8.34 (m, 2H), 7.47 (dd, J=6.6, 2.3 Hz, 1H), 7.34-7.23 (m, 7H), 5.54 (s, 1H), 5.23 (d, J=12.4 Hz, 1H), 5.19-5.12 (m, 1H), 5.11-5.03 (m, 1H), 2.80 (dd, J=15.2, 5.8 Hz, 1H), 2.74 (dd, J=15.2, 5.3 Hz, 1H), 1.29 (s, 9H). $^{13}$C NMR (126 MHz, CDCl$_3$) δ 179.61, 170.76, 168.78, 162.60, 139.33, 136.24, 135.30, 128.72, 128.56, 128.41, 126.86, 124.09, 123.31, 122.44, 113.14, 112.12, 67.73, 51.99, 49.58, 39.23, 28.78.

Example 48—Preparation of PKS3052

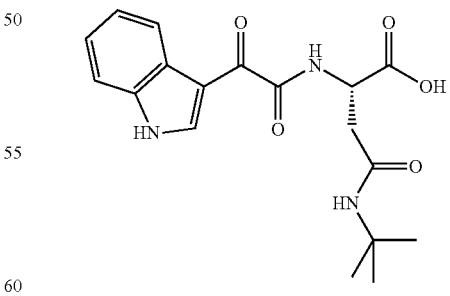

The title compound was synthesized following the general protocol for O-debenzylation of PKS3049 (265 mg, 0.59 mmol). Isolated crude was purified by HPLC to give product (112 mg, 53%) as an off-white solid. $^1$H NMR (500 MHz, DMSO-d$_6$) δ 12.81 (s, 1H), 12.27 (d, J=3.3 Hz, 1H), 8.82-8.75 (m, 2H), 8.26-8.20 (m, 1H), 7.57 (s, 1H), 7.56-

7.52 (m, 1H), 7.32-7.23 (m, 2H), 4.69-4.60 (m, 1H), 2.67 (dd, J=15.1, 7.2 Hz, 1H), 2.59 (dd, J=15.1, 5.0 Hz, 1H), 1.22 (s, 9H). $^{13}$C NMR (126 MHz, DMSO) δ 181.25, 172.26, 168.78, 162.78, 138.64, 136.25, 126.14, 123.53, 122.66, 121.28, 112.60, 112.11, 50.16, 48.97, 37.16, 28.44.

Example 49—Preparation of PKS3054

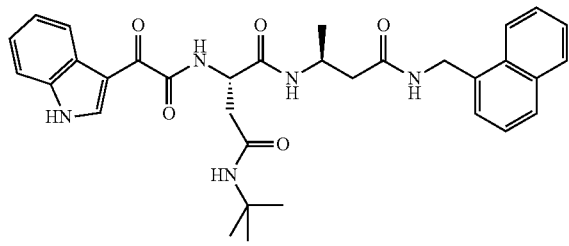 [SMILES: C[C@@H](CC(=O)NCc1cccc2ccccc12)NC(=O)[C@H](CC(=O)NC(C)(C)C)NC(=O)C(=O)c1c[nH]c2ccccc12]

The title compound was synthesized by following the general protocol for HATU mediated coupling of 3-Ind-Glyoxylolyl-Asp-(CONHtBu)-OH (7.2 mg, 0.02) and H-β-homo-Ala-CH$_2$-naphth TFA salt (7.8 mg, 0.022 mmol). The reaction mixture was purified by HPLC to give product (4.0 mg, 34%) as a white solid. H NMR (500 MHz, DMSO-d$_6$) δ 12.24 (d, J=3.6 Hz, 1H), 8.81 (d, J=3.1 Hz, 1H), 8.70 (d, J=8.4 Hz, 1H), 8.41 (t, J=5.7 Hz, 1H), 8.28-8.21 (m, 1H), 8.02 (dd, J=6.3, 3.4 Hz, 1H), 7.98 (d, J=8.0 Hz, 1H), 7.93 (dd, J=6.2, 3.4 Hz, 1H), 7.83 (d, J=8.0 Hz, 1H), 7.58-7.48 (m, 4H), 7.48-7.37 (m, 2H), 7.31-7.23 (m, 2H), 4.74 (dd, J=15.2, 5.7 Hz, 1H), 4.67 (dd, J=15.2, 5.5 Hz, 1H), 4.62-4.54 (m, 1H), 4.20-4.09 (m, 1H), 2.59 (dd, J=14.5, 8.4 Hz, 1H), 2.43 (dd, J=14.5, 4.7 Hz, 1H), 2.36 (dd, J=14.0, 5.8 Hz, 1H), 2.26 (dd, J=14.0, 7.7 Hz, 1H), 1.20 (s, 9H), 1.06 (d, J=6.6 Hz, 3H).

Example 50—Preparation of PKS3056

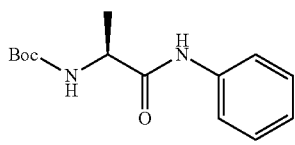 [SMILES: C[C@H](NC(=O)OC(C)(C)C)C(=O)Nc1ccccc1]

Boc-Ala-OSu (600 mg, 2.10 mmol) was dissolved in 10 mL dichloromethane and the solution was cooled to 0° C. Aniline and triethylamine were added to the solution at 0° C. Reaction mixture was allowed to warm to room temperature slowly (over 1 hour) and stirred overnight. Water was added to the reaction mixture and extracted twice with ethyl acetate. Combined organic layer was washed with 1N HCl and brine, dried over anhydrous sodium sulfate and evaporated to give product 468 mg (84%). Product was used in next step without further purification. $^1$H NMR (500 MHz, Chloroform-d) δ 8.42 (s, 1H), 7.55-7.48 (m, 2H), 7.31 (td, J=7.5, 4.9 Hz, 2H), 7.09 (t, J=7.4 Hz, 1H), 5.14-4.99 (m, 1H), 4.39-4.24 (m, 1H), 1.46 (s, 9H), 1.43 (d, J=7.0 Hz, 3H).

Example 51—Preparation of PKS3057

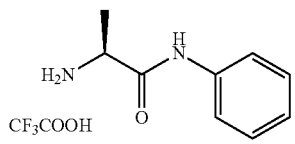

The title compound was synthesized by following the general protocol for Boc-deprotection of Boc-Ala-NHPh (468 mg, 1.77 mmol). The crude obtained was suspended in diethyl ether. An off-white solid appeared. Diethyl ether was decanted and solid was dried to give product (411 mg, 84%). Product was used in next step without further purification. $^1$H NMR (500 MHz, DMSO-d$_6$) δ 10.49 (s, 1H), 8.25 (s, 3H), 7.63-7.57 (m, 2H), 7.39-7.32 (m, 2H), 7.15-7.08 (m, 1H), 4.02 (d, J=7.2 Hz, 1H), 1.46 (d, J=7.0 Hz, 3H).

Example 52—Preparation of PKS3061

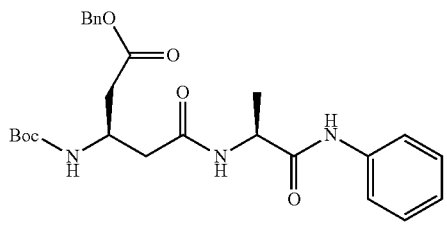 [SMILES: C[C@H](NC(=O)C[C@H](CC(=O)OCc1ccccc1)NC(=O)OC(C)(C)C)C(=O)Nc1ccccc1]

The title compound was synthesized by following the general protocol for HATU mediated coupling of N-Boc-L-β-glutamic acid 5-benzyl ester (84 mg, 0.25 mmol) and PKS3057 (83 mg, 0.3 mmol). After completion of reaction, water was added to reaction mixture to give white precipitate. Precipitate was filtered, washed with water, and dried in air to give product (115 mg, 95%) as a white solid. H NMR (500 MHz, DMSO-d$_6$) δ 9.94 (s, 1H), 8.19 (t, J=6.2 Hz, 1H), 7.59 (d, J=8.0 Hz, 2H), 7.44-7.21 (m, 7H), 7.04 (t, J=7.4 Hz, 1H), 6.89-6.75 (m, 1H), 5.05 (s, 2H), 4.46-4.32 (m, 1H), 4.23-4.06 (m, 1H), 2.62-2.44 (m, 2H), 2.43-2.27 (m, 2H), 1.35 (s, 9H), 1.27 (d, J=7.1 Hz, 3H).

Example 53—Preparation of PKS3063

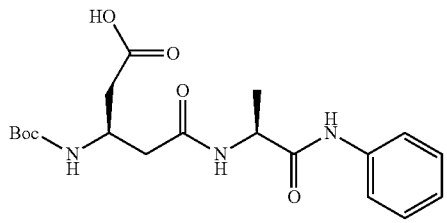 [SMILES: C[C@H](NC(=O)C[C@H](CC(=O)O)NC(=O)OC(C)(C)C)C(=O)Nc1ccccc1]

The title compound was synthesized by following the O-debenzylation protocol of PKS3061 (115 mg, 0.24 mmol)

to give product (94.4 mg, quant.) as a white solid. Complex NMR due to 0.28:0.72 ratio of rotamers. $^1$H NMR (500 MHz, DMSO-d$_6$) δ 12.15 (s, 1H), 10.01 (s, 0.28H), 9.95 (s, 0.82H), 8.18 (d, J=7.1 Hz, 1H), 7.62-7.58 (m, 2H), 7.31-7.26 (m, 2H), 7.04 (t, J=7.4 Hz, 1H), 6.75 (d, J=8.5 Hz, 0.28H), 6.71 (d, J=8.4 Hz, 0.82H), 4.49-4.31 (m, 1H), 4.16-3.97 (m, 1H), 2.42-2.26 (m, 4H), 1.39-1.32 (m, 9H), 1.28 (d, J=7.1 Hz, 3H).

Example 54—Preparation of PKS3065

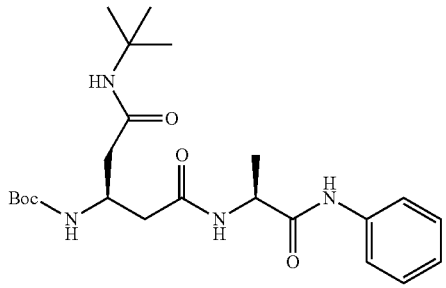 [SMILES: C[C@H](NC(=O)C[C@H](CC(=O)NC(C)(C)C)NC(=O)OC(C)(C)C)C(=O)Nc1ccccc1]

The title compound was synthesized following the general protocol for EDC mediated coupling of PKS3063 (94.4 mg, 0.24 mmol) and tert-butylamine (38 mL, 0.36 mmol). After completion of reaction water was added to give a white precipitate. Precipitate was filtered, washed with water, and dried in air to give product (85 mg, 79%) as an off-white solid. H NMR (500 MHz, DMSO-d$_6$) δ 9.96 (s, 0.28H), 9.93 (s, 0.82H), 8.11 (d, J=7.3 Hz, 1H), 7.60 (d, J=8.0 Hz, 2H), 7.35-7.26 (m, 3H), 7.04 (t, J=7.4 Hz, 1H), 6.59-6.51 (m, 1H), 4.46-4.36 (m, 1H), 4.09-4.00 (m, 1H), 2.37-2.24 (m, 2H), 2.24-2.13 (m, 2H), 1.35 and 1.34 (s, 9H), 1.31-1.25 (m, 3H), 1.23 (s, 9H).

Example 55—Preparation of PKS3069

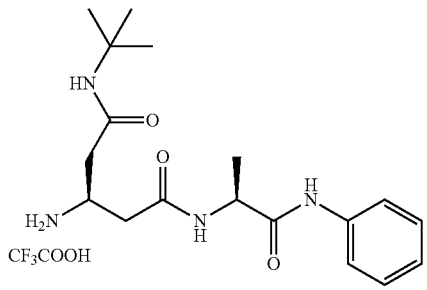 [SMILES: "CF3COOH" ; C[C@H](NC(=O)C[C@@H](N)CC(=O)NC(C)(C)C)C(=O)Nc1ccccc1]

The title compound was synthesized following the general protocol for Boc-deprotection to give 87 mg product (quant.). H NMR (500 MHz, DMSO-d$_6$) δ 10.05 (s, 1H), 8.57-8.51 (m, 1H), 7.85 (d, J=6.3 Hz, 3H), 7.80 (s, 0.76H), 7.79 (s, 0.24H), 7.59 (d, J=8.0 Hz, 2H), 7.34-7.27 (m, 2H), 7.05 (t, J=7.4 Hz, 1H), 4.49-4.40 (m, 1H), 3.68-3.60 (m, 1H), 2.54-2.46 (m, 2H), 2.45-2.32 (m, 2H), 1.34-1.29 (m, 3H), 1.26 (s, 9H).

Example 56—Preparation of PKS3076

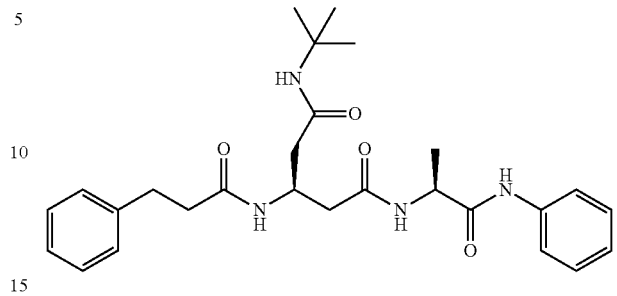

The title compound was synthesized following the general protocol for HATU mediated coupling of 3-phenylpropanoic acid (8.3 mg, 0.055 mmol) and PKS3076 (23.1 mg, 0.05 mmol). Purification by HPLC gave the product (20.0 mg, 83%) as a white solid. Complex NMR due to 0.28:0.72 ratio of rotamers. $^1$H NMR (500 MHz, DMSO-d$_6$) δ 9.97 (s, 0.28H), 9.94 (s, 0.72H), 8.15-8.09 (m, 1H), 7.66 (t, J=7.8 Hz, 1H), 7.62-7.57 (m, 2H), 7.36-7.29 (m, 1H), 7.29-7.21 (m, 4H), 7.21-7.12 (m, 3H), 7.07-7.00 (m, 1H), 4.46-4.38 (m, 1H), 4.34-4.26 (m, 1H), 2.82-2.72 (m, 2H), 2.40-2.26 (m, 4H), 2.24-2.18 (m, 2H), 1.30-1.25 (m, 3H), 1.22 (s, 9H). $^{13}$C NMR (126 MHz, DMSO) δ 171.33, 170.49, 169.79, 169.39, 141.32, 138.94, 128.63, 128.23, 128.08, 125.78, 123.26, 119.24, 49.97, 48.97, 44.19, 40.78, 39.70, 37.21, 31.14, 28.47, 18.17.

Example 57—Preparation of PKS3077

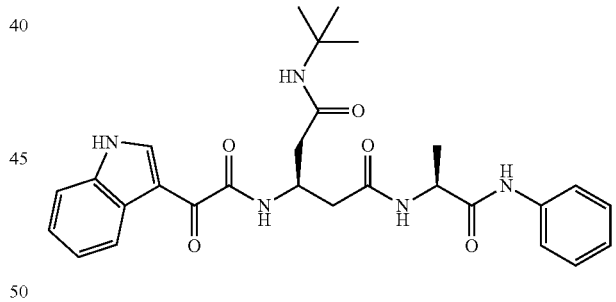

The title compound was synthesized following the general protocol for HATU mediated coupling of 3-indoleglyoxylic acid (10.4 mg, 0.055 mmol) and PKS3076 (23.1 mg, 0.05 mmol). Purification by HPLC gave the product (15.0 mg, 58%) as an off-white solid. Complex NMR due to 0.27:0.73 ratio of rotamers. H NMR (500 MHz, DMSO-d$_6$) δ 12.21 (s, 1H), 9.98 (s, 0.27H), 9.93 (s, 0.73H), 8.81-8.77 (m, 1H), 8.64 (d, J=8.9 Hz, 1H), 8.28-8.19 (m, 2H), 7.63-7.45 (m, 4H), 7.32-7.19 (m, 4H), 7.07-6.97 (m, 1H), 4.55-4.46 (m, 1H), 4.45-4.37 (m, 1H), 2.54-2.49 (m, 1H), 2.47-2.34 (m, 2H), 2.32-2.25 (m, 1H), 1.29 (d, J=7.1 Hz, 2.3H), 1.24-1.22 (m, 9.7H). $^{13}$C NMR (126 MHz, DMSO) δ 181.66, 171.23, 169.77, 169.36, 162.07, 138.85, 138.56, 136.18, 128.58, 126.25, 123.38, 123.23, 122.52, 121.26, 119.28, 112.51, 112.10, 50.05, 49.02, 44.19, 40.17, 39.19, 28.43, 18.10.

Example 58—Preparation of PKS3071

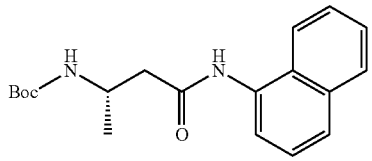 [SMILES: C[C@@H](CC(=O)Nc1cccc2ccccc12)NC(=O)OC(C)(C)C]

The title compound was synthesized by following the general protocol for HATU mediated coupling of Boc-L-β-homoalanine (50.8 mg, 0.25 mmol) and 1-naphthylamine hydrochloride (50 mg, 0.275 mmol). After completion of reaction water was added to give a white precipitate. Precipitate was filtered, washed with water, and dried in air to give product (62 mg, 76%) as a white solid. $^1$H NMR (500 MHz, DMSO-$d_6$) δ 9.87 (s, 1H), 8.09-8.02 (m, 1H), 7.93 (dd, J=6.2, 3.3 Hz, 1H), 7.76 (d, J=8.2 Hz, 1H), 7.65 (d, J=7.3 Hz, 1H), 7.57-7.51 (m, 2H), 7.51-7.44 (m, 1H), 6.86 (d, 0.1=8.3 Hz, 1H), 4.06-3.91 (m, 1H), 2.63 (dd, J1=13.9, 6.7 Hz, 1H), 2.57-2.51 (m, 1H), 1.38 (s, 9H), 1.16 (d, J=6.5 Hz, 3H).

Example 59—Preparation of PKS3073

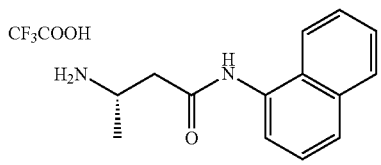 [SMILES: "CF3COOH" ; C[C@H](N)CC(=O)Nc1cccc2ccccc12]

The title compound was prepared by following the general protocol for Boc-deprotection of PKS3071 (57 mg, 0.174 mmol). The crude was triturated with diethyl ether and filtered. The solid was dried to give product (59 mg, quant.) as a brown solid. $^1$H NMR (500 MHz, DMSO-$d_6$) δ 10.22 (s, 1H), 8.10-8.05 (m, 1H), 8.03-7.92 (m, 4H), 7.79 (d, J=8.2 Hz, 1H), 7.69 (d, J=7.4 Hz, 1H), 7.60-7.47 (m, 3H), 3.74-3.58 (m, 1H), 2.85 (d, J=6.6 Hz, 2H), 1.31 (d, J=6.6 Hz, 3H).

Example 60—Preparation of PKS21012

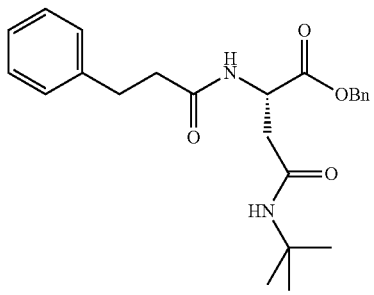 [SMILES: CC(C)(C)NC(=O)C[C@H](NC(=O)CCc1ccccc1)C(=O)OCc1ccccc1]

The title compound was synthesized by following the general procedure for the HATU mediated coupling of 3-phenylpropanoic acid (1.68 g, 11.17 mmol) with PKS3047 (3.98 g, 10.15 mmol). After completion of reaction, water was added. A white precipitate was formed. The precipitate was filtered and washed with water. Precipitate was dried in air to give product (3.92 g, 94%) as a white solid. $^1$H NMR (500 MHz, Chloroform-d) δ 7.39-7.29 (m, 5H), 7.29-7.23 (m, 2H), 7.21-7.14 (m, 3H), 6.88 (d, J=8.0 Hz, 1H), 5.32 (s, 1H), 5.20 (d, J=12.3 Hz, 1H), 5.14 (d, J=12.3 Hz, 1H), 4.84-4.77 (m, 1H), 2.95 (t, J=7.9 Hz, 2H), 2.81 (dd, J=15.7, 4.4 Hz, 1H), 2.61-2.47 (m, 3H), 1.28 (s, 9H).

Example 61—Preparation of PKS21013

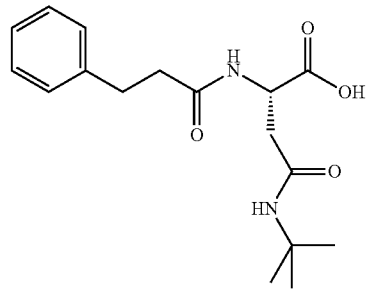 [SMILES: CC(C)(C)NC(=O)C[C@H](NC(=O)CCc1ccccc1)C(=O)O]

The title compound was synthesized by following the procedure for O-debenzylation of PKS21012 (1.44 g, 3.50 mmol). Product (1.11 g, 99%) was isolated as a white solid. $^1$H NMR (500 MHz, DMSO-$d_6$) δ 12.54 (s, 1H), 8.04 (d, J=8.0 Hz, 1H), 7.45 (s, 1H), 7.29-7.23 (m, 2H), 7.23-7.13 (m, 3H), 4.52-4.44 (m, 1H), 2.83-2.76 (m, 2H), 2.49-2.44 (m, 1H), 2.44-2.34 (m, 3H), 1.22 (s, 9H).

Example 62—Preparation of PKS3081

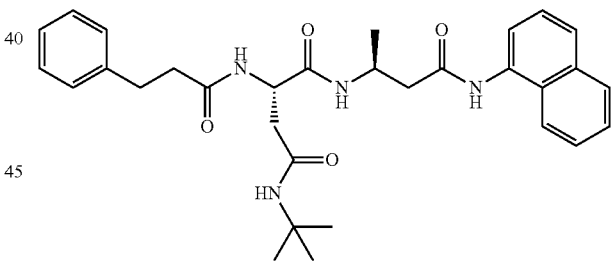

The title compound was synthesized following the general procedure for HATU mediated coupling of PKS21013 (16.0 mg, 0.05 mmol) and PKS3073 (18.8 mg, 0.055 mmol). Purification by HPLC gave the product (21.0 mg, 79%) as a white solid. $^1$H NMR (500 MHz, DMSO-$d_6$) δ 9.95 (s, 1H), 8.05 (d, J=8.0 Hz, 1H), 8.00 (d, J=8.2 Hz, 1H), 7.96-7.89 (m, 2H), 7.76 (d, J=8.2 Hz, 1H), 7.64 (d, J=7.4 Hz, 1H), 7.58-7.50 (m, 2H), 7.48 (t, J=7.8 Hz, 1H), 7.32 (s, 1H), 7.28-7.21 (m, 2H), 7.20-7.12 (m, 3H), 4.60-4.47 (m, 1H), 4.32-4.14 (m, 1H), 2.82-2.75 (m, 2H), 2.65 (dd, J=14.2, 5.9 Hz, 1H), 2.58 (dd, J=14.2, 7.2 Hz, 1H), 2.45-2.35 (m, 3H), 2.31 (dd, J=14.7, 8.6 Hz, 1H), 1.21 (s, 9H), 1.17 (d, J=6.5 Hz, 3H). $^{13}$C NMR (126 MHz, DMSO) δ 171.15, 170.16, 169.82, 168.77, 141.30, 133.68, 133.44, 128.27, 128.12, 128.07, 127.92, 125.97, 125.83, 125.82, 125.50, 125.32, 122.79, 122.06, 50.11, 50.05, 42.54, 42.29, 38.80, 36.90, 31.00, 28.45, 20.19.

Example 63—Preparation of PKS21204

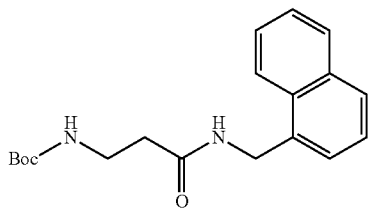 [SMILES: CC(C)(C)OC(=O)NCCC(=O)NCc1cccc2ccccc12]

Boc-β-Ala-OSu (286.28 mg, 1.00 mmol) was dissolved in dichloromethane (5.00 mL) and 1-naphthylmethanamine (157.21 mg, 1.00 mmol) was added. The solution was cooled to 0° C. and triethylamine (101.19 mg, 1.00 mmol) was added. The reaction mixture was allowed to warm to room temperature and stirred at room temperature for 2 hours. After completion of reaction, dichloromethane was evaporated and water was added. A white precipitate appeared. Precipitate was filtered, washed with water and dried in air to give product (320 mg, 97%) as a white solid. Product was used in next step without further purification. $^1$H NMR (500 MHz, Chloroform-d) δ 7.99 (d, J=8.3 Hz, 1H), 7.88 (d, J=8.0 Hz, 1H), 7.85-7.78 (m, 1H), 7.59-7.48 (m, 2H), 7.45-7.40 (m, 2H), 5.90 (bs, 1H), 5.14 (bs, 1H), 4.93-4.85 (m, 2H), 3.48-3.37 (m, 2H), 2.45-2.36 (m, 2H), 1.39 (s, 9H).

Example 64—Preparation of PKS21211

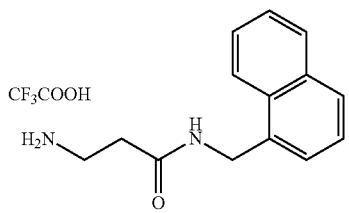 [SMILES: "CF3COOH" ; NCCC(=O)NCc1cccc2ccccc12]

The title compound was synthesized by following the general procedure for Boc-deprotection of PKS21204 (320 mg, 0.974 mmol). After completion of reaction, excess trifluoroacetic acid and dichloromethane were evaporated. Crude was dried under vacuum and triturated with diethyl ether to give a white solid. Solid was filtered and dried in air to give product (320 mg, 96%). Product was used in next step without further purification. $^1$H NMR (500 MHz, DMSO-d$_6$) δ 8.63 (t, J=5.6 Hz, 1H), 8.10-8.02 (m, 1H), 7.96 (dd, J=6.9, 2.2 Hz, 1H), 7.87 (dd, J=7.0, 2.4 Hz, 1H), 7.71 (bs, 3H), 7.59-7.52 (m, 2H), 7.51-7.44 (m, 2H), 4.76 (d, J=5.6 Hz, 2H), 3.10-2.96 (m, 2H), 2.53 (t, J=6.8 Hz, 2H).

Example 65—Preparation of PKS21220

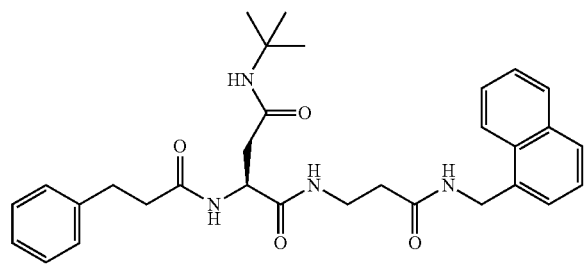 [SMILES: CC(C)(C)NC(=O)C[C@H](NC(=O)CCc1ccccc1)C(=O)NCCC(=O)NCc1cccc2ccccc12]

The title compound was synthesized by following the general procedure for HATU mediated coupling of PKS21013 (16.0 mg, 50 umol) and PKS21211 (19.6 mg, 74%). After completion of reaction (1 h, temperature rose to 10° C.), mixture was purified by preparative LCMS to give product (19.6 mg, 74%) as a white solid. $^1$H NMR (500 MHz, DMSO-d$_6$) δ 8.43 (t, J=5.7 Hz, 11H), 8.04 (d, J=8.1 Hz, 11H), 7.99 (d, J=8.1 Hz, 11H), 7.94 (d, J=7.8 Hz, 1H), 7.84 (d, J=8.0 Hz, 1H), 7.79 (t, J=5.8 Hz, 1H), 7.59-7.50 (m, 2H), 7.50-7.40 (m, 2H), 7.34 (s, 1H), 7.28-7.22 (m, 2H), 7.21-7.13 (m, 3H), 4.73 (d, J=5.6 Hz, 2H), 4.55-4.45 (m, 1H), 3.31-3.21 (m, 2H), 2.80 (t, J=8.0 Hz, 214), 2.45-2.37 (m, 314), 2.32 (t, J=7.5 Hz, 2H), 2.30-2.24 (m, 1H), 1.21 (s, 9H). $^{13}$C NMR (126 MHz, DMSO) δ 171.17, 170.88, 170.25, 168.76, 141.29, 134.52, 133.27, 130.85, 128.49, 128.27, 128.11, 127.52, 126.22, 125.84, 125.77, 125.45, 125.41, 123.43, 50.09, 50.02, 40.15, 38.69, 36.92, 35.52, 35.09, 31.00, 28.45.

Example 66—Measurement of IC50s of Dipeptidomimetics Against Chymotryptic Activities of the Human Constitutive Proteasome and Immunoproteasome Assays were conducted on a SpectraMax Gemini plate-reader from Molecular Devices (Sunnyvale, Calif.). In a black 96-well plate, 100 μL of pre-warmed assay mixture containing 0.4 nM Hu i-20S or 0.2 nM Hu c-20S, 15 μM N-acetyl-Alanine-Asparagine-Tryptophan-7-amino-4-methylcourmarin (Ac-ANW-AMC) (substrate for i-20S) or 25 μM N-succinyl-Leucine-Leucine-Valine-Tyrosine-7-amino-4-methylcourmarin (suc-LLVY-AMC) (substrate for c-20S), 0.02% SDS in buffer (50 mM HEPES, 0.5 mM EDTA, pH7.4) was added to the wells that contained 1 μL inhibitor at 100× indicated concentrations in DMSO. The reaction progress of each well was recorded by monitoring fluorescence at 460 nm (kex=360 nm) for 120 minutes at 37° C. Velocities were derived from the initial linear range of the curves and the IC50s were obtained by plotting the percentage of inhibitor versus inhibitor concentrations (FIG. 1).

Example 67—Proteasome Inhibitory Studies of Various N,C Capped Dipeptidomimetics A variety of dipeptidomimetics were synthesized and tested for their ability to inhibit the proteasomes, as described in Example 1. These compounds inhibited the proteasomes reversibly. The IC50s of these compounds against human immunoproteasome β5i and constitutive proteasome β5c are listed in Table 1. IC50 curves are shown in FIG. 1. These data show that compounds with substituents at amide side chain of the Asparagine (2nd amino acid from C-terminus) and C-terminal caps allowed the resulting dipeptides to selectively inhibit the human immunoproteasome β5i active site over the human constitutive proteasome β5c active site.

TABLE 1
Kinetic parameters and calculated logP of N,C-capped dipeptidomimetics
| ID | Structures | IC50 (μM) | | logP |
|---|---|---|---|---|
| | | Hu i-20S | Hu c-20S | |
| PKS2249 | 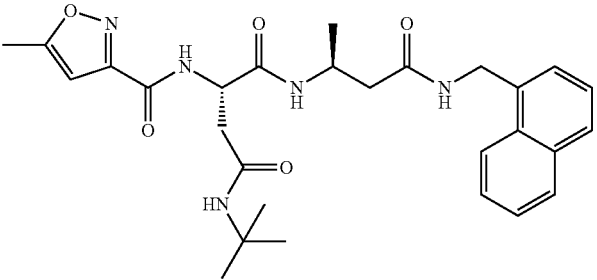 [SMILES: Cc1cc(C(=O)N[C@@H](CC(=O)NC(C)(C)C)C(=O)N[C@@H](C)CC(=O)NCc2cccc3ccccc23)no1] | 0.18 | 16.1 | 0.55 |
| PKS2251 | 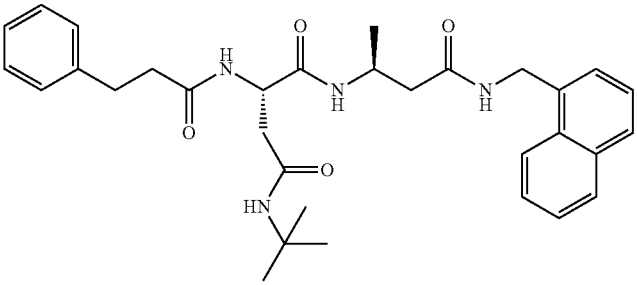 [SMILES: C[C@@H](CC(=O)NCc1cccc2ccccc12)NC(=O)[C@H](CC(=O)NC(C)(C)C)NC(=O)CCc1ccccc1] | 0.045 | 32.2 | 2.75 |
| PKS2252 | 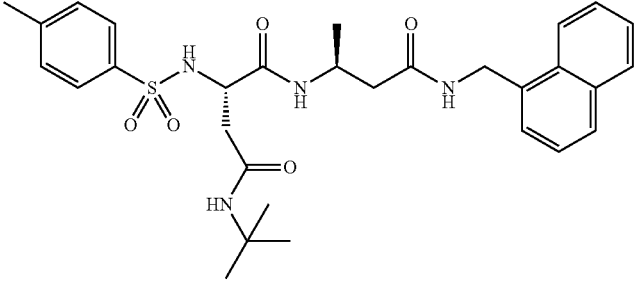 [SMILES: Cc1ccc(S(=O)(=O)N[C@@H](CC(=O)NC(C)(C)C)C(=O)N[C@@H](C)CC(=O)NCc2cccc3ccccc23)cc1] | 0.0064 | 8.81 | 2.72 |
| PKS2253 | 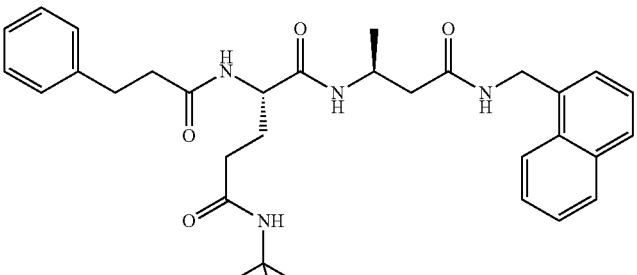 | 0.31 | 17.8 | 3.03 |
| PKS2260 | 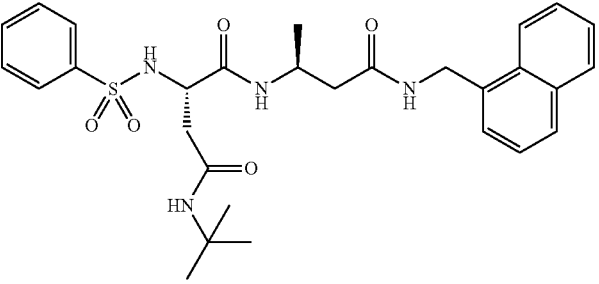 [SMILES: C[C@@H](CC(=O)NCc1cccc2ccccc12)NC(=O)[C@H](CC(=O)NC(C)(C)C)NS(=O)(=O)c1ccccc1] | 0.0112 | 16.55 | 2.23 |

TABLE 1-continued

Kinetic parameters and calculated logP of N,C-capped dipeptidomimetics

| ID | Structures | IC50 (μM) | | logP |
| --- | --- | --- | --- | --- |
| | | Hu i-20S | Hu c-20S | |
| PKS2272 | | 0.152 | >100 | 1.95 |
| PKS2278 | | 2.26 | >100 | 2.75 |
| PKS2279 | | 0.0145 | 34.7 | 3.73 |
| PKS2290 | | 1.60 | 13.9 | 4.19 |

TABLE 1-continued

Kinetic parameters and calculated logP of N,C-capped dipeptidomimetics

| ID | Structures | IC50 (μM) | | logP |
|---|---|---|---|---|
| | | Hu i-20S | Hu c-20S | |
| PKS2291 | 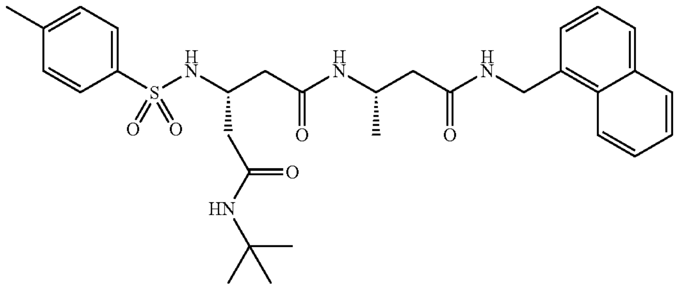 [SMILES: Cc1ccc(S(=O)(=O)N[C@H](CC(=O)N[C@@H](C)CC(=O)NCc2cccc3ccccc23)CC(=O)NC(C)(C)C)cc1] | 8.68 | >100 | 4.19 |
| PKS2292 | 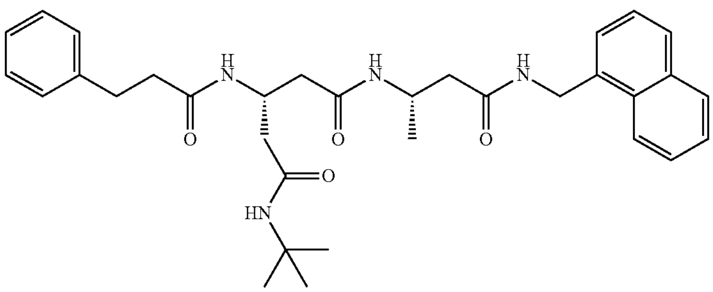 [SMILES: C[C@@H](CC(=O)NCc1cccc2ccccc12)NC(=O)C[C@H](CC(=O)NC(C)(C)C)NC(=O)CCc1ccccc1] | >100 | >100 | 2.87 |
| PKS2295 | 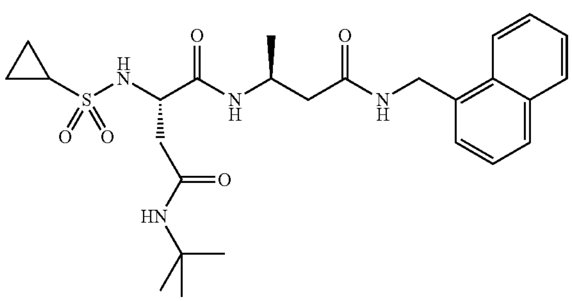 [SMILES: C[C@@H](CC(=O)NCc1cccc2ccccc12)NC(=O)[C@H](CC(=O)NC(C)(C)C)NS(=O)(=O)C1CC1] | 0.141 | ND | 0.69 |
| PKS3020 | 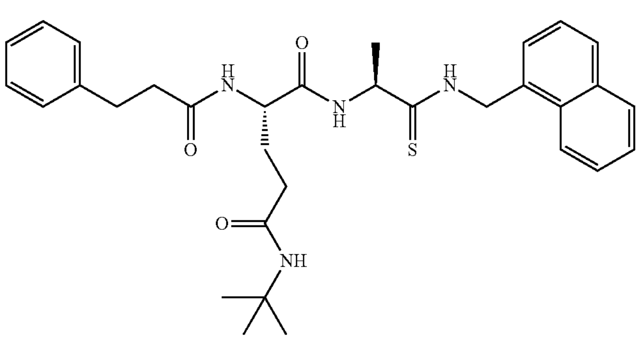 [SMILES: C[C@H](NC(=O)[C@H](CCC(=O)NC(C)(C)C)NC(=O)CCc1ccccc1)C(=S)NCc1cccc2ccccc12] | 0.799 | 7.0 | 3.9 |

TABLE 1-continued
Kinetic parameters and calculated logP of N,C-capped dipeptidomimetics
| ID | Structures | IC50 (μM) | | logP |
|---|---|---|---|---|
| | | Hu i-20S | Hu c-20S | |
| PKS3021 | 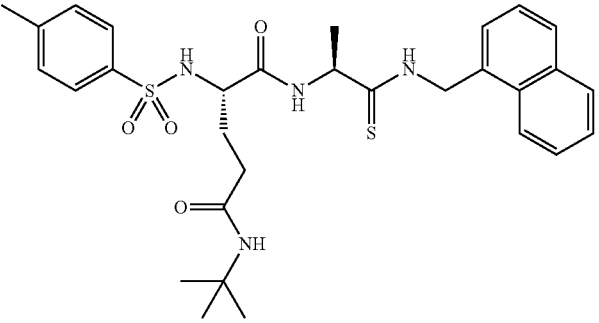 [SMILES: Cc1ccc(S(=O)(=O)N[C@@H](CCC(=O)NC(C)(C)C)C(=O)N[C@@H](C)C(=S)NCc2cccc3ccccc23)cc1] | 0.671 | 13.4 | 3.86 |
| PKS3054 | 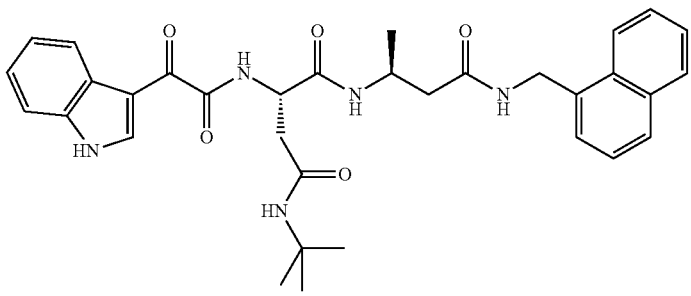 [SMILES: C[C@@H](CC(=O)NCc1cccc2ccccc12)NC(=O)[C@H](CC(=O)NC(C)(C)C)NC(=O)C(=O)c1c[nH]c2ccccc12] | 0.0048 | 0.234 | 1.47 |
| PKS3065 | 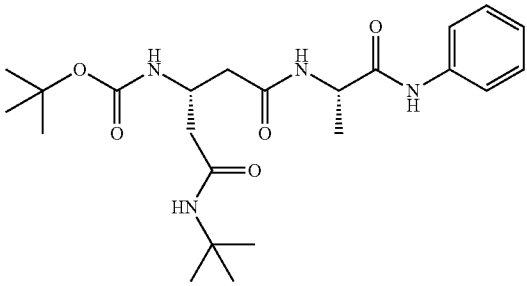 [SMILES: C[C@H](NC(=O)C[C@H](CC(=O)NC(C)(C)C)NC(=O)OC(C)(C)C)C(=O)Nc1ccccc1] | >100 | >100 | 0.89 |
| PKS3081 | 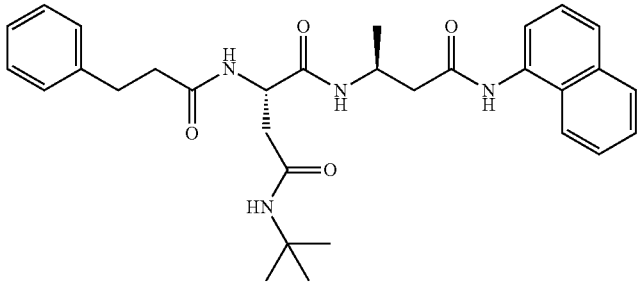 [SMILES: C[C@@H](CC(=O)Nc1cccc2ccccc12)NC(=O)[C@H](CC(=O)NC(C)(C)C)NC(=O)CCc1ccccc1] | 13.7 | >100 | 2.68 |
| PKS21220 | 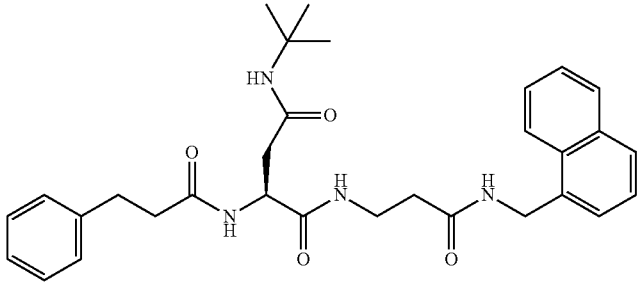 [SMILES: CC(C)(C)NC(=O)C[C@H](NC(=O)CCc1ccccc1)C(=O)NCCC(=O)NCc1cccc2ccccc12] | 0.655 | 51.4 | 2.59 |

Although the invention has been described in detail, for the purpose of illustration, it is understood that such detail is for that purpose and variations can be made therein by those skilled in the art without departing from the spirit and scope of the invention which is defined by the following claims.

What is claimed:

1. A compound of Formula (I):

$$R^4-[N(H)-L]_s-C(Y)-N(H)-M-N(H)-C(Y)-X-R^1 \quad (I)$$

wherein
  L is —(CR$^3$R$^x$)$_p$—;
  M is —(CR$^2$R$^y$)—, —(CH$_2$)—(CR$^2$R$^y$)—, or —(CR$^2$R$^y$)—(CH$_2$)—;
  R$^1$ is unsubstituted monocyclic or bicyclic aryl;
  R$^2$ is C$_{1-6}$ alkyl;
  R$^3$ is H or —(CH$_2$)$_m$C(O)NHR$^5$;
  R$^4$ is selected from the group consisting of —C(O)(CH$_2$)$_n$Ph, —C(O)heteroaryl, —SO$_2$aryl, —SO$_2$C$_{3-6}$cycloalkyl, and —C(O)C(O)heteroaryl, wherein aryl and heteroaryl can be optionally substituted 1 time with C$_{1-6}$ alkyl;
  R$^5$ is C$_{1-6}$ alkyl;
  R$^x$ is H;
  R$^y$ is H;
  X is —(CH$_2$)$_q$—;
  Y is O;
  m is 1 or 2;
  n is 2;
  p is 1 or 2;
  q is 0 or 1; and
  s is 1;
  with a proviso that when M is —(CR$^2$R$^y$)— then p is 2 and when M is —(CH$_2$)—(CR$^2$R$^y$)— or —(CR$^2$R$^y$)—(CH$_2$)— then p is 1,
or a pharmaceutically acceptable salt thereof.

2. The compound according to claim 1 which has the formula:

3. The compound according to claim 1, wherein R$^1$ is

4. The compound according to claim 1, wherein R$^2$ is Me.

5. The compound according to claim 1, wherein R$^3$

6. The compound according to claim 1, wherein R$^4$ is selected from the group consisting of n is 2; and
R is H or C$_{1-6}$alkyl.

7. The compound according to claim 1, wherein the compound of Formula (I) is selected from the group consisting of:

83
-continued
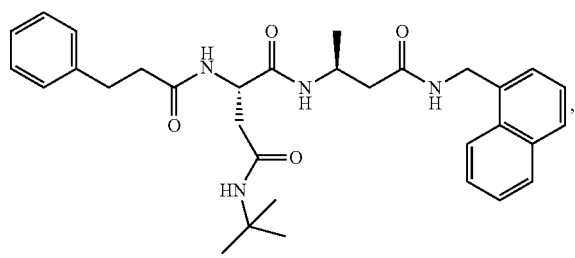
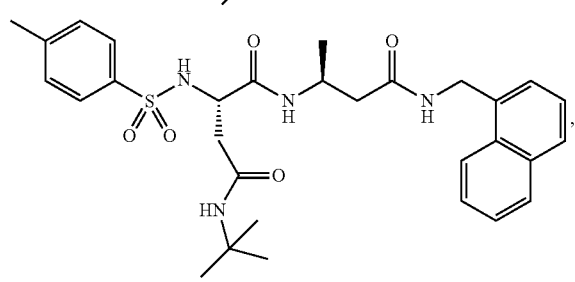
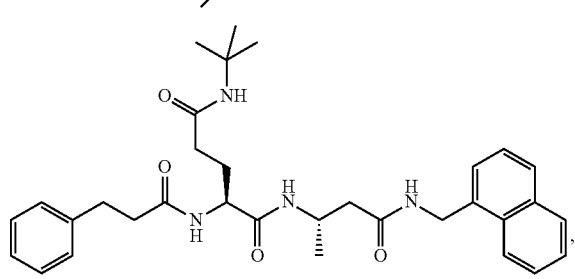
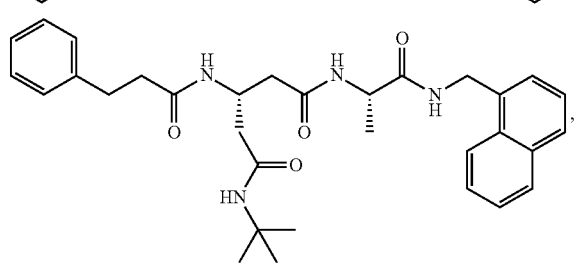
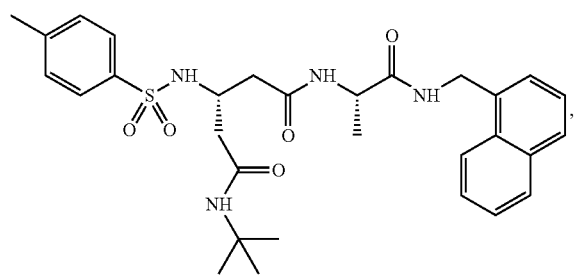
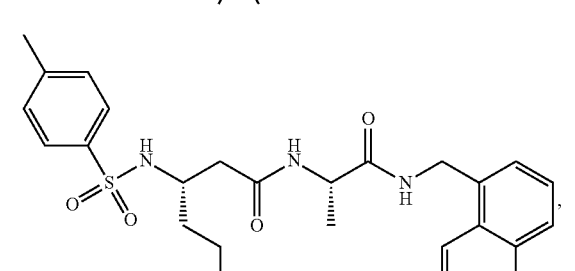
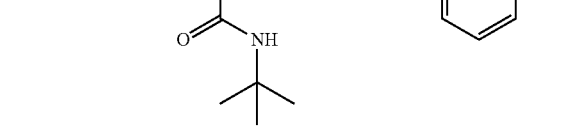
84
-continued
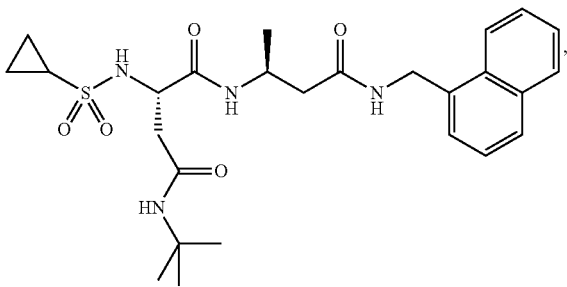
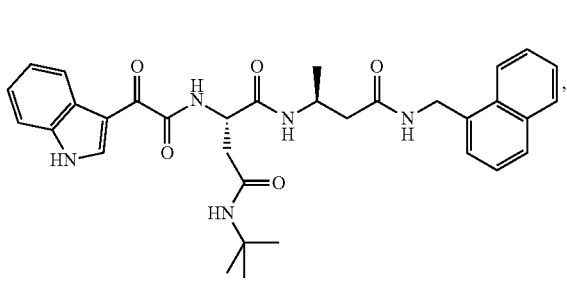
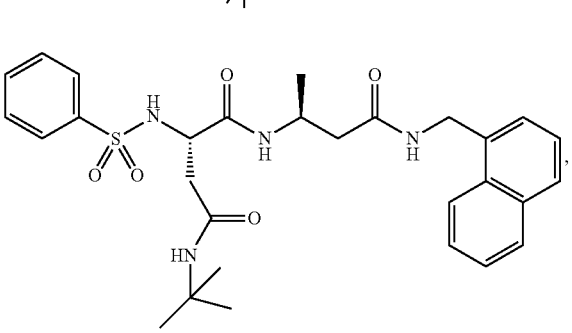
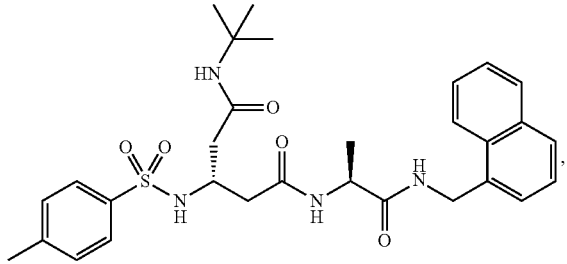
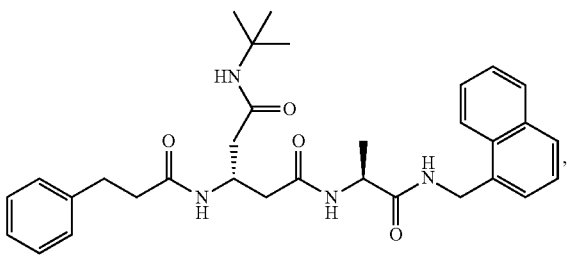
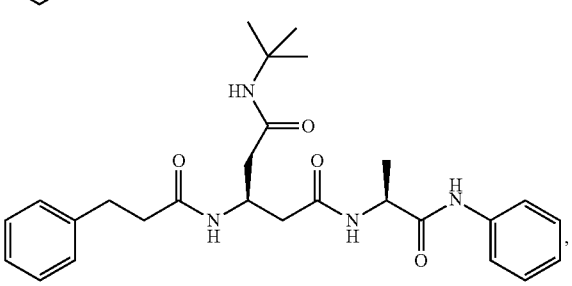

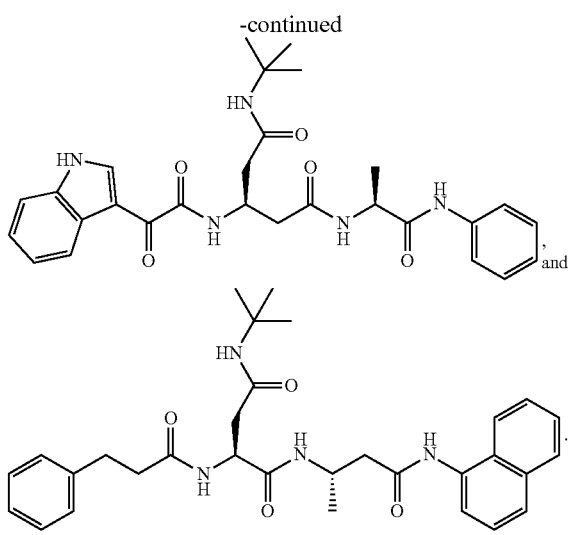
8. A pharmaceutical composition comprising a therapeutically effective amount of the compound according to claim 1 and a pharmaceutically acceptable carrier.
9. The compound according to claim 1, wherein the compound of Formula (I) is selected from the group consisting of:
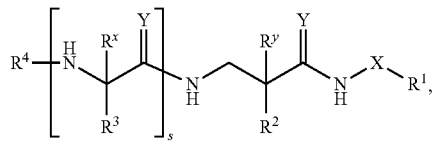
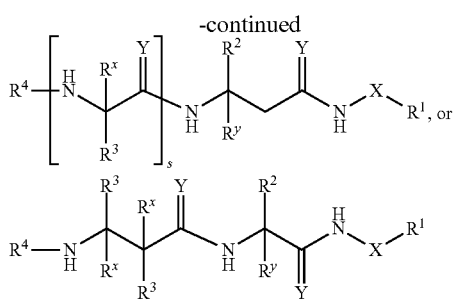
wherein
R$^3$ is H or —(CH$_2$)$_m$C(O)NHR$^5$.
10. The compound according to claim 1 which has the formula:
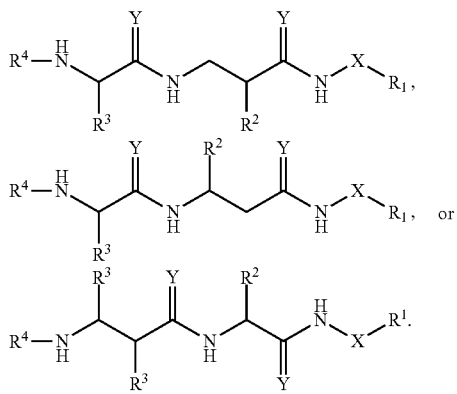
* * * * *

UNITED STATES PATENT AND TRADEMARK OFFICE
CERTIFICATE OF CORRECTION

PATENT NO. : 11,202,817 B2
APPLICATION NO. : 15/504951
DATED : December 21, 2021
INVENTOR(S) : Gang Lin et al.

Page 1 of 1

It is certified that error appears in the above-identified patent and that said Letters Patent is hereby corrected as shown below:

On the Title Page

Item (63), delete "Continuation of application No. PCT/US2015/044876, filed on Aug. 12, 2015."

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*